United States Patent [19]
Arnold et al.

[11] Patent Number: 5,945,325
[45] Date of Patent: Aug. 31, 1999

[54] THERMALLY STABLE PARA-NITROBENZYL ESTERASES

[75] Inventors: Frances H. Arnold; Lorraine J. Giver, both of Pasadena, Calif.

[73] Assignee: California Institute of Technology, Pasadena, Calif.

[21] Appl. No.: 09/062,890

[22] Filed: Apr. 20, 1998

[51] Int. Cl.$^6$ .............................. C12N 9/18; C12N 15/55
[52] U.S. Cl. ........................................... 435/197; 536/23.2
[58] Field of Search ............................. 435/197; 536/23.2

[56] References Cited

U.S. PATENT DOCUMENTS

| | | | |
|---|---|---|---|
| 5,316,935 | 5/1994 | Arnold et al. | 435/222 |
| 5,468,632 | 11/1995 | Cantwell et al. | 435/197 |
| 5,741,691 | 4/1998 | Arnold et al. | 435/197 |

OTHER PUBLICATIONS

J.C. Moore et al., "Strategies for the in vitro Evolution of Protein Function: Enzyme Evolution By Random Recombination of Improved Sequences", J. Mol. Biol. 272(3): 336–347, Sep. 1997.

F.H. Arnold et al., "Optimizing Industrial Enzymes By Directed Evolution", Advances Biochem. Engineering/Biotechnol. 58: 1–14, 1997.

Arnold, F.H., "Engineering proteins for nonnatural environments," The FASEB Journal, vol. 7, pp. 744–749, 1993.

Chen, K., et al., "Tuning the activity of an enzyme for visual environments: sequential random mutagenesis of subtilisin E for catalysis in dimethylformamide," Proc. Natl. Acad. Sci. USA, vol. 90, pp. 5618–5622, 1993.

Moore, J.C., et al., "Directed evolution of a para–nitrobenzyl esterase for aqueous–organic solvents," Nature Biotechnology, vol. 14, pp. 458–467, 1996

*Primary Examiner*—Rebecca E. Prouty
*Attorney, Agent, or Firm*—Oppenheimer Wolff & Donnelly LLP

[57] ABSTRACT

A method for isolating and identifying modified para-nitrobenzyl esterases which exhibit improved thermal stability relative to naturally occurring para-nitrobenzyl esterase. The method involves preparing a library of modified para-nitrobenzyl esterase nucleic acid segments (genes) which have nucleotide sequences that differ from the nucleic acid segment which encodes for naturally occurring para-nitrobenzyl esterase. The library of modified para-nitrobenzyl nucleic acid segments is expressed to provide a plurality of modified enzymes. The clones expressing modified enzymes are then screened to identify which enzymes retain esterase activity after heat treatment at elevated temperature. Specific modified para-nitrobenzyl esterases are disclosed which have improved thermal stability and/or ester hydrolysis activity in aqueous or aqueous-organic media relative to the thermal stability and/or ester hydrolysis activity of unmodified naturally occurring para-nitrobenzyl esterase.

15 Claims, 48 Drawing Sheets

LORACARBEF NUCLEUS-
p-NITROBENZYL
(LCN-pNB)

LORACARBEF
NUCLEUS
(LCN)

p-NITROBENZYL
ALCOHOL
(pNB)

p-NITROPHENYL ACETATE
(pNPA)

ACETATE p-NITROPHENOL
(pNP)

LORACARBEF NUCLEUS-
p-NITROPHENYL
(LCN-pNP)

LORACARBEF
NUCLEUS
(LCN)

p-NITROPHENOL
(pNP)

FIG. 11
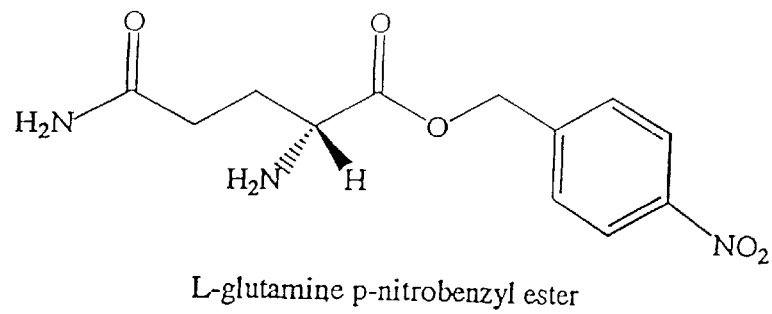
L-glutamine p-nitrobenzyl ester
a)
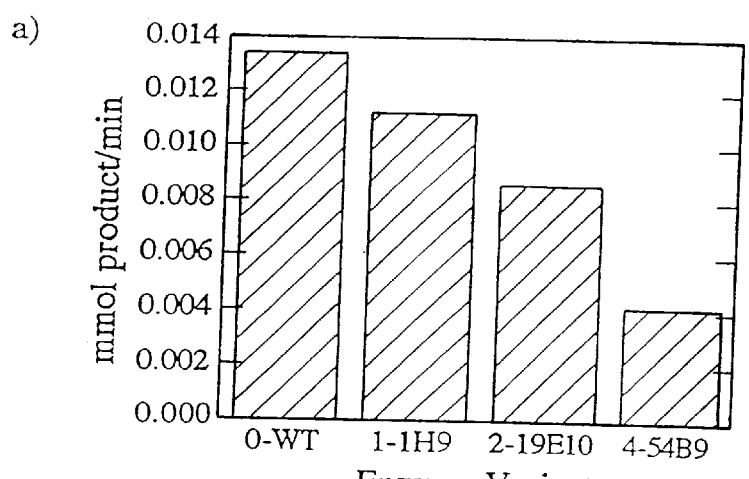
FIG. 11A
b)
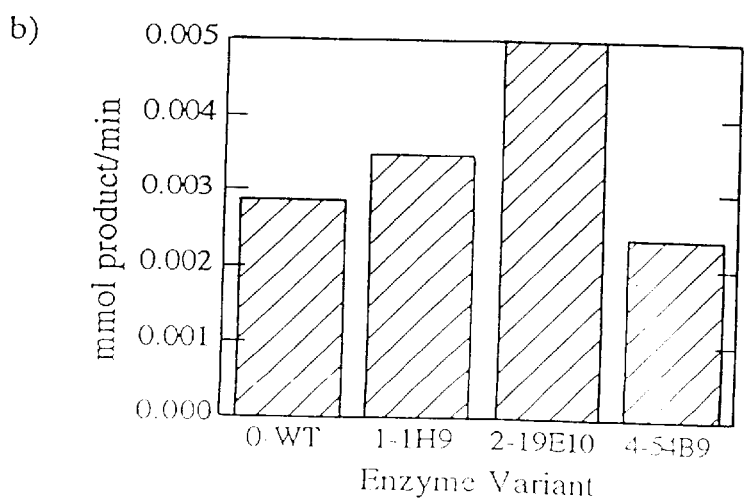
FIG. 11B

```
>wt      ATGACTCATC AAATAGTAAC GACTCAATAC GGCAAAGTAA
>1A5D1   ATGACTCATC AAATAGTAAC GACTCAATAC GGCAAAGTAA
>2A12    ATGACTCATC AAATAGTAAC GACTCAATAC GGCAAAGTAA
>3-H5    ATGACTCATC AAATAGTAAC GACTCAATAC GGCAAAGTAA
>4G4     ATGACTCATC AAATAGTAAC GACTCAATAC GGCAAAGTAA
>5H3     ATGACTCATC AAATAGTAAC GACTCAATAC GGCAAAGTAA
>6H7     ATGACTCATC AAATAGTAAC GACTCAATAC GGCAAAGTAA
>6sF9    ATGACTCATC AAATAGTAAC GACTCAATAC GGCAAAGTAA
    #1   ..........　..........　..........　..........
         ATGACTCATC AAATAGTAAC GACTCAATAC GGCAAAGTAA

>wt      AAGGCACAAC GGAAAACGGC GTACATAAGT GGAAAGGCAT
>1A5D1   AAGGCACAAC GGAAAACGGC GTACATAAGT GGAAAGGCAT
>2A12    AAGGCACAAC GGAAAACGGC GTACATAAGT GGAAAGGCAT
>3-H5    AAGGCACAAC GGAAAACGGC GTACATAAGT GGAAAGGCAT
>4G4     AAGGCACAAC GGAAAACGGC GTACATAAGT GGAAAGGCAT
>5H3     AAGGCACAAC GGAAAACGGC GTACATAAGT GGAAAGGCAT
>6H7     AAGGCACAAC GGAAAACGGC GTACATAAGT GGAAAGGCAT
>6sF9    AAGGCACAAC GGAAAACGGC GTACATAAGT GGAAAGGCAT
    #41  ..........　..........　..........　..........
         AAGGCACAAC GGAAAACGGC GTACATAAGT GGAAAGGCAT

>wt      CCCCTATGCC AAGCCGCCTG TCGGACAATG GCGTTTTAAA
>1A5D1   CCCTTATGCC AAGCCGCCTG TCGGACAATG GCGTTTTAAA
>2A12    CCCTTATGCC AAGCCGCCCG TCGGACAATG GCGTTTTAAA
>3-H5    CCCTTATGCC AAGCCGCCCG TCGGACAATG GCGTTTTAAA
>4G4     CCCTTATGCC AAGCCGCCCG TCGGACAATG GCGTTTTAAA
>5H3     CCCTTATGCC AAGCCGCCCG TCGGACAATG GCGTTTTAAA
>6H7     CCCTTATGCC AAGCCGCCCG TCGGACAATG GCGTTTTAAA
>6sF9    CCCCTATGCC AAGCCGCCCG TCGGACAATG GCGTTTTAAA
    #81  ..........　..........　..........　..........
         CCCTTATGCC AAGCCGCCCG TCGGACAATG GCGTTTTAAA
            *                *

>wt      GCACCTGAGC CGCCTGAAGT GTGGGAAGAT GTCCTTGATG
>1A5D1   GCACCTGAGC CGCCTGAAGT GTGGGAAGAT GTCCTTGATG
>2A12    GCACCTGAGC CGCCTGAAGT GTGGGAAGAT GTCCTTGATG
>3-H5    GCACCTGAGC CGCCTGAAGT GTGGGAAGAT GTCCTTGATG
>4G4     GCACCTGAGC CGCCTGAAGT GTGGGAAGAT GTCCTTGATG
>5H3     GCACCTGAGC CGCCTGAAGT GTGGGAAGAT GTCCTTGATG
>6H7     GCACCTGAGC CGCCTGAAGT GTGGGAAGAT GTCCTTGATG
>6sF9    GCACCTGAGC CGCCTGAAGT GTGGGAAGAT GTCCTTGATG
   #121  ..........　..........　..........　..........
         GCACCTGAGC CGCCTGAAGT GTGGGAAGAT GTCCTTGATG
```

FIG. 19A

```
>wt      CCACAGCGTA CGGTCCTATT TGCCCGCAGC CGTCTGATTT
>1A5D1   CCACAGCGTA CGGTCCTGTT TGCCCGCAGC CGTCTGATTT
>2A12    CCACAGCGTA CGGTCCTGTT TGCCCGCAGC CGTCTGATTT
>3-H5    CCACAGCGTA CGGTCCTGTT TGCCCGCAGC CGTCTGATTT
>4G4     CCACAGCGTA CGGTCCTGTT TGCCCGCAGC CGTCTGATTT
>5H3     CCACAGCGTA CGGTCCTGTT TGCCCGCAGC CGTCTGATTT
>6H7     CCACAGCGTA CGGTCCTGTT TGCCCGCAGC CGTCTGATTT
>6sF9    CCACAGCGTA CGGTCCTGTT TGCCCGCAGC CGTCTGATTT
    #161 ..........................................
         CCACAGCGTA CGGTCCTGTT TGCCCGCAGC CGTCTGATTT
                            *

>wt      GCTCTCACTG TCGTATACAG AGCTGCCCCG CCAGTCCGAG
>1A5D1   GCTCTCACTG TCGTATACAG AGCTGCCCCG CCAGTCCGAG
>2A12    GCTCTCACTG TCGTATACAG AGCTGCCCCG CCAGTCCGAG
>3-H5    GCTCTCACTG TCGTATACAG AGCTGCCCCG CCAGTCCGAG
>4G4     GCTCTCACTG TCGTATACAG AGCTGCCCCG CCAGTCCGAG
>5H3     GCTCTCACTG TCGTATACAG AGCTGCCCCG CCAGTCCGAG
>6H7     GCTCTCACTG TCGTATACAG AGCTGCCCCG CCAGTCCGAG
>6sF9    GCTCTCACTG TCGTATACAG AGCTGCCCCG CCAGTCCGAG
    #201 ..........................................
         GCTCTCACTG TCGTATACAG AGCTGCCCCG CCAGTCCGAG

>wt      GATTGCTTGT ATGTCAATGT ATTTGCGCCT GACACTCCAA
>1A5D1   GATTGCTTGT ATGTCAATGT ATTTGCGCCT GACACTCCAA
>2A12    GATTGCTTGT ATGTCAATGT ATTTGCGCCT GACACTCCAA
>3-H5    GATTGCTTGT ATGTCAATGT ATTTGCGCCT GACACTCCAA
>4G4     GATTGCTTGT ATGTCAATGT ATTTGCGCCT GACACTCCAA
>5H3     GATTGCTTGT ATGTCAATGT ATTTGCGCCT GACACTCCAA
>6H7     GATTGCTTGT ATGTCAATGT ATTTGCGCCT GACACTCCAA
>6sF9    GATTGCTTGT ATGTCAATGT ATTTGCGCCT GACACTCCAA
    #241 ..........................................
         GATTGCTTGT ATGTCAATGT ATTTGCGCCT GACACTCCAA

>wt      GTCAAAATCT TCCTGTCATG GTGTGGATTC ACGGAGGCGC
>1A5D1   GTCAAAACCT TCCTGTCATG GTGTGGATTC ACGGAGGCGC
>2A12    GTCAAAACCT TCCTGTCATG GTGTGGATTC ACGGAGGCGC
>3-H5    GTCAAAACCT TCCTGTCATG GTGTGGATTC ACGGAGGCGC
>4G4     GTCAAAACCT TCCTGTCATG GTGTGGATTC ACGGAGGCGC
>5H3     GTCAAAACCT TCCTGTCATG GTGTGGATTC ACGGAGGCGC
>6H7     GTCAAAACCT TCCTGTCATG GTGTGGATTC ACGGAGGCGC
>6sF9    GTCAAAACCT TCCTGTCATG GTGTGGATTC ACGGAGGCGC
    #281 ..........................................
         GTCAAAACCT TCCTGTCATG GTGTGGATTC ACGGAGGCGC
              *
```

FIG. 19B

```
>wt        TTTTTATCTT GGAGCGGGCA GTGAGCCATT GTATGACGGA
>1A5D1     TTTTTATCTA GGAGCGGGCA GTGAGCCATT GTATGACGGA
>2A12      TTTTTATCTA GGAGCGGGCA GTGAGCCATT GTATGACGGA
>3-H5      TTTTTATCTA GGAGCGGGCA GTGAGCCATT GTATGACGGA
>4G4       TTTTTATCTA GGAGCGGGCA GTGAGCCATT GTATGACGGA
>5H3       TTTTTATCTA GGAGCGGGCA GTGAGCCATT GTATGACGGA
>6H7       TTTTTATCTA GGAGCGGGCA GTGAGCCATT GTATGACGGA
>6sF9      TTTTTATCTA GGAGCGGGCA GTGAGCCATT GTATGACGGA
     #321  ..........................................
           TTTTTATCTA GGAGCGGGCA GTGAGCCATT GTATGACGGA
                    *

>wt        TCAAAACTTG CGGCACAGGG AGAAGTCATT GTCGTTACAT
>1A5D1     TCAAAACTTG CGGCACAGGG AGAAGTCATT GTCGTTACAT
>2A12      TCAAAACTTG CGGCACAGGG AGAAGTCATT GTCGTTACAT
>3-H5      TCAAAACTTG CGGCACAGGG AGAAGTCATT GTCGTTACAT
>4G4       TCAAAACTTG CGGCACAGGG AGAAGTCATT GTCGTTACAT
>5H3       TCAAAACTTG CGGCGCAGGG AGAAGTCATT GTCGTTACAT
>6H7       TCAAAACTTG CGGCGCAGGG AGAAGTCATT GTCGTTACAT
>6sF9      TCAAAACTTG CGGCACAGGG AGAAGTCATT GTCGTTACAT
     #361  ..........................................
           TCAAAACTTG CGGCACAGGG AGAAGTCATT GTCGTTACAT
                         *

>wt        TGAACTATCG GCTGGGGCCG TTTGGCTTTT TGCACTTGTC
>1A5D1     TGAACTATCG GCTGGGGCCG TTTGGCTTTA TGCACTTGTC
>2A12      TGAACTATCG GCTGGGGCCG TTTGGCTTTA TGCACTTGTC
>3-H5      TGAACTATCG GCTGGGGCCG TTTGGCTTTA TGCACTTGTC
>4G4       TGAACTATCG GCTGGGGCCG TTTGGCTTTA TGCACTTGTC
>5H3       TGAACTATCG GCTGGGGCCG TTTGGCTTTA TGCACTTGTC
>6H7       TGAACTATCG GCTGGGGCCG TTTGGCTTTA TGCACTTGTC
>6sF9      TGAACTATCG GCTGGGGCCG TTTGGCTTTA TGCACTTGTC
     #401  ..........................................
           TGAACTATCG GCTGGGGCCG TTTGGCTTTA TGCACTTGTC
                                         *

>wt        TTCGTTTGAT GAGGCGTATT CCGATAACCT TGGGCTTTTA
>1A5D1     TTCGTTTGAT GAGGCGTATT CCGATAACCT TGGGCTTTTA
>2A12      TTCGTTTGAT GAGGCGTATT CCGATAACCT TGGGCTTTTA
>3-H5      TTCGTTTGAT GAGGCGTATT CCGATAACCT TGGGCTTTTA
>4G4       TTCGTTTGAT GAGGCGTATT CCGATAACCT TGGGCTTTTA
>5H3       TTCGTTTGAT GAGGCGTATT CCGATAACCT TGGGCTTTTA
>6H7       TTCGTTTGAT GAGGCGTATT CCGATAACCT TGGGCTTTTA
>6sF9      TTCGTTTGAT GAGGCGTATT CCGATAACCT TGGGCTTTTA
     #441  ..........................................
           TTCGTTTGAT GAGGCGTATT CCGATAACCT TGGGCTTTTA
```

FIG. 19C

```
>wt      GACCAAGCCG CCGCGCTGAA ATGGGTGCGG GAGAATATCT
>1A5D1   GACCAAGCCG CCGCGCTGAA ATGGGTGCGG GAGAATATCT
>2A12    GACCAAGCCG CCGCGCTGAA ATGGGTGCGG GAGAATATCT
>3-H5    GACCAAGCCG CCGCGCTGAA ATGGGTGCGG GAGAATATCT
>4G4     GACCAAGCCG CCGCGCTGAA ATGGGTGCGG GAGAATATCT
>5H3     GACCAAGCCG CCGCGCTGAA ATGGGTGCGG GAGAATATCT
>6H7     GACCAAGCCG CCGCGCTGAA ATGGGTGCGG GAGAATATCT
>6sF9    GACCAAGCCG CCGCGCTGAA ATGGGTGCGG GAGAATATCT
   #481  ..........................................
         GACCAAGCCG CCGCGCTGAA ATGGGTGCGG GAGAATATCT

>wt      CAGCGTTTGG CGGTGATCCC GATAACGTAA CAGTATTTGG
>1A5D1   CAGCGTTTGG CGGTGATCCC GATAACGTAA CAGTATTTGG
>2A12    CAGCGTTTGG CGGTGATCCC GATAACGTAA CAGTATTTGG
>3-H5    CAGCGTTTGG CGGTGATCCC GATAACGTAA CAGTATTTGG
>4G4     CAGCGTTTGG CGGTGATCCC GATAACGTAA CAGTATTTGG
>5H3     CAGCGTTTGG CGGTGATCCC GATAACGTAA CAGTATTTGG
>6H7     CAGCGTTTGG CGGTGATCCC GATAACGTAA CAGTATTTGG
>6sF9    CAGCGTTTGG CGGTGATCCC GATAACGTAA CAGTATTTGG
   #521  ..........................................
         CAGCGTTTGG CGGTGATCCC GATAACGTAA CAGTATTTGG

>wt      AGAATCCGCC GGCGGCATGA GCATTGCCGC GCTGCTCGCT
>1A5D1   AGAATCCGCC GGCGGCATGA GCATTGCCGC GCTGCTCGCT
>2A12    AGAATCCGCC GGCGGCATGA GCATTGCCGC GCTGCTCGCT
>3-H5    AGAATCCGCC GGCGGCATGA GCATTGCCGC GCTGCTCGCT
>4G4     AGAATCCGCC GGCGGCATGA GCATTGCCGC GCTGCTCGCT
>5H3     AGAATCCGCC GGCGGCATGA GCATTGCCGC GCTGCTCGCT
>6H7     AGAATCCGCC GGCGGCATGA GCATTGCCGC GCTGCTCGCT
>6sF9    AGAATCCGCC GGCGGCATGA GCATTGCCGC GCTGCTCGCT
   #561  ..........................................
         AGAATCCGCC GGCGGCATGA GCATTGCCGC GCTGCTCGCT

>wt      ATGCCTGCGG CAAAAGGCCT GTTCCAGAAA GCGATCATGG
>1A5D1   ATGCCTGCGG CAAAAGGCCT GTTCCAGAAA GCGATCATGG
>2A12    ATGCCTGCGG CAAAAGGCCT GTTCCAGAAA GCGATCATGG
>3-H5    ATGCCTGCGG CAAAAGGCCT GTTCCAGAAA GCGATCATGG
>4G4     ATGCCTGCGG CAAAAGGCCT GTTCCAGAAA GCGATCATGG
>5H3     ATGCCTGCGG CAAAAGGCCT GTTCCAGAAA GCGATCATGG
>6H7     ATGCCTGCGG CAAAAGGCCT GTTCCAGAAA GCGATCATGG
>6sF9    ATGCCTGCGG CAAAAGGCCT GTTCCAGAAA GCGATCATGG
   #601  ..........................................
         ATGCCTGCGG CAAAAGGCCT GTTCCAGAAA GCGATCATGG
```

FIG. 19D

```
>wt        AAAGCGGCGC TTCCCGAACA ATGACAAAAG AACAAGCGGC
>1A5D1     AAAGCGGCGC TTCCCGAACA ATGACAAAAG AACAAGCGGC
>2A12      AAAGCGGCGC TTCCCGAACA ATGACAAAAG AACAAGCGGC
>3-H5      AAAGCGGCGC TTCCCGAACA ATGACAAAAG AACAAGCGGC
>4G4       AAAGCGGCGC TTCCCGAACA ATGACAAAAG AACAAGCGGC
>5H3       AAAGCGGCGC TTCCCGAACA ATGACAAAAG AACAAGCGGC
>6H7       AAAGCGGCGC TTCCCGAACA ATGACAAAAG AACAAGCGGC
>6sF9      AAAGCGGCGC TTCCCGAACA ATGACAAAAG AACAAGCGGC
     #641  ..........  ..........  ..........  ..........
           AAAGCGGCGC TTCCCGAACA ATGACAAAAG AACAAGCGGC

>wt        AAGCACTGCG GCTGCCTTTT TACAGGTCCT TGGGATTAAT
>1A5D1     AAGCACTGCG GCTGCCTTTT TACAGGTCCT TGGGATTAAT
>2A12      AAGCACTGCG GCTGCCTTTT TACAGGTCCT TGGGATTAAT
>3-H5      AAGCACTGCG GCTGCCTTTT TACAGGTCCT TGGGATTAAT
>4G4       AAGCACTGCG GCTGCCTTTT TACAGGTCCT TGGGATTAAT
>5H3       AAGCACTGCG GCTGCCTTTT TACAGGTCCT TGGGATTAAT
>6H7       AAGCACTGCG GCTGCCTTTT TACAGGTCCT TGGGATTAAT
>6sF9      AAGCACTGCG GCTGCCTTTT TACAGGTCCT TGGGATTAAT
     #681  ..........  ..........  ..........  ..........
           AAGCACTGCG GCTGCCTTTT TACAGGTCCT TGGGATTAAT

>wt        GAGAGCCAGC TGGACAGATT GCATACTGTA GCAGCGGAAG
>1A5D1     GAGAGCCAGC TGGACAGATT GCATACTGTA GCAGCGGAAG
>2A12      GAGAGCCAGC TGGACAGATT GCATACTGTA GCAGCGGAAG
>3-H5      GAGAGCCAGC TGGACAGATT GCATACTGTA GCAGCGGAAG
>4G4       GAGAGCCAGC TGGACAGATT GCATACTGTA GCAGCGGAAG
>5H3       GAGAGCCAGC TGGACAGATT GCATACTGTA GCAGCGGAAG
>6H7       GAGAGCCAGC TGGACAGATT GCATACTGTA GCAGCGGAAG
>6sF9      GAGAGCCAGC TGGACAGATT GCATACTGTA GCAGCGGAAG
     #721  ..........  ..........  ..........  ..........
           GAGAGCCAGC TGGACAGATT GCATACTGTA GCAGCGGAAG

>wt        ATTTGCTTAA AGCGGCCGAT CAGCTTCGGA TTGCAGAAAA
>1A5D1     ATTTGCTTAA AGCGGCCGAT CAGCTTCGGA TTGCAGAAAA
>2A12      ATTTGCTTAA AGCGGCCGAT CAGCTTCGGA TTGCAGAAAA
>3-H5      ATTTGCTTAA AGCGGCCGAT CAGCTTCGGA TTGCAGAAAA
>4G4       ATTTGCTTAA AGCGGCCGAT CAGCTTCGGA TTGCAGAAAA
>5H3       ATTTGCTTAA AGCGGCCGAT CAGCTTCGGA TTGCAGAAAA
>6H7       ATTTGCTTAA AGCGGCCGAT CAGCTTCGGA TTGCAGAAAA
>6sF9      ATTTGCTTAA AGCGGCCGAT CAGCTTCGGA TTGCAGAAAA
     #761  ..........  ..........  ..........  ..........
           ATTTGCTTAA AGCGGCCGAT CAGCTTCGGA TTGCAGAAAA
```

FIG. 19E

```
>wt         AGAAAATATC TTTCAGCTGT TCTTCCAGCC CGCCCTTGAT
>1A5D1      AGAAAATATC TTTCAGCTGT TCTTCCAGCC CGCCCTTGAT
>2A12       AGAAAATATC TTTCAGCTGT TCTTCCAGCC CGCCCTTGAT
>3-H5       AGAAAATATC TTTCAGCTGT TCTTCCAGCC CGCCCTTGAT
>4G4        AGAAAATATC TTTCAGCTGC TCTTCCAGCC CGCCCTTGAT
>5H3        AGAAAATATC TTTCAGCTGC TCTTCCAGCC CGCCCTTGAT
>6H7        AGAAAATATC TTTCAGCTGT TCTTCCAGCC CGCCCTTGAT
>6sF9       AGAAAATATC TTTCAGCTGT TCTTCCAGCC CGCCCTTGAT
      #801  .......... .......... .......... ..........
            AGAAAATATC TTTCAGCTGT TCTTCCAGCC CGCCCTTGAT
                                *

>wt         CCGAAAACGC TGCCTGAAGA ACCAGAAAAA TCGATCGCAG
>1A5D1      CCGAAAACGC TGCCTGAAGA ACCAGAAAAA TCGATCGCAG
>2A12       CCGAAAACGC TGCCTGAAGA ACCAGAAAAA TCGATCGCAG
>3-H5       CCGAAAACGC TGCCTGAAGA ACCAGAAAAA TCGATCGCAG
>4G4        CCGAAAACGC TGCCTGAAGA ACCAGAAAAA TCGATCGCAG
>5H3        CCGAAAACGC TGCCTGAAGA ACCAGAAAAA TCGATCGCAG
>6H7        CCGAAAACGC TGCCTGAAGA ACCAGAAAAA TCGATCGCAG
>6sF9       CCGAAAACGC TGCCTGAAGA ACCAGAAAAA TCGATCGCAG
      #841  .......... .......... .......... ..........
            CCGAAAACGC TGCCTGAAGA ACCAGAAAAA TCGATCGCAG

>wt         AAGGGGCTGC TTCCGGCATT CCGCTATTGA TTGGAACAAC
>1A5D1      AAGGGGCTGC TTCCGGCATT CCGCTATTGA TTGGAACAAC
>2A12       AAGGGGCTGC TTCCGGCATT CCGCTATTGA TTGGAACAAC
>3-H5       AAGGGGCTGC TTCCGGCATT CCGCTATTGA TTGGAACAAC
>4G4        AAGGGGCTGC TTCCGGCATT CCGCTATTGA TTGGAACAAC
>5H3        AAGGGGCTGC TTCCGGCATT CCGCTATTGA TTGGAACAAC
>6H7        AAGGGGCTGC TTCCGGCATT CCGCTATTGA TTGGAACAAC
>6sF9       AAGGGGCTGC TTCCGGCATT CCGCTATTGA TTGGAACAAC
      #881  .......... .......... .......... ..........
            AAGGGGCTGC TTCCGGCATT CCGCTATTGA TTGGAACAAC

>wt         CCGTGATGAA GGATATTTAT TTTTCACCCC GGATTCAGAC
>1A5D1      CCGTGATGAA GGATATTTAT TTTTCACCCC GGATTCAGAC
>2A12       CCGTGATGAA GGATATTTAT TTTTCACCCC GGATTCAGAC
>3-H5       CCGTGATGAA GGATATTTAT TTTTCACCCC GGATTCAGAC
>4G4        CCGTGATGAA GGATATTTAT TTTTCACCCC GGATTCAGAC
>5H3        CCGTGATGAA GGATATTCT  TTTTCACCCC GGATTCAGAC
>6H7        CCGTGATGAA GGATATTTCT TTTTCACCCC GGATTCAGAC
>6sF9       CCGTGATGAA GGATATTTCT TTTTCACCCC GGATTCAGAC
      #921  .......... .......... .......... ..........
            CCGTGATGAA GGATATTTAT TTTTCACCCC GGATTCAGAC
                             *
```

FIG. 19F

```
>wt        GTTCATTCTC AGGAAACGCT TGATGCAGCA CTCGAGTATT
>1A5D1     GTTCGTTCTC AGGAAACGCT TGATGCAGCA CTCGAGTATT
>2A12      GTTCGTTCTC AGGAAACGCT TGATGCAGCA CTCGAGTATT
>3-H5      GTTTGTTCTC AGGAAACGCT TGATGCAGCA CTCGAGTATT
>4G4       GTTTATTCTC AGGAAACGCT TGATGCAGCA CTCGAGTATT
>5H3       GTTTATTCTC AGGAAACGCT TGATGCAGCA CTCGAGTATT
>6H7       GTTTATTCTC AGGAAACGCT TGATGCAGCA CTCGAGTATT
>6sF9      GTTTATTCTC AGGAAACGCT TGATGCAGCA CTCGAGTATT
     #961  ..........  .......... .......... ..........
           GTTTATTCTC AGGAAACGCT TGATGCAGCA CTCGAGTATT
               **

>wt        TACTAGGGAA GCCGCTGGCA GAGAAAGCTG CCGATTTGTA
>1A5D1     TACTAGGGAA GCCGCTGGCA GAGAAAGCTG CCGATTTGTA
>2A12      TACTAGGGAA GCCGCTGGCA GAGAAAGTTG CCGATTTGTA
>3-H5      TACTAGGGAA GCCGCTGGCA GAGAAAGTTG CCGATTTGTA
>4G4       TACTAGGGAA GCCGCTGGCA GAGAAAGTTG CCGATTTGTA
>5H3       TACTAGGGAA GCCGCTGGCA GAGAAAGTTG CCGATTTGTA
>6H7       TACTAGGGAA GCCGCTGGCA GAGAAAGTTG CCGATTTGTA
>6sF9      TACTAGGGAA GCCGCTGGCA GAGAAAGTTG CCGATTTGTA
    #1001  ..........  .......... .......... ..........
           TACTAGGGAA GCCGCTGGCA GAGAAAGTTG CCGATTTGTA
                                         *

>wt        TCCGCGTTCT CTGGAAAGCC AAATTCATAT GATGACTGAT
>1A5D1     TCCGCGTTCT CTGGAAAGCC AAATTCATAT GGTGACTGAT
>2A12      TCCGCGTTCT CTGGAAAGCC AAATTCATAT GGTGACTGAT
>3-H5      TCCGCGTTCT CTGGAAAGCC AAATTCATAT GGTGACTGAT
>4G4       TCCGCGTTCT CTGGAAAGCC AAATTCATAT GGTGACTGAT
>5H3       TCCGCGTTCT CTGGAAAGCC AAATTCATAT GGTGACTGAT
>6H7       TCCGCGTTCT CTGGAAAGCC AAATTCATAT GGTGACTGAT
>6sF9      TCCGCGTTCT CTGGAAAGCC AAATTCATAT GGTGACTGAT
    #1041  ..........  .......... .......... ..........
           TCCGCGTTCT CTGGAAAGCC AAATTCATAT GGTGACTGAT
                                             *

>wt        TTATTATTTT GGCGCCCTGC CGTCGCCTAT GCATCCGCAC
>1A5D1     TTATTATTTT GGCGCCCTGC CGTCGCCTTT GCATCCGCAC
>2A12      TTATTATTTT GGCGCCCTGC CGTCGCCTTT GCATCCGCAC
>3-H5      TTATTATTTT GGCGCCCTGC CGTCGCCTTT GCATCCGCAC
>4G4       TTATTATTTT GGCGCCCTGC CGTCGCCTTT GCATCCGCAC
>5H3       TTATTATTTT GGCGCCCTGC CGTCGCCTTT GCATCCGCAC
>6H7       TTATTATTTT GGCGCCCTGC CGTCGCCTTT GCATCCGCAC
>6sF9      TTATTATTTT GGCGCCCTGC CGTCGCCTTT GCATCCGCAC
    #1081  ..........  .......... .......... ..........
           TTATTATTTT GGCGCCCTGC CGTCGCCTTT GCATCCGCAC
                                         *
```

FIG. 19G

```
>wt       AGTCTCATTA CGCCCCTGTC TGGATGTACC GGTTCGATTG
>1A5D1    AGTCTCATTA CGCCCCTGTC TGGATGTACC GGTTCGATTG
>2A12     AGTCTCATTA CGCCCCTGTC TGGATGTACC GGTTCGATTG
>3-H5     AGTCTCATTA CGCCCCTGTC TGGATGTACC GGTTCGATTG
>4G4      AGTCTCATTA CGCCCCTGTC TGGATGTACC GGTTCGATTG
>5H3      AGTCTCATTA CGCCCCTGTC TGGATGTACC GGTTCGATTG
>6H7      AGTCTCATTA CGCCCCTGTC TGGATGTACC GGTTCGATTG
>6sF9     AGTCTCATTA CGCCCCTGTC TGGATGTACC GGTTCGATTG
    #1121 .......... .......... .......... ..........
          AGTCTCATTA CGCCCCTGTC TGGATGTACC GGTTCGATTG

>wt       GCACCCGGAG AAGCCGCCGT ACAATAAAGC GTTTCACGCA
>1A5D1    GCACCCGGAG AAGCCGCCGT ACAATAAAGC GTTTCACGCA
>2A12     GCACCCGGAG AAGCCGCCGT ACAATAAAGC GTTTCACGCA
>3-H5     GCACCCGGAG AAGCCGCCGT ACAATAAAGC GTTTCACGCA
>4G4      GCACCCGGAG AAGCCGCCGT ACAATAAAGC GTTTCACGCA
>5H3      GCACCCGGAG AAGCCGCCGT ACAATAAAGC GTTTCACGCA
>6H7      GCACCCGGAG AAGCCGCCGT ACAATAAAGC GTTACACGCA
>6sF9     GCACCCGGAG AAGCCGCCGT ACAATAAAGC GTTTCACGCA
    #1161 .......... .......... .......... ..........
          GCACCCGGAG AAGCCGCCGT ACAATAAAGC GTTTCACGCA
                                                 *

>wt       TTAGAGCTTC CTTTTGTCTT TGGAAATCTG GACGGATTGG
>1A5D1    TTAGAGCTTC CTTTTGTCTT TGGAAATCTG GACGGATTGG
>2A12     TTAGAGCTTC CTTTTGTCTT TGGAAATCTG GACGGATTGG
>3-H5     TTAGAGCTTC CTTTTGTCTT TGGAAATCTG GACGGATTGG
>4G4      TTAGAGCTTC CTTTTGTCTT TGGAAATCTG GACGGGTTGG
>5H3      TTAGAGCTTC CTTTTGTCTT TGGAAATCTG GACGGGTTGG
>6H7      TTAGAGCTTC CTTTTGTCTT TGGAAATCTG GACGGGTTGG
>6sF9     TTAGAGCTTC CTTTTGTCTT TGGAAATCTG GACGAGTTGG
    #1201 .......... .......... .......... ..........
          TTAGAGCTTC CTTTTGTCTT TGGAAATCTG GACGGRTTGG
                                                **

>wt       AACGAATGGC AAAAGCGGAG ATTACGGATG AGGTGAAACA
>1A5D1    AACGAATGGC AAAAGCGGAG ATTACGGATG AGGTGAAACA
>2A12     AACGAATGGC AAAAGCGGAG ATTACGGATG AGGTGAAACA
>3-H5     AACGAATGGC AAAAGCGGAG ATTACGGATG AGGTGAAACA
>4G4      AACGAATGGC AAAAGCGGAG ATTACGGATG AGGTGAAACA
>5H3      AACGAATGGC AAAAGCGGAG ATTACGGATG AGGTGAAACA
>6H7      AACGAATGGC AAAAGCGGAG ATTACGGATG AGGTGAAACA
>6sF9     AACGAATGGC AAAAGCGGAG ATTACGGATG AGGTGAAACA
    #1241 .......... .......... .......... ..........
          AACGAATGGC AAAAGCGGAG ATTACGGATG AGGTGAAACA
```

FIG. 19H

```
>wt      GCTTTCTCAC ACGATACAAT CCGCGTGGAT CACGTTCGCT
>1A5D1   GCTTTCTCAC ACGATACAAT CCGCGTGGAT CACGTTCGCT
>2A12    GCTTTCTCAC ACGATACAAT CCGCGTGGAT CACGTTCGCT
>3-H5    GCTTTCTCAC ACGATACAAT CCGCGTGGAT CACGTTCGCT
>4G4     GCTTTCTCAC ACGATACAAT CCGCGTGGAC CACGTTCGCT
>5H3     GCTTTCTCAC ACGATACAAT CCGCGTGGAC CACGTTCGCT
>6H7     GCTTTCTCAC ACGATACAAT CCGCGTGGAC CACGTTCGCT
>6sF9    GCTTTCCCAC ACGATACAAT CCGCGTGGAC CACGTTCGCT
   #1281 ..........  ..........  ..........  ..........
         GCTTTCTCAC ACGATACAAT CCGCGTGGAY CACGTTCGCT
              *                         *

>wt      AAAACAGGAA ACCCAAGCAC CGAAGCTGTG AATTGGCCGG
>1A5D1   AAAACAGGAA ACCCAAGCAC CGAAGCTGTG AATTGGCCGG
>2A12    AAAACAGGAA ACCCAAGCAC CGAAGCTGTG AATTGGCCGG
>3-H5    AAAACAGGAA ACCCAAGCAC CGAAGCTGTG AATTGGCCGG
>4G4     AAAACAGGAA ACCCAAGCAC CGAAGCTGTG AATTGGCCGG
>5H3     AAAACAGGAA ACCCAAGCAC CGAAGCTGTG AATTGGCCGG
>6H7     AAAACAGGAA ACCCAAGCAC CGAAGCTGTG AATTGGCCGG
>6sF9    AAAACAGGAA ACCCAAGCAC CGAAGCTGTG AATTGGCCGG
   #1321 ..........  ..........  ..........  ..........
         AAAACAGGAA ACCCAAGCAC CGAAGCTGTG AATTGGCCGG

>wt      CGTATCATGA AGAAACGAGA GAGACGGTGA TTTTAGACTC
>1A5D1   CGTATCATGA AGAAACGAGA GAGACGGTGA TTTTAGACTC
>2A12    CGTATCATGA AGAAACGAGA GAGACGGTGA TTTTAGACTC
>3-H5    CGTATCATGA AGAAACGAGA GAGACGGTGA TTTTAGACTC
>4G4     CGTATCATGA AGAAACGAGA GAGACGGTGA TTTTAGACTC
>5H3     CGTATCATGA AGAAACGAGA GAGACGGTGA TTTTAGACTC
>6H7     CGTATCATGA AGAAACGAGA GAGACGGTGA TTTTAGACTC
>6sF9    CGTATCATGA AGAAACGAGA GAGACGGTGA TTTTAGACTC
   #1361 ..........  ..........  ..........  ..........
         CGTATCATGA AGAAACGAGA GAGACGGTGA TTTTAGACTC

>wt      AGAGATTACG ATCGAAAACG ATCCCGAATC TGAAAAAAGG
>1A5D1   AGAGATTACG ATCGAAAACG ATCCCGAATC TGAAAAAAGG
>2A12    AGAGATTACG ATCGAAAACG ATCCCGAATC TGAAAAAAGG
>3-H5    AGAGATTACG ATCGAAAACG ATCCCGAATC TGAAAAAAGG
>4G4     AGAGATTACG ATCGAAAACG ATCCCGAATC TGAAAAAAGG
>5H3     AGAGATTACG ATCGAAAACG ATCCCGAATC TGAAAAAAGG
>6H7     AGAGATTACG ATCGAAAACG ATCCCGAATC TGAAAAAAGG
>6sF9    AGAGATTACG ATCGAAAACG ATCCCGAATC TGAAAAAAGG
   #1401 ..........  ..........  ..........  ..........
         AGAGATTACG ATCGAAAACG ATCCCGAATC TGAAAAAAGG
```

FIG. 19I

```
>wt       CAGAAGCTAT TCCCTTCAAA AGGAGAATAA
>1A5D1    CAGAAGCTAT TCCCTTCAAA AGGAGAATAA
>2A12     CAGAAGCTAT TCCCTTCAAA AGGAGAATAA
>3-H5     CAGAAGCTAT TCCCTTCAAA AGGAGAATAA
>4G4      CAGAAGCTAT TCCCTTCAAA AGGAGAATAA
>5H3      CAGAAGCTAT TCCCTTCAAA AGGAGAATAA
>6H7      CAGAAGCTAT TCCCTTCAAA AGGAGAATAA
>6sF9     CAGAAGCTAT TCCCTTCAAA AGGAGAATAA
    #1441          ........................................
          CAGAAGCTAT TCCCTTCAAA AGGAGAATAA
```

FIG. 19J

THERMALLY STABLE PARA-NITROBENZYL ESTERASES

The U.S. Government has certain rights in this invention pursuant to Grant No. DAAG55-97-C-0002 awarded by the Department of the Army.

BACKGROUND OF THE INVENTION

1. Field of the Invention

This invention relates to the creation, optimization and use of new thermostable esterase enzymes. More particularly, the invention relates to thermostable enzymes optimized to remove ester-linked para-nitrobenzyl (pNB) protecting groups from carboxyl functional groups on b-lactam antibiotics and other compounds. This invention also relates to methods by which such enzymes can be altered and optimized for specific substrates and reaction conditions. Also, this invention relates to purifying thermostable enzymes based on their ability to withstand relatively high temperatures.

2. Description of Related Art

The publications and other reference materials referred to herein to describe the background of the invention and to provide additional details regarding its practice are hereby incorporated by reference. For convenience, the reference materials are numerically referenced and identified in the appended bibliography.

Efficient protection and deprotection of functional groups is critical to successful organic synthesis of polyfunctional molecules. Synthetic schemes often require that a given functional group be protected or deprotected selectively, under the mildest conditions and in the presence of functional groups of similar reactivity or other structures that are sensitive to acids, bases, oxidation and reduction. These situations represent severe problems for the synthesis of complex, polyfunctional molecules which cannot, or only with great difficulty, be solved using classical chemical tools.

The array of protecting group techniques can be substantially enriched by the application of enzymes. Enzymes can discriminate stereoisomers as well as offer the opportunity to carry out highly chemo- and regioselective transformations. The highly selective nature of enzymes may be exploited advantageously in the manipulation of protecting groups and in the synthesis of chiral compounds such as drugs and natural products. Furthermore, enzymes function under mild conditions, often operating at or near room temperature and at neutral, weakly acidic or weakly basic pH values. In many cases they combine a high selectivity for the reactions they catalyze with a broad substrate tolerance. Therefore, the application of enzymes can be viable alternatives to classical chemical protection/deprotection methods for the introduction and/or removal of suitable protecting groups (1). The introduction of new enzymes with reactivities and temperature tolerances differing from existing enzymes is highly desirable.

Carboxy groups are often protected by conversion to the benzyl or para-nitrobenzyl (pNB) esters (2). Benzyl esters are resistant to treatment with reagents such as trifluoroacetic acid, triethylamine, diisopropylethylamine, but are readily removed by hydrogenolysis (over a Pd catalyst). Hydrogenolysis is not appropriate, however, for compounds containing double bonds, azides, imines, or activated aldehydes, or other functional groups that will be reduced. Benzyl esters can also be cleaved using a zinc catalyst under anhydrous conditions, but the extent of hydrolysis is variable and dependent on the conditions (e.g., time and temperature) of the reaction. The reaction must be carried out under anhydrous conditions, in an organic solvent. Both the organic solvent and catalyst can give rise to toxicity or disposal problems for large-scale reactions.

Modification by substitution in the aromatic ring can alter the sensitivity of the benzyl group towards deprotection by acidic reagents. PNB esters display increased resistance to acid hydrolysis.

During total synthesis or chemical modification of an antibiotic, several sites on the antibiotic could be adversely affected by the reagents used to carry out any given reaction step. Para-nitrobenzyl alcohol (pNB-OH) is commonly used to protect carboxylic acid functionalities in cephalosporin-derived antibiotics (U.S. Pat. No. 3,725,359 [1975]) (3). The pNB ester linkage is stable enough to withstand the various reaction conditions used in subsequent chemical steps. After chemical synthesis is completed, deprotection is required to return the cephalosporin-pNB ester to its original and active carboxylic acid form. The chemistry used to deprotect the carboxylic acid involves a catalytic form of zinc in concentrated organic solvent, and on an industrial scale this process generates large amounts of solvent and zinc-containing waste material. Cost is associated with processing of waste to make it safe for disposal. In 1975, scientists at Eli Lilly & Co. interested in pursuing alternative methods of deprotection for higher yield and lower disposal costs began a search for an esterase capable of performing this deprotection reaction (3).

The enzyme known as para-nitrobenzyl esterase (pNB esterase) was discovered in 1975 by scientists at Eli Lilly & Co., who screened whole cell preparations of numerous bacterial and fungal cultures for those possessing catalytic activity toward the hydrolysis of a p-nitrobenzyl protected cephalosporin (3). A Bacillus subtilis culture (NRRL B8079) showed the highest catalytic activity toward two cephalosporin-derived pNB-protected substrates of all the cultures tested. Although the reaction yield was high, the enzyme activity was not sufficient to consider for industrial application.

A chromatographically pure solution of pNB esterase was isolated at Eli Lilly, and its amino acid sequence partially determined. Using this partial sequence, DNA primers were constructed and used to isolate and sequence the gene for pNB esterase. This gene was cloned into E. coli, where it was over-expressed to produce pNB esterase in large quantities (4). However, partially purified enzyme preparations of "pNB esterase" could not compete with the speed, economy, or the small reaction volumes (due to lack of solubility of substrate in the purely aqueous environments preferred by the enzyme) of the zinc-catalyzed deprotection reaction.

The targeted reaction substrates have changed over the fifteen year period as well. Cephalosporin-derived antibiotics continued to evolve from the first generation cephalexin (one of the two original cephalosporin substrates used to search for pNB esterase), second generation cefaclor, third generation cefixime, and fourth generation loracarbef. These antibiotics have been developed to be readily absorbed (generation one), more potent (generation two), much more potent (generation three), and, finally, immensely more stable in the body (generation four) (5). They all are synthesized using the pNB ester protecting group (6). In protected form, with perhaps the exception of cefixime, all are only sparingly soluble in water.

The pNB esterase enzyme has been further characterized (6). It is a water soluble, monomeric serine esterase of 54 kD molecular weight and a pI of 4.1. The enzyme is active on a variety of ester substrates, ranging from the cephalosporin-derived compounds on which it was screened to a number of simple organic esters. Reported $K_M$ values for cephalosporin-derived substrates are in 0.5 to 2 mM range. The enzyme functions best at temperatures below 50° C., and its pH optimum is between 8 and 9.

The pNB esterase still suffers from a problem common to a large number of enzyme reactions in the performance of synthetic chemistry: the desired substrates are only sparingly soluble in water, and the enzyme's catalytic ability is drastically reduced by even small quantities of water-miscible non-aqueous solvents.

It was discovered that substitution of amino acids at one or more specific amino acid positions resulted in the formation of enzymes having improved capabilities in aqueous and aqueous-organic media (43, 44). The specific amino acid position numbers at which substitutions were made to achieve these modified para-nitrobenzyl esterases were position Nos. 60, 94, 96, 144, 267, 271, 322, 334, 343, 358 and 370.

Specific amino acid substitutions have been disclosed which provide specific modified para-nitrobenzyl esterases having improved stability and/or ester hydrolysis activity in organic media (43, 44). The specific amino acid substitutions include Ile 60 Val, Ser 94 Gly, Asn 96 Ser, Leu 144 Met, Lys 267 Arg, Phe 271 Leu, His 322 Arg, Leu 334 Val, Leu 334 Ser, Ala 343 Val, Met 358 Val, and Tyr 370 Phe. One or more of these specific substitutions were found to increase the enzymatic activity and/or stability of the esterases in aqueous and aqueous-organic media. Ten specific modified para-nitrobenzyl esterases were disclosed which show enhanced activity in aqueous or aqueous-organic media over naturally occurring para-nitrobenzyl esterase. The amino acid sequences for these modified esterases are set forth in SEQ. ID. NOS. 4, 6, 8, 10, 12, 14, 16, 18, 20, and 22. These variants were identified as variants 1-1h9, 2-19e10, 3-10c4, 4-38b9, 4-43e7, 4-54b9, 2-13f3, 2-23e1, 4-53d5 and 5-1a12, respectively. The naturally occurring esterase is identified as O-Wtpnb or WT and is set forth in SEQ. ID. NO. 2.

Natural enzymes, such as pNB esterase, are poised on the brink of conformational instability, with native structures that walk a tightrope between large stabilizing and destabilizing forces. The molecular origins of enzyme stability are critical to understanding how proteins fold into their unique three-dimensional structures as well as to understanding the limits of (protein-based) life. Life on earth exists over a wide temperature range—nearly 200° C.—yet proteins isolated from organisms inhabiting the very coldest and hottest environments do not differ from one another in anything but the most subtle ways (28).

Enhancing the stability of enzymes is key to improving them for a wide range of applications, including catalysts in chemical processes and additives for laundry detergents. It has long been hoped that studies of naturally thermostable proteins would yield general rules that could be applied to stabilizing other, less-stable proteins. The extreme thermostability of many enzymes with significant half lives at high temperatures—even 100° C. and above—is often defined within their amino acid sequences rather than by extrinsic factors. Therefore the amino acid sequences and structures of enzymes from mesophilic organisms (i.e. optimal growth temperature ($T_{opt}$ approximately 20–50° C.) have been compared to those from thermophiles ($T_{opt}$ approximately 50–80° C.) and extreme thermophiles ($T_{opt}$ greater than or equal to 80° C.) in an effort to identify the interactions responsible for conferring enhanced thermostability (29; 30; 31). Numerous and intensive site-directed mutagenesis efforts have also probed this issue (32 and 33). Despite these efforts, considerable disagreement remains over which forces dominate thermostabilization mechanisms, and no generally-applicable rules for thermostabilizing proteins have been established. Some of the confusion arises from the large evolutionary distances that separate thermophilic enzymes from their mesophilic homologs. The relatively few mutations responsible for differences in thermostability are not easily identified in a background of many (often 100 or more) neutral mutations. Moreover, substantial increases in thermostability are often the result of multiple mutations, each of which makes a small but cumulative contribution. Another, more fundamental, reason is that the effects of temperature on the forces contributing to protein stability are many and highly complex (34). Any rules for engineering protein stability are likely to be protein-specific, and such efforts will need to be guided by detailed 3-dimensional structural information (35).

The design problem becomes even more challenging if improvements in thermostability are not to come at the cost of decreases in enzyme activity, particularly at reduced temperatures. It is widely believed that enhanced molecular rigidity is a prerequisite for thermostability, while maintaining flexibility is required for catalytic activity. The fact that natural thermophilic enzymes are active and stable at higher temperatures, but their activities at lower temperature are often compromised, has been used to support the idea that an improvement in one property (stability) will come at the cost of the other (activity) (33). An alternative explanation for the observation that natural proteins from thermophiles are less active than their mesophilic counterparts at the lower temperatures, however, is that natural selection has exerted pressure on one, but not both these properties. Because enzymes from a thermophile need not be active at low temperature, this property is free to drift. Thus the low activities of thermophilic enzymes at mesophilic temperatures may not necessarily mean that high activity is incompatible with high thermal stability.

In view of the above situation, there is a continuing need to develop new enzymes which have expanded catalytic capabilities. In particular, new thermostable enzymes are needed which can be used to provide ester cleavage for a variety of substrates and settings, including polar non-aqueous solvents.

SUMMARY OF THE INVENTION

In accordance with the present invention, modified para-nitrobenzyl esterases are provided which have improved thermal stability relative to the thermal stability of unmodified naturally occurring para-nitrobenzyl esterase. Unmodified para-nitrobenzyl esterase has an amino acid sequence which includes numbered positions ranging sequentially from 1 to 489 (SEQ. ID. NO. 2). Improved thermal stability is defined here as the ability of the variant pNB esterase to catalyze a reaction at higher temperatures than the wild type enzyme or to retain its activity longer than the wild type enzyme when subjected to heat.

As a feature of the present invention, it was discovered that amino acid substitutions at specific positions produced esterases having increased thermal stability. The specific amino acid positions at which substitutions increase thermal stability are 274, 313, 322, 343, 358, 370, 398, 412 and 437. Exemplary amino acid substitutions include Phe 274 Leu, Leu 313 Phe, His 322 Cys, His 322 Tyr, Ala 343 Val, Met 358 Val, Tyr 370 Phe, Gly 412 Glu and Ile 437 Tyr. The above substitutions can be made in addition to one or more of the substitutions mentioned in References 43 and 44 to provide especially useful modified para-nitrobenzyl esterases. Seven specific thermally stable variants were isolated. The amino acid sequences for these thermally stable variants are set forth in SEQ. ID. NOS: 26, 28, 30, 32, 34, 36 and 38. These variants are also identified throughout the specification as variants 1A5D1, 2A12, 3H5, 3G4, 5H3, 6H7 and 6sF9, respectively. These variants were all derived from the previously isolated variant identified as 2-19e10 (SEQ. ID. NO: 6) (43, 44).

As another feature of the present invention, a method is provided for isolating and identifying modified para-nitrobenzyl esterases which exhibit improved stability and/or esterase hydrolysis activity toward selected substrates and under selected reaction conditions relative to the unmodified para-nitrobenzyl esterase. The method involves preparing a library of modified para-nitrobenzyl esterase nucleic acid segments (genes) which have nucleotide sequences that differ from the nucleic acid segment which encodes for unmodified para-nitrobenzyl esterase. The library of modified para-nitrobenzyl nucleic acid segments is expressed to provide a plurality of modified enzymes. The clones expressing modified enzymes are then screened to identify which enzymes have improved esterase activity by measuring the ability of the enzymes to hydrolyze the selected substrate under selected reaction conditions and after incubation at elevated temperatures. Further modified variants can be produced by accumulating the beneficial mutations identified in this manner.

As an additional feature of the present invention, improvements in the catalytic activity of modified para-nitrobenzyl esterases after incubation at elevated temperatures with respect to a particular para-nitrobenzyl ester compound is determined by screening the modified enzymes with a substrate that is the para-nitrophenyl ester of the compound of interest. For example, screening of esterases for their ability to hydrolyze para-nitrobenzyl loracarbef is accomplished by screening the enzymes ability to hydrolyze para-nitrophenyl loracarbef at elevated temperatures. The use of a para-nitrophenyl ester as a screening substrate is especially well-suited for screening large numbers of modified esterases because enzymatic activity is easily measured due to the generation of a colored product, i.e. para-nitrophenol. The yellow colored para-nitrophenyl cleavage product is easily measured to provide an accurate measure of the modified esterase's ability to hydrolyze the specific para-nitrobenzyl ester compound. Further, the ability of the modified enzymes to hydrolyze a para-nitrophenyl ester is a good indication of the enzyme's ability to hydrolyze para-nitrobenzyl groups. This method allows the screening of large numbers of slightly different variations of enzymes which have been produced by random mutagenesis. This ability to easily screen large numbers of modified enzymes for their esterase activity increases the likelihood of identifying additional enzymes having increased activity at high temperatures in aqueous or aqueous-organic media and on other related substrates.

The above discussed and many other features and attendant advantages of the present invention will become better understood by reference to the following detailed description when taken in conjunction with the accompanying drawings.

BRIEF DESCRIPTION OF THE DRAWINGS

FIG. 1a shows the reaction wherein loracarbef nucleus-para-nitrobenzyl ester is hydrolyzed.

FIG. 1b shows the reaction wherein para-nitrophenyl acetate is hydrolyzed.

FIG. 1c shows the reaction wherein loracarbef nucleus-para-nitrophenyl ester is hydrolyzed.

FIGS. 3a–3o show the DNA sequence alignment of enzyme variants identified in accordance with the present invention as they align with naturally occurring para-nitrobenzyl esterase (O-Wtpnb). The variants are listed from top to bottom by generation. Boxed regions indicate DNA sequence regions where all variants are identical. The columns of DNA bases not boxed are those where at least one mutation in one of the variants has occurred.

FIGS. 4a–4e are the amino acid sequence alignment of the enzyme variants. The variants are listed from top to bottom by generation. The boxed regions indicate amino acid sequence regions where the variants are all identical with naturally occurring para-nitrobenzyl esterase. The columns of amino acids not boxed are those where at least one mutation in one of the variants has occurred.

FIG. 11 shows the formula for L-glutamine p-nitrobenzyl ester. FIGS. 11A and 11B show graphic results of HPLC measurement of the product of variant and wild type pNB esterase reaction on 1.0 mM L-glutamine p-nitrobenzyl ester in 1% DMF after a fixed reaction time. Enzymes were added to a 25° C. reaction solution consisting of 0.1 M PIPES (pH 7.0), 1% (FIG. 11A) or 20% (FIG. 11B) DMF.

FIGS. 19a–19j show nucleotide sequences for genes which encode thermostable esterases in accordance with the present invention. The consensus nucleotide sequence is also shown.

DETAILED DESCRIPTION OF THE INVENTION

In accordance with the present invention, a method of directed evolution is used to identify and isolate modified enzymes which have improved catalytic performance over naturally occurring para-nitrobenzyl (pNB) esterases at elevated temperatures. This technique relies on being able to screen a large number of slightly different variations (changes in the amino acid sequence) of the enzyme, and then to accumulate those sequence changes. Generating the variations in a random fashion utilizes random mutagenesis, and effective mutations are accumulated in sequential generations of mutagenesis and screening for the property of interest. The serine protease subtilisin, for example, has been evolved to be almost five hundred times more active than the naturally occurring enzyme in the presence of 60% dimethylformamide (DMF) (7, 8, 9). The present invention utilizes a related approach to identify and isolate pNB esterases which exhibit improved activity toward selected substrates, such as loracarbef-p-nitrobenzyl ester, and which exhibit improved activity elevated temperatures. Elevated temperatures are those above 50° C. and preferably between 50° C. and 80° C.

The method in accordance with the present invention which is used to identify and isolate modified esterases having improved activity at elevated temperatures includes three basic procedures. The first procedure involves the generation of large numbers of randomly mutated esterases. The second procedure involves screening the many mutated esterases to determine which ones exhibit increased catalytic activity towards selected substrates under specific reaction conditions. The third procedure involves accumulating further beneficial mutations in an 'evolved' or modified esterase. The generation of large numbers of randomly mutated esterases may be accomplished by any number of known protocols. The preferred procedure involves generating a library of modified esterase nucleic acid segments which have nucleotide sequences that differ from the nucleotide sequence of the naturally occurring or unmodified enzyme sequence. The library of mutated nucleotide sequences is then expressed in accordance with known methods for cloning and expression. The procedures for random nucleic acid mutagenesis and expression of the mutated nucleic acids is described in References 7, 8, 9, 43, 44 and in U.S. Pat. No. 5,316,935. Many other methods for random mutagenesis and expression are known, however, and can be implemented for this purpose.

Figure 1A:
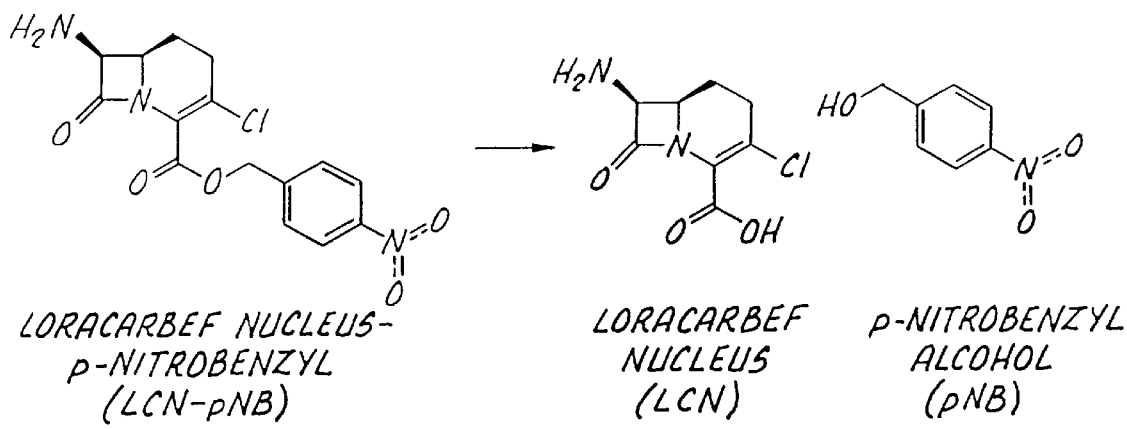
FIGS. 1a, 1b and 1c are diagrammatic representations of the substrates and products of reactions catalyzed by para-nitrobenzyl esterase and mutants or variants thereof.
Figure 1B:
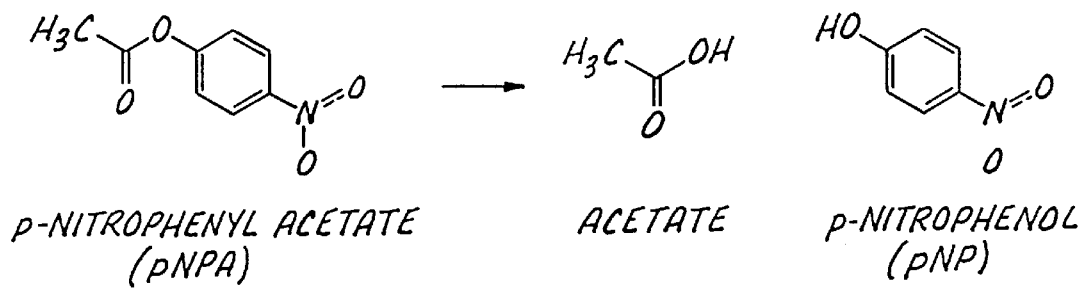
Figure 1C:
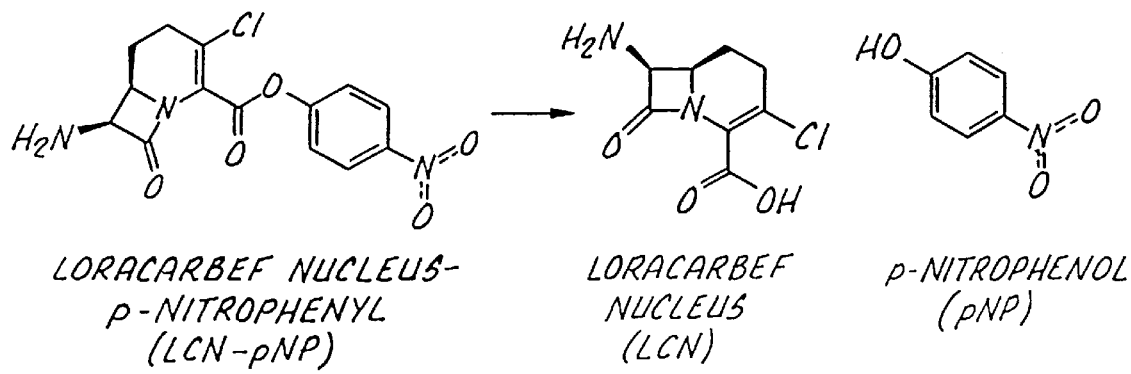

The screening of the amino acid sequences is accomplished by measuring the ability of the expressed enzymes to hydrolyze a selected substrate under selected reaction conditions. While screening can be performed directly on the desired substrate, the ease of screening can be greatly improved by using the p-nitrophenyl ester of the desired substrate. For example, if the compound of interest is loracarbef, then the p-nitrophenyl ester of the loracarbef is substituted for the p-nitrobenzyl ester (see FIG. 1c). If the sequence has the desired esterase enzyme activity, the para-nitrophenyl group will be cleaved from the substrate, as shown in FIG. 1c. The resulting free para-nitrophenol produces a yellow color in the reaction solution, which can be easily measured for both qualitative and quantitative evaluation of the amino acid sequences' performance as an esterase. This screening procedure is well-suited for evaluating the performance of modified para-nitrobenzyl esterases. This screening procedure may be used alone or in combination with the screening on the para-nitrobenzyl ester to provide confirmation of enzyme activity or to provide a more direct measurement of the ability of the amino acid sequences to catalyze p-nitrobenzyl ester cleavage for a particular compound. Other suitable nucleus compounds include other b-lactam antibiotics, peptides, peptide antibiotics (16), glycosylated peptides or amino acids (17, 18), peptides (19, 20, 21, 22, 23), natural amino acids (protected both at the C-terminus and/or acidic side chains) (21, 22, 24), non-natural amino acids (25), and other synthetic intermediates such as 2-aminobenzoate, 2-carbobenzoxyaminobenzoate (26), benzyloxycarbonyl-homoserine and benzyloxycarbonyl-O-diphenylphosphoryl-homoserine (27).

As employed herein, the term "stability," when used generally in reference to the stability of para-nitrobenzyl enzymes means the half-life of said enzyme when exposed to a particular set of reaction conditions, such as elevated temperature and/or organic media. When referring specifically to "stability" of the enzyme at elevated temperatures, the terms "thermal stability" or "thermostable" are used. In general, the higher the temperature to which the enzyme is exposed, the shorter the half-life of the enzyme (i.e., the shorter the enzyme retains its activity). Similarly, the greater levels of organic solvent to which said enzymes are exposed, the shorter the half-life of the enzyme. The phrase "catalytic activity" or simply "activity," means an increase in the $k_{cat}$ or a decrease in the $K_M$ for a given substrate, reflected in an increase in the $k_{cat}/K_M$ ratio. The above screening procedures may be conducted on a wide variety of substrates and under a wide variety of reaction conditions in order to establish the activity and/or stability of the amino acid sequences in different environments. For example, as disclosed in References 43 and 44 the reaction conditions can be varied from simple aqueous solutions to those containing varying amounts of organic solvents or other medium components. The amount of organic solvent or other medium components may be varied to any level. In accordance with the present invention, the temperature of the reaction can be varied in order to isolate variants with improved reaction rates and/or stabilities at different temperatures and/or the enzyme may be incubated at high temperatures prior to any reaction to measure their thermostability. Similarly, the pH of the reaction environment can be varied in order to optimize reaction rates and/or stabilities at different pH values. The reaction conditions may be varied widely in order to explore the limits of enzyme activity. The substrate can be varied in order to optimize the amino acid sequences for individual substrates or for specific combinations of substrates.

The above method was used to identify and isolate modified para-nitrobenzyl esterases which have improved ester hydrolysis activity toward several para-nitrobenzyl ester substrates in reaction solutions containing varying amounts of dimethylformamide ranging from 1 to 30 percent by volume (43, 44).

The naturally occurring para-nitrobenzyl esterase has an amino acid sequence which includes numbered position ranging from 1 to 489. The amino acid sequence for this enzyme is set forth in SEQ. ID. NO. 2 and FIG. 4. The nucleotide sequence which expresses the enzyme is set forth in SEQ. ID. NO. 1 and FIG. 3. It was discovered that substitution of amino acids at one or more of the positions numbered 60, 94, 96, 144, 267, 271, 322, 334, 343, 358, and 370 resulted in the production of an enzyme which exhibited increased activity toward various p-nitrobenzyl ester substrates in purely aqueous solutions and solutions containing a polar organic solvent, i.e. dimethylformamide (43, 44). In accordance with the present invention, it was further discovered that substitutions at positions 274, 313, 398, 412 and 437 resulted in increased thermal stability. Substitutions at positions 322, 343, 358 and 370 were found to provide both increased activity in solutions containing polar organic solvents and improved thermal stability. Any number of different amino acids may be substituted at the various identified positions with a large number of different combinations being possible where substitutions at one or more positions is accomplished. The preferred amino acid substitutions are set forth below in Table 1.

TABLE 1

| Amino Acid Position | Substitution | Abbreviation |
|---|---|---|
| 60 | Ile → Val | Ile 60 Val |
| 94 | Ser → Gly | Ser 94 Gly |
| 96 | Asn → Ser | Asn 96 Ser |
| 144 | Leu → Met | Leu 144 Met |
| 267 | Lys → Arg | Lys 267 Arg |
| 271 | Phe → Leu | Phe 271 Leu |
| 274 | Phe → Leu | Phe 274 Leu |
| 313 | Leu → Phe | Leu 313 Phe |
| 322 | His → Arg | His 322 Arg |
| 322 | His → Cys | His 322 Cys |
| 322 | His → Tyr | His 322 Tyr |
| 334 | Leu → Val | Leu 334 Val |
| 334 | Leu → Ser | Leu 334 Ser |
| 343 | Ala → Val | Ala 343 Val |
| 358 | Met → Val | Met 358 Val |
| 370 | Tyr → Phe | Tyr 370 Phe |
| 398 | Phe → Phe | Phe 398 Phe |
| 412 | Gly → Glu | Gly 412 Glu |
| 437 | Ile → Thr | Ile 437 Thr |

In accordance with the present invention, the modified esterase must have substitutions at one or more of the positions found to provide increased thermal stability, i.e. positions 274, 313, 322, 343, 358, 370, 398, 412 and 437. In addition, the modified esterase may include additional substitutions at one or more of the positions which provide increased activity in organic solution, i.e. positions 60, 94, 96, 144, 267, 271 and 334.

Modified esterases which contain one or more of the substitutions set forth in Table 1 are set forth in FIG. 4 and SEQ. ID. NOS. 4, 6, 8, 10, 12, 14, 16, 18, 20, 22, 26, 28, 30, 32, 34, 36 and 38. The consensus amino acid sequence is set forth in SEQ. ID. NO: 24. The nucleotide sequences which expressed the modified enzymes is set forth in FIG. 3 and SEQ. ID. NOS. 3, 5, 7, 9, 11, 13, 15, 17, 19, 21, 25, 27, 29, 31, 35 and 37, respectively. The consensus nucleotide sequence is set forth in SEQ. ID. NO: 23. The procedure for isolating and identifying these enzymes is set forth in the examples below. Isolates with SEQ. ID. NOS: 4, 6, 8, 10, 12, 14, 16, 18, 20 and 22 have enhanced activity in organic media, and they also have increased thermal stability. Any of these isolates may be further modified by substitutions at positions 274, 313, 398, 412 or 437 to provide preferred thermally stable isolates. Exemplary thermally stable isolates which were derived from the 2-19e10 variant (SEQ. ID. NO: 6) have SEQ. ID NOS: 26, 28, 30, 32, 34, 36 and 38. These isolates were shown to be more thermally stable than wild type pNB. Other thermally stable isolates may be prepared by starting with any of the other above-listed modified esterases which have increased activity in organic media. When activity in organic media is not required, the substitutions which provide activity in organic media may be deleted.

In the following examples, the procedures used to prepare a group of esterases with enhanced activity in organic media are first set forth. This procedure is the same as disclosed in Refs. 43 and 44. Then, one of these esterases (2-19e10–SEQ. ID. NO: 6) is further subjected to directed evolution in accordance with the present invention to provide an exemplary group of preferred esterases which have enhanced activity both in organic media and at high temperatures. As is apparent, any of the initially isolated modified esterases which are active in organic media can be used to prepare a wide variety of other high temperature variants.

EXAMPLES OF PRACTICE

Directed Evolution of Esterases with Enhanced Activity in Organic Media

Introduction

Loracarbef (LCN) is a cephalosporin-derived antibiotic marketed in modified form under the trade name LORABID. The production of loracarbef is different from many traditional antibiotics in that it is synthesized chemically with no microbial fermentation steps. This ensures that the antibiotic is free from any microbially-produced toxins generated during fermentation. While the functional antibiotic requires a free carboxylic acid moiety, the free carboxylic acid creates problems synthetically. Synthesis of loracarbef has therefore been designed to protect the carboxylic acid through an ester linkage with pNB alcohol. The pNB esterase enzyme is expected to catalyze the deprotection, that is hydrolyze the pNB ester, toward the end of the chemical synthesis. This reaction is shown in FIG. 1a. In addition to protecting the carboxylic acid, the ester-linked pNB group makes the resulting compound virtually insoluble in water.

In designing a method which directs the evolution of an enzyme towards activity and specificity on a given substrate, several important parameters require consideration. One such parameter arises from examining the frequency with which enzyme variants with enhanced performance on the desired substrate arise as a result of random mutagenesis. Nature has demonstrated repeatedly that most variations in an enzyme's amino acid sequence either do not alter the enzyme's structure or function or are deleterious. This suggests that a large number of variants need to be examined to find a variant more effective at performing the desired ester hydrolysis in FIG. 1a. A rapid procedure is required to screen large numbers of enzyme variants. Colorimetric assays are most often optimal in this regard. The reaction in FIG. 1a is problematic for rapid screening of activity because the absorbance spectra of the reactant and the two products are very similar. In addition, the reactant and products do not absorb in the visible region, making the rapid assaying of activity difficult.

Para-nitrophenyl acetate (pNPA) is a general esterase substrate. The enzyme-catalyzed hydrolysis reaction is shown in FIG. 1b. Use of the pNPA substrate solves the absorbance problem, as the nitrophenol product is yellow while the other reaction components are colorless. The ability of the alcohol oxygen to form resonance structures which participate in conjugation with the phenyl ring gives rise to the yellow color. Lowering the pH below 6.5 severely shifts the resonance structure away from the conjugation and eliminates the yellow color associated with nitrophenol solutions. The ability to form resonance structures also makes nitrophenol an excellent leaving group, as demonstrated by pNPA's gradual hydrolysis in buffer alone. This spontaneous hydrolysis accelerates with increasing pH, and at pH values above 8.5 occurs almost immediately. The pNPA substrate is also membrane permeable. This substrate is hydrolyzed rapidly by whole E. coli cells expressing pNB esterase intracellularly. The same cells, but without the expression plasmid, do not catalyze the conversion. This substrate is sterically and chemically different from the LCN-pNB substrate, however, and as such is not the most preferred choice for directing the evolution of the esterase toward activity on LCN-pNB. It does however, allow for optimization of enzyme expression in new bacterial hosts, where the increase in amount of enzyme produced translates into increased activity during screening.

In order to optimize generation of enzymes with improved activity toward the LCN-pNB substrate, a preferred alternate or supplemental substrate is utilized which includes the p-nitrophenyl chromophore from the pNPA substrate and as much of the loracarbef nucleus as possible. This substrate is the LCN-pNP substrate whose structure and reaction are shown in FIG. 1c. This substrate is membrane permeable, obviating the need for cell lysis during screening. The use of LCN-pNP during screening may result in an enzyme with high hydrolytic activity toward LCN-pNP, but not toward LCN-pNB. The validity of this screening approach was therefore verified by comparing the activities of nearly 70 pNB esterase variants on these two substrates.

A second parameter in directed evolution experiments is the choice of reaction conditions used during screening. The more the screening conditions differ from the desired reaction conditions, the more likely that variants found to have a positive effect in screening will not exhibit improved performance in the desired reaction conditions. Therefore the reaction conditions used for screening should mimic as closely as possible the ultimate desired reaction conditions (temperature, pH, solvent, substrate concentration, reaction time, etc.).

Screening of Variants

The screen consisted of resuspending individual colonies of bacteria in a small volume of buffer and measuring the turbidity of the bacterial suspension using a spectrophotometer in order to estimate the cell concentration in the buffered solution. A small volume of this bacterial suspension was added to a buffered solution containing a pNP ester-substrate, and the release of product is measured by following the formation of yellow color. The rate of product appearance was normalized to the cell concentration by the turbidity measurement. This is indicative of enzyme activity per bacterium; those colonies which generated higher activity to turbidity ratios were retested. The variant pNB esterases contained within the best clones were then purified and tested on the screening substrate (i.e. LCN-pNP) to determine the extent of improvement and on the desired pNB ester to further determine and confirm that the improvement applies to the substrate of ultimate interest.

Introduction of Random Mutations

The method of the present invention for directing the evolution of pNB esterase involves making a large library of pNB esterase genes, each with a small number of random, or nearly random, alterations in the 1500 base pair DNA sequence which codes for the pNB esterase. This collection of DNA sequences is then placed into E. coli, which translates the DNA sequences into the different amino acid sequences. Because the DNA sequence has been altered slightly, the amino acid sequence of the enzyme may be altered. The LCN-pNP and/or pNPA substrates are then used to screen out those E. coli that are producing an enzyme which appears to outperform the original. The best performer is then used to repeat this sequence of events, in multiple generations, until the desired performance goal is achieved. DNA sequence analysis of the improved enzymes provides identification of the amino acid substitutions responsible for the observed activity enhancements.

The number of random alterations introduced in the 1500 base pair sequence (substitution frequency) is a third important design parameter in directed evolution methods. If the frequency of alterations is too high, most of the enzymes produced will be inactive. If the frequency of alterations is too low, most of the DNA base substitutions produced will be an exact copy of the original DNA sequence, and the resulting enzymes will not be any different than the original. Because approximately one-third of the altered DNA sequences lead to the same amino acid sequence in a protein, the preferred number of DNA alterations per gene is greater than one. At one alteration or less per sequence, much of the DNA produced will produce exact copies of the original protein sequence, and a substantial portion of the screening effort will be spent searching through copies of the original enzyme. At more than than three alterations per sequence, on average more than two amino acid alterations per enzyme are being produced. The enzyme's activity is a function of all the alterations contained within; the activity becomes a competition between the rare alterations which are beneficial and the less rare alterations which are deleterious (7). The preferred number of alterations is therefore greater than one and not too much larger than three.

The substitution frequency is calculated as the number of substitutions made in a given sequence divided by the number of possible sites for substitution and is usually expressed as a percentage (or fractional substitution). Thus the substitution frequency required to generate one to three substitutions per gene depends on the sequence length of the DNA coding for the enzyme (or the length of the DNA sequence targeted for random mutagenesis, if smaller). Polymerase chain reaction (PCR) conditions which generate substitution rates from 0.25 to 20 substitutions per 1000 base pairs have been characterized (10, 11 and 12).

This above method, as exemplified in the following examples, can be used to direct the evolution of pNB esterase's ability to better catalyze a desired reaction. Evolution also implies accumulating improvements in activity over several generations, and this process is repeated multiple times, each time beginning with the best variant from the previous generation. A large library of genes each containing a small number DNA substitutions are generated using error-prone PCR techniques. This library is placed in E. coli, where it is translated from DNA to enzyme. The enzyme library is screened for those enzymes which outperform the original. The best new enzyme then becomes the original as the process is repeated until a desired result is achieved.

Purification of Enzymes

The purification of enzymes was accomplished by using a modification of the scheme which includes a pH precipitation, an ammonium sulfate fractionation and three chromatographic steps (6 and 4). The usual three chromatographic steps were reduced to two by replacing a dye affinity column and an ion exchange column with a single (IDA-$Cu^{2+}$) metal affinity column (IMAC). The wild type pNB esterase open reading frame contains 12 histidines, which are the amino acid residues generally responsible for retention on a metal affinity column (13). Although the surface accessibility of these histidines is unknown, the elution of pNB esterase at 4–5 mM imidazole in an imidazole gradient is consistent with one or two histidine interactions with the chromatographic support (14).

After the enzyme samples were exchanged into Tris buffer, pH 7.0, the enzyme concentrations were measured. As evidenced by SDS-PAGE, the purity of pNB esterase (estimated to be at least 95%) is not compromised by replacing the two chromatographic steps with one IMAC column. In addition to removing a chromatographic step, this replacement also conveniently removed the need for dialysis between columns, as the high salt content after the first ion exchange column does not affect the performance of the metal affinity column. Dialysis was performed only after separation on the metal affinity column.

Homology Studies

A homology search of the major protein data bases (Protein Information Resource, Swiss Protein, translated GenBank, and Protein Data Bank) revealed that pNB esterase shares significant homology with a number of known esterases. Eleven of the most similar enzymes, representing seven distinct classes of esterases, were chosen for sequence comparisons with pNB esterase. These enzymes, their EC classification, the organism from which they were isolated, and their percent identity and similarity to pNB esterase are listed in Table 2. The enzymes were identified using a BLAST search of the PDB, PIR, SWISS-PROT, and translated GenBank databases. Percent (%) identity and % similarity were determined using the BEST-FIT tool in the GCG software package.

TABLE 2

Comparison of amino acid sequence between pNB esterase and esterases isolated from various organisms

| Enzyme | Code | Species | % Identity | % Similarity | Reference |
|---|---|---|---|---|---|
| Acetylcholinesterase | EC3.1.1.7. | Torpedo californica | 32.5 | 53.7 | 16 |
|  |  | Oryctolagus cuniculus | 36.0 | 58.3 | 17 |
| Butyrylcholinesterase | EC3.1.1.8. | Oryctolagus cuniculus | 35.0 | 56.7 | 18 |
| Carboxylesterase | EC3.1.1.1. | Oryctolagus cuniculus | 36.7 | 57.2 | 19 |
|  |  | Homo sapiens | 37.2 | 58.6 | 20 |
|  |  | Dictyostelium discoideum | 34.4 | 55.5 | 21 |
| Thioesterase | EC3.1.2.14. | Anas platyrhynchos | 38.7 | 58.3 | 22 |
| Triacylglycerol lipase | EC3.1.1.3. | Geotrichum candidum | 30.4 | 48.6 | 23 |
|  |  | Candida rugosa | 29.1 | 49.5 | 24 |
| Cholesterol esterase | EC3.1.1.13. | Candida rugosa | 29.6 | 49.8 | 25 |
| Carbamate hydrolase | EC3.1.1.-. | Anthrobacter oxidans | 34.0 | 56.8 | 15 |

The cholinesterases are important in neurotransmission, carboxyl- and thioesterases are digestive enzymes, lipases and cholesterol esterases work on degrading lipid components. Carbamate hydrolase was discovered in the same way pNB esterase was discovered: screening for an enzyme with activity on a desired substrate, phenmedipham, an herbicide carbamate (15). Carbamates are structurally similar to esters, containing a nitrogen linkage not present in esters (R—N—COO—R' vs. R—C—COO—R'), and are known to inhibit esterases. This degradative activity was discovered in an *Arthrobacter oxidans* strain from soil samples of phenmedipham-treated fields. Starting from enzymes such as these, the method of the present invention can be used to prepare and isolate groups of modified esterases or carbamate hydrolases which have improved activity over other naturally occurring enzymes, such as those listed in Table 2.

Some of the esterases in this group of homologous enzymes are noted for the feature of substrate inhibition at high substrate concentration. In particular, substrate inhibition has been a well-noted feature of acetylcholinesterase analysis. While the mechanism of inhibition is not clear, people have chosen to model the inhibition using the premise that the substrate can bind at two locations within the enzyme, and do so with different binding constants. Butyrylcholinesterase does not share this inhibition, and this fact is often used to distinguish the two cholinesterases. Studies have determined some of the residues responsible for this behavior by altering acetylcholinesterase residues to the appropriate butyrylcholinesterase residues and examining the inhibitory behavior. The fact that the inhibition characteristics can be altered by substitution shows that enzyme variants of the above types of enzymes, which are not inhibited by substrate, can be produced by the method of the present invention involving random mutagenesis and screening in high concentrations of substrate for enhanced activity.

Random Mutagenesis of pNB Esterase by Error-Prone PCR

The pNB esterase gene in the pNB106R expression plasmid is flanked by the restriction site Xba I 51 base pairs prior to the start of the open reading frame and by the restriction site Bam HI 313 base pairs after the stop codon of the open reading frame (4). Small, single-stranded DNA primers were synthesized to complement regions 25 base pairs upstream of the Xba I site (forward primer) and 143 base pairs downstream of the Bam HI site (reverse primer). The locations of these primers were chosen because the DNA between the two primers is the region that will be altered and amplified during the mutagenic polymerase chain reaction (error-prone PCR). The error-prone PCR conditions used were based on the requirements that the substitution frequency be between one and three substitutions per thousand bases (1.5 to 4.5 substitutions per gene) (10). Changes in any part of the open reading frame resulting in enhanced activity are useful. Therefore the whole open reading frame was given the opportunity to be altered by the mutagenesis. Additionally, once the DNA is amplified and mutagenized, it must be inserted into a circular DNA plasmid. By cutting the amplified DNA with the restriction enzymes Xba I and Bam HI, the ends of this insert are properly prepared to ligate to the plasmid. Finally, the primers are located far enough outside of the restriction sites that the small pieces of DNA liberated when the insert is cut by Xba I and Bam HI were visible by standard gel electrophoresis techniques. This ensures that the cutting step has occurred properly, should the ligation perform poorly.

Screening and Analysis of pNB Esterase Variants

An initial round of error prone PCR was performed to produce substitutions within the pNB esterase gene. The resulting DNA product was cloned into the expression vector and expressed in E. coli. One thousand of the resulting colonies were screened for esterase activity on the pNPA substrate (FIG. 1B) in 20% DMF in 96 well plates (experimental details are given in Materials and Methods section below). Of the 1000 colonies selected, thirty-three were rescreened as potential positive variants. The three colonies with the highest activity to cell density (turbidity) ratio were grown, along with the wild type pNB esterase, in 1 liter cultures, and the pNB esterase variants were partially purified using the precipitation, ammonium sulfate fractionation, and a single DE-52 ion exchange column (6). These partially purified enzymes were then assayed along with wild type control for their hydrolytic activity toward the pNPA and LCN-pNB substrates.

All the variants showed higher total activity than wild type pNB esterase on the pNPA substrate, while only one, 1-1H9 (SEQ. ID. NO. 4), showed a significant increase in total activity on the targeted LCN-pNB substrate (1H9 indicates the variant designation; the initial 1-indicates round or generation number. This should be read "variant 1H9 of generation 1.") All variant designations in this specification follow this format. This variant was therefore used as the parent for the second generation of mutagenesis and screening.

Figure 5A:
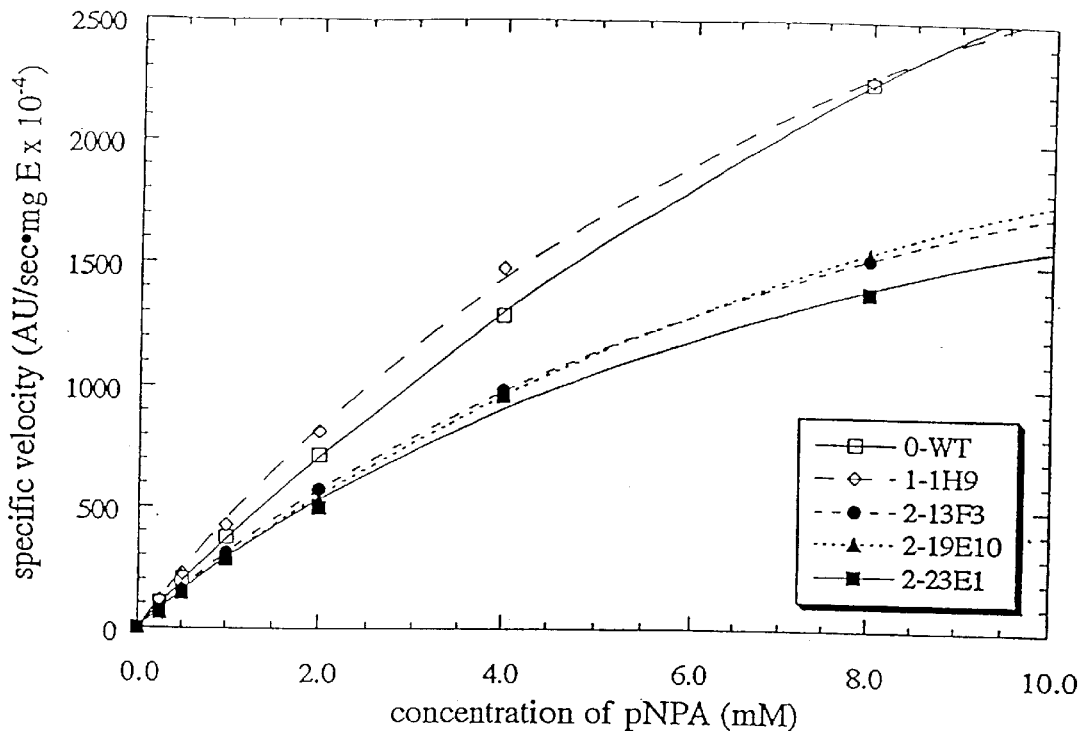
FIG. 5a shows variant and wild type pNB reaction kinetics on p-nitrophenyl acetate (pNPA) in 15% dimethylformamide (DMF). Enzymes were added to a 30° C. reaction solution consisting of 0.1 M Tris-HCl (pH 7.0), 15% DMF, and varying concentrations of pNPA.
Figure 5B:
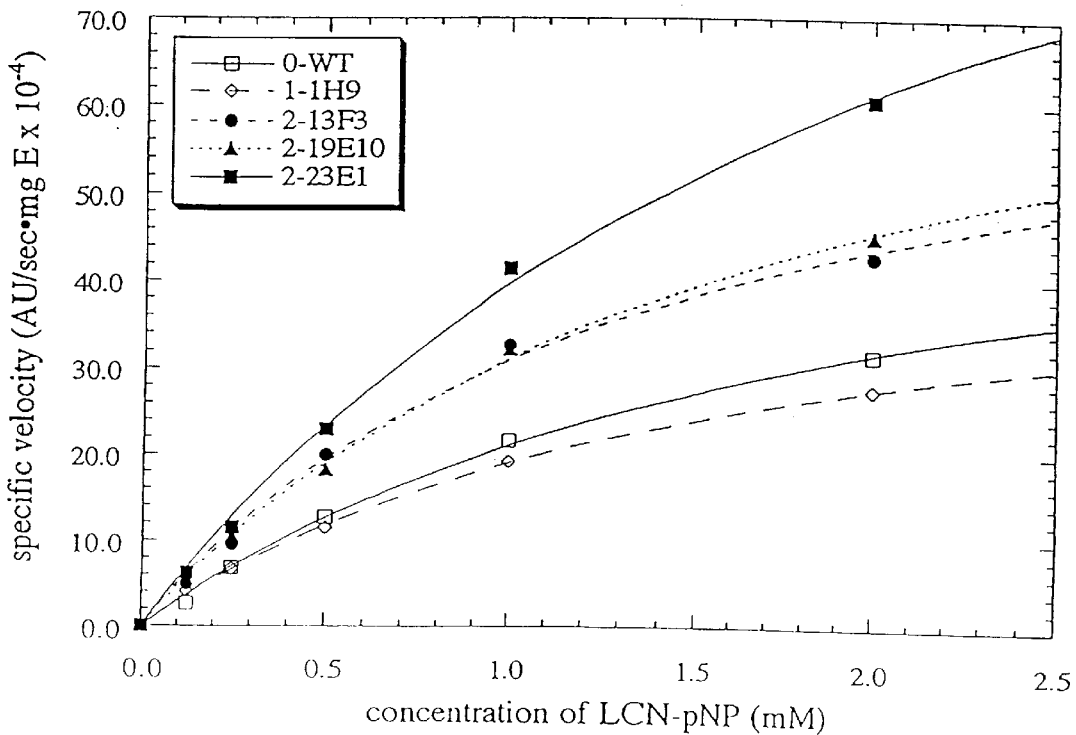
FIG. 5b is a plot of variant and wild type pNB esterase reaction kinetics on p-nitrophenyl loracarbef nucleus (LCN-pNP) in 15% dimethylformamide (DMF). Enzymes were added to a 30° C. reaction solution consisting of 0.1 M Tris-HCl (pH 7.0), 15% DMF, and varying concentrations of LCN-pNP.
Figure 5C:
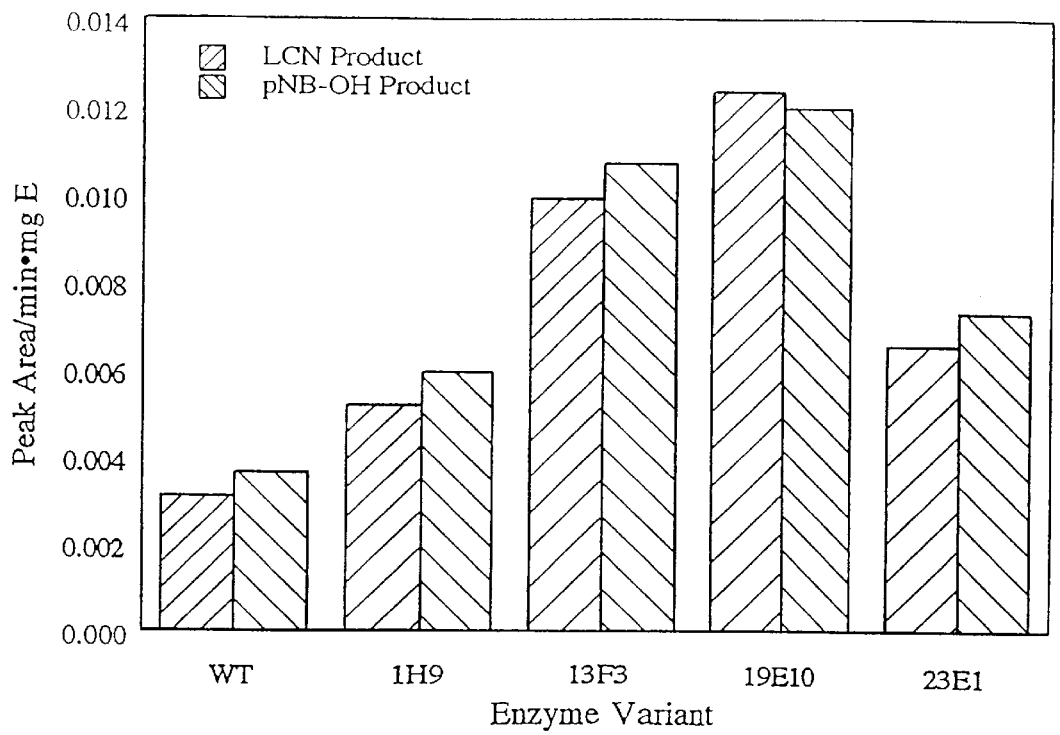
FIG. 5c shows graphic results of hydrolysis product formation, as measured by HPLC, by variant and wild type pNB esterases on 1.0 mM p-nitrobenzyl loracarbef nucleus (LCN-pNB) in 15% DMF. Enzymes were added to a 30° C. reaction solution consisting of 0.1 mM Tris-HCl (pH 7.0), 15% DMF, and 1.0 mM LCN-pNB.

The second generation of the directed evolution process began with error-prone PCR on the gene isolated from variant 1-1H9. 2800 colonies were screened in 96 well plates, this time using the hybrid LCN-pNP substrate and 15% DMF. From these, 65 colonies were rescreened as potential positive variants, and again the best three were grown in 1 liter cultures along with the wild type and the 1-1H9 parent. The modified pNB esterases (2-13F3—SEQ. ID. NO. 16; 2-19E10—SEQ. ID. NO. 6; and 2-23E1—SEQ. ID. NO. 18; 1-1H9—SEQ. ID. NO. 4) and wild type—SEQ. ID. NO. 2 from these colonies were purified and assayed on all three ester substrates (pNPA, LCN-pNP, and LCN-pNB), with the results shown in FIGS. 5a, 5b and 5c. While the second round variants had lost some of their ability to hydrolyze pNPA, all three exhibited increased activity on LCN-pNP. For two second round variants, 2-13F3 and 2-19E10, the increase in activity also applied to the p-nitrobenzyl substrate, LCN-pNB. 2-23E1, the variant showing the most activity on LCN-pNP, did not show marked improvement on LCN-pNB. Because 2-19E10 showed slightly better performance characteristics on LCN-pNB, it was used for the third round of mutagenesis.

Figure 6:
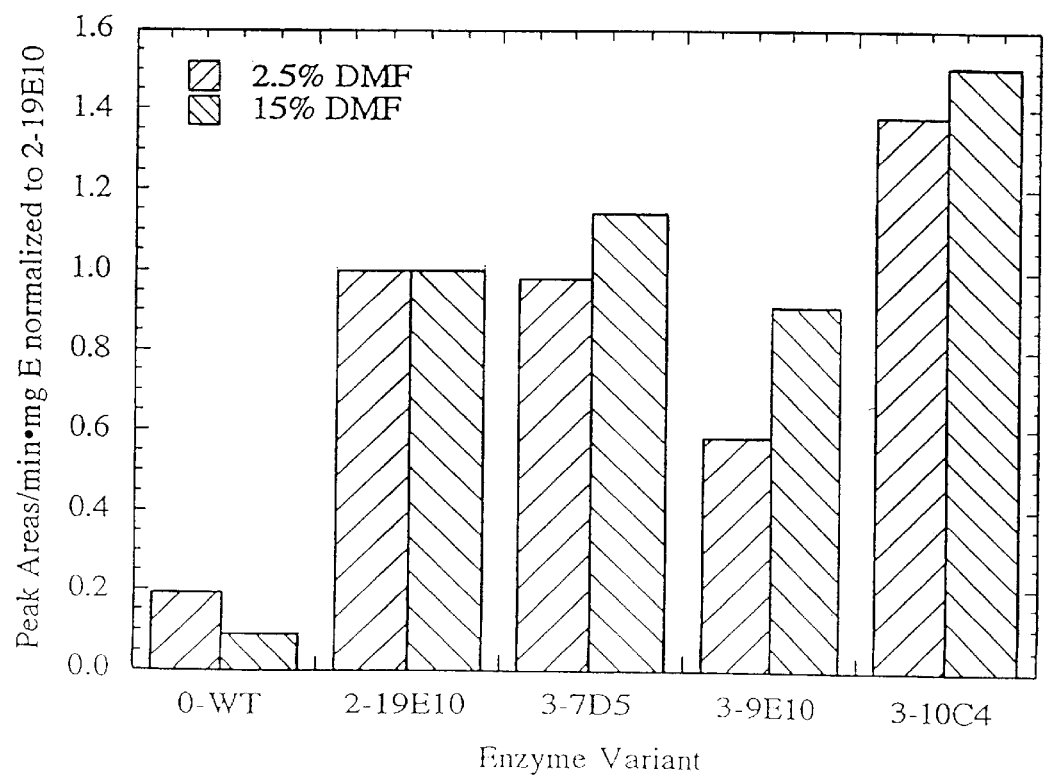
FIG. 6 shows hydrolysis product formation, as measured by HPLC, of variant and wild type pNB esterases on 0.25 mM p-nitrobenzyl loracarbef nucleus (LCN-pNB) in 2.5 and 15% dimethylformamide (DMF) at 30° C. The resulting peak areas were normalized to that of the parent of generation three, 2-19E10 (SEQ. ID. NO: 6).

Screening of the third round of mutagenesis involved examination of 1500 colonies using the LCN-pNP substrate and 20% DMF. Forty were rescreened as potential positive variants. The three best (3-7D5, 3-9E10, and 3-10C4—SEQ. ID. NO. 8) were then grown in 500 mL cultures, and the enzymes were purified. Of these three showing best activity on LCN-pNP, only 3-10C4 showed increased activity on LCN-pNB as demonstrated in FIG. 6. 3-10C4 shows a 40% improvement in activity over 2-19E10 in 2.5% DMF and a 50% improvement in 15% DMF.

Figure 7A:
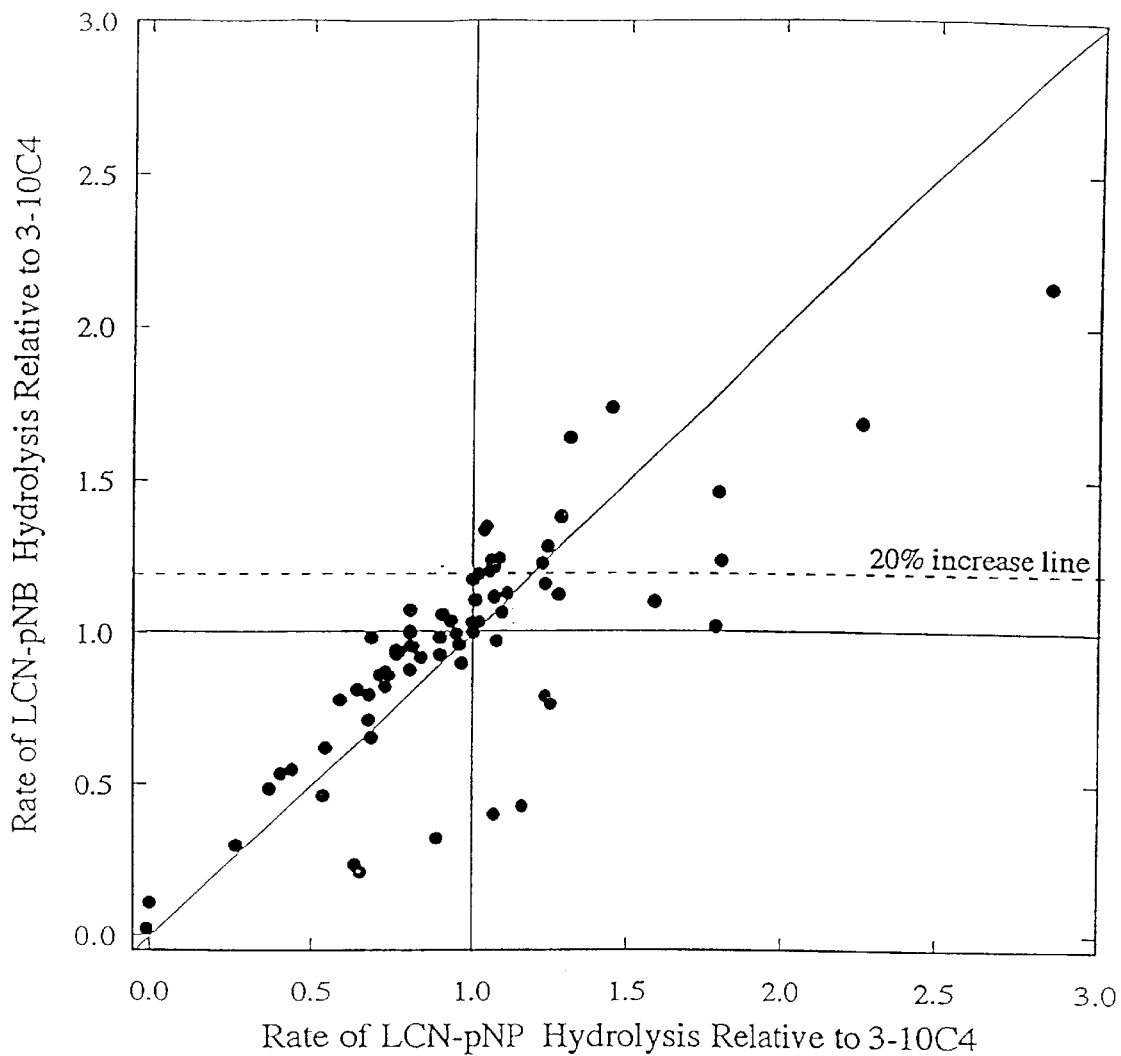
FIG. 7a is a plot of hydrolysis rates of fourth generation variants on the LCN-pNP and LCN-pNB substrates. The rates are normalized to those of the third generation variant 3-10C4 (SEQ. ID. NO: 8). After an 8 hour induction period, whole cell screening assays were performed at 25° C. in a 0.1 mM Tris-HCl (pH 7.0), 15% dimethylformamide reaction solution containing 0.8 mM of either p-nitrophenyl loracarbef nucleus (LCN-pNP) or (LCN-pNB).

The fourth round of mutagenesis and screening examined 7400 colonies using LCN-pNP substrate and 20% DMF. Of these, 250 were rescreened as potential positives. Sixty-four of those either most active in 5% DMF, most active in 20% DMF, or the best ratio of activities in 20% to 5% DMF were further screened along with wild type, 1-1H9, 2-19E10, and 3-10C4 on LCN-pNB. The screening results on both LCN-pNP and LCN-pNB were normalized to the activity of the parent 3-10C4 and are shown in FIG. 7a. Of the sixty-four colonies chosen, five show activity increases of 50% or more over 3-10C4, and sixteen show increases of greater than 20% over 3-10C4. The best five variants were determined based on the ability to hydrolyze the substrate LCN-pNB only. The best variant, with over a 2-fold improvement on 3-10C4, was 4-54B9 (SEQ. ID. NO. 14). The remaining four variants all demonstrated approximately 60–65% improvement over 3-10C4; these variants were labeled 4-38B9 (SEQ. ID. NO. 10), 4-43E7 (SEQ. ID. NO. 12), 4-53D5 (SEQ. ID. NO. 20) and 4-73B4 (later found to be identical to 4-38B9).

A measure of how well the activity of these enzymes on the screening pNP substrate relates to activity on the pNB substrate was established (FIG. 7a). The overall trend demonstrates a good correlation between activities on the screening pNP and actual pNB substrates, although the distribution is skewed slightly toward the screening substrate, as demonstrated by the trend of data points to lie below the forty-five degree line. If increases in activity on one substrate correlated exactly with increases in activity on the other, then all the points would lie exactly on the 45-degree line. The strength of this correlation is an important measure of the validity of the screening strategy in accordance with the present invention. This graph shows that the screening strategy premise that the structurally similar LCN-pNP can successfully replace LCN-pNB, the hydrolysis of which is difficult to measure. Contrast this with the pNPA substrate, whose structure does not mimic the desired loracarbef substrate. Modified pNB esterase activities on pNPA do not correlate as well with activity on the loracarbef substrates.

Figure 7B:
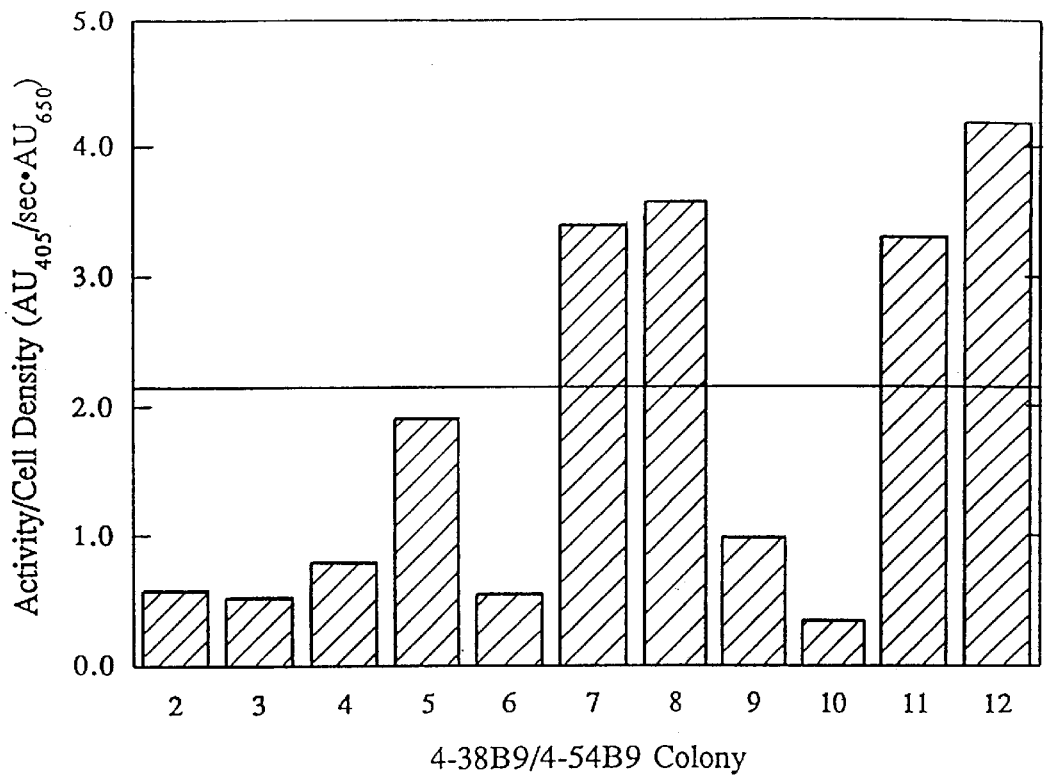
FIG. 7b shows graphic results of the screening activity of the ligation mixture 4-38B9 and 4-54B9. The horizontal line indicates the activity of the most active fourth round variant, 4-54B9. Colony 12, which exhibits an approximate 2-fold improvement in activity, corresponds to pNB esterase variant 5-1A12.

To demonstrate the utility of recombining beneficial mutations in the production of improved pNB esterases, a small, biased library of fifth generation variants was generated by recombining the genes from the fourth generation variants by restriction and re-ligation. The genes from the five variants from the fourth generation were individually restricted by Xho I, a restriction enzyme which cuts in the center of this gene. The DNA fragments were mixed with the DNA fragments from 4-54B9, the variant which appeared to outperform all others from the fourth generation, in pairwise fashion (e.g. one tube contained the fragments from 4-38B9 and 4-54B9, another tube contained fragments from 4-43E7 and 4-54B9, etc.). These mixtures of DNA fragments were each ligated simultaneously with the expression plasmid, transformed into *E. coli*, and assayed on LCN-pNP substrate in 20% DMF. The results from screening colonies expressing the recombined genes are shown in FIG. 7b. Of the four sets of ligations performed, only the mixture ligating 4-54B9 with 4-38B9 resulted in an enhancement in activity over 4-54B9. According to the screening data, this combination of mutations (labeled 5-1A12—SEQ. ID. NO. 22) displays approximately twice the activity of 4-54B9. This demonstrates that positive mutations can be combined for additional beneficial effects. Further beneficial combinations of mutations can be found by combining mutations using this or other random DNA recombination methods or by site-directed mutagenesis, once the DNA sequences are determined.

Kinetic Characterization of Evolved pNB Esterases

Figure 8A:
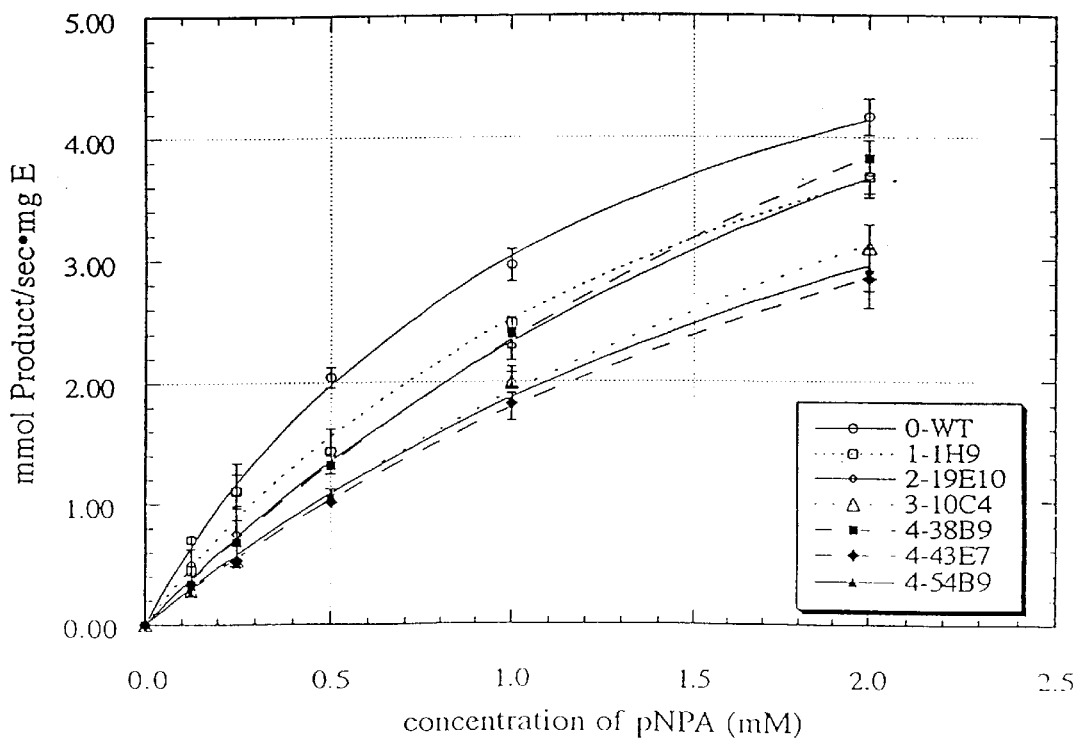
FIG. 8a is a plot of variant and wild type pNB esterase reaction kinetics on pNPA in aqueous buffer (0% dimethylformamide). Enzymes were added to a 30° C. reaction solution consisting of 0.1 M PIPES (pH 7.0) and varying concentrations of pNPA.
Figure 8B:
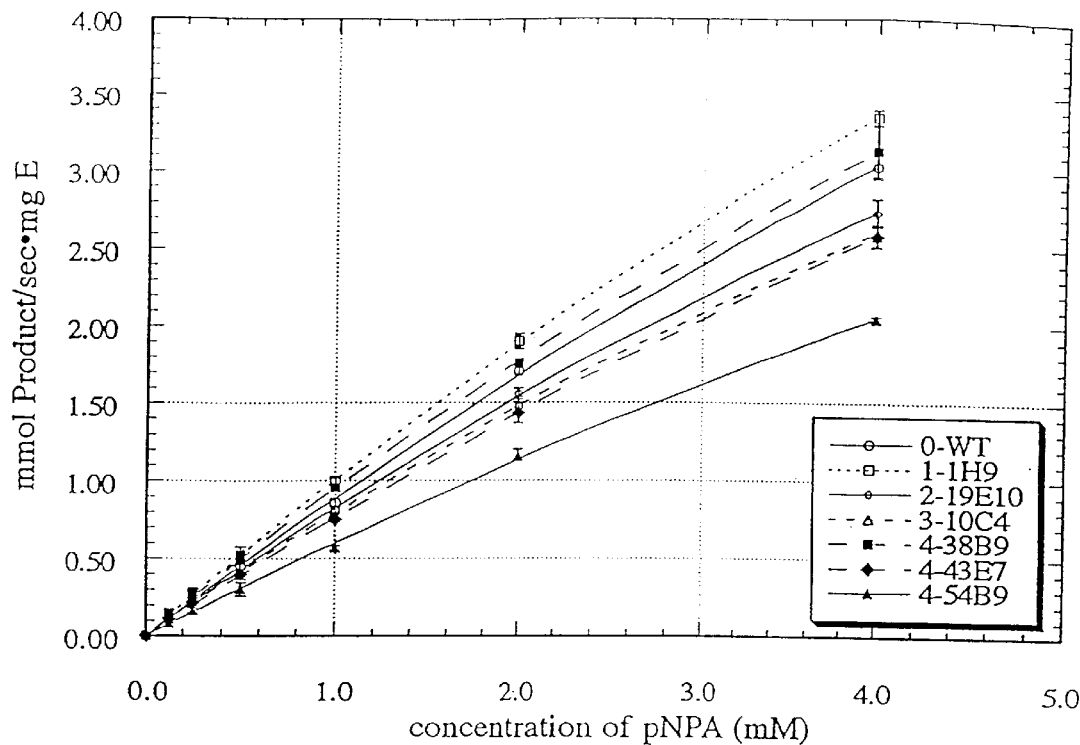
FIG. 8b is a plot of variant and wild type pNB esterase reaction kinetics on pNPA in 15% DMF. Enzymes were added to a 30° C. reaction solution consisting of 0.1 M PIPES (pH 7.0), 15% DMF, and varying concentrations of pNPA.
Figure 8C:
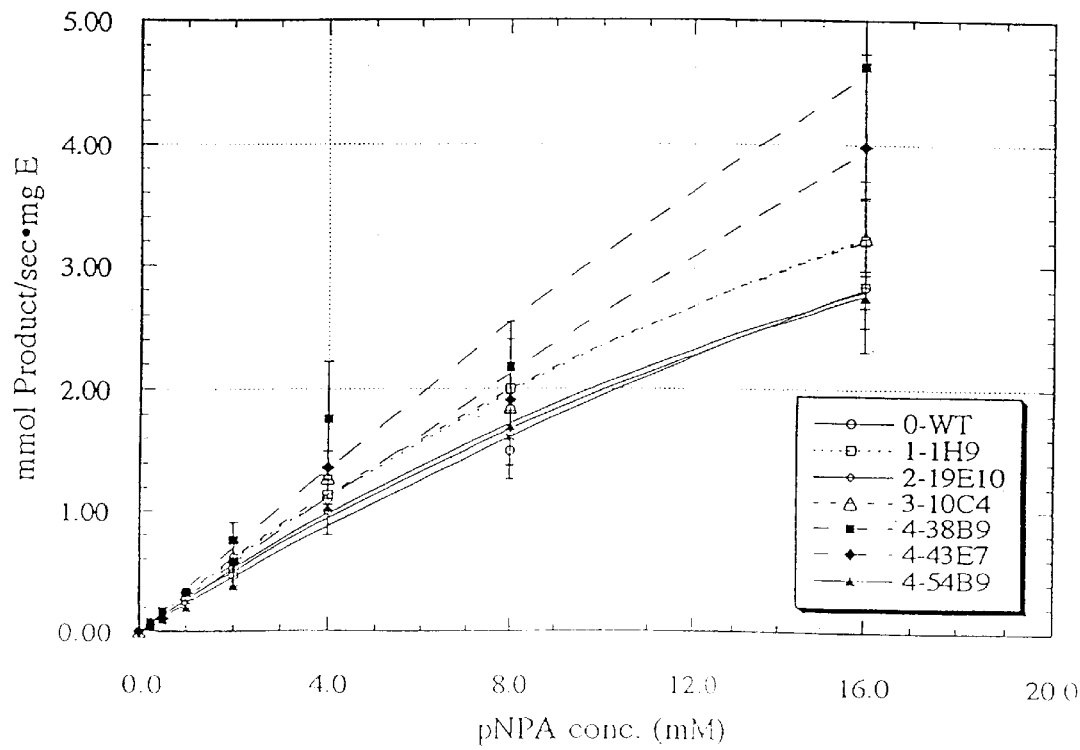
FIG. 8c is a plot of variant and wild type pNB esterase reaction kinetics on pNPA in 30% DMF. Enzyme were added to a 30° C. reaction solution consisting of 0.1 M PIPES (pH 7.0), 30% DMF, and varying concentrations of pNPA.

Bacteria expressing seven pNB esterases, O-WT (SEQ. ID. NO. 2), 1-1H9, 2-19E10, 3-10C4, 4-38B9, 4-43E7, and 4-54B9, were grown in on cultures, and the enzymes were purified. These purified enzymes were assayed for their ability to hydrolyze the different ester substrates in the presence of various concentrations of DMF. FIGS. 8a, b and c show the specific reaction rates on pNPA as a function of pNPA substrate concentration for this series of evolved variants from the four generations of mutagenesis and screening. Only 1-1H9 was chosen based on its performance on this substrate, and these assays performed on purified enzyme suggest that the majority of improvement in activity demonstrated by this variant during screening is due to an approximate four-fold increase in amount of enzyme produced. The wild type enzyme outperforms 1-1H9 in purely aqueous buffer (FIG. 8a). The actual screening, however, was performed in the presence of DMF, and in 15 and 30% DMF, 1-1H9 has higher specific activity towards pNPA than wild type (FIGS. 8b and 8c). Similar trends are seen for the remaining variants assayed on this substrate. Wild type is the most active enzyme in the absence of DMF, but is only average among the variants in 15% DMF. In 30% DMF, wild type drops still further relative to the pNB esterase variants. Variants 4-38B9 and 4-43E7, presumably by virtue of having been screened in DMF for four rounds of mutagenesis, are the best performers in 30% DMF.

Figure 9A:
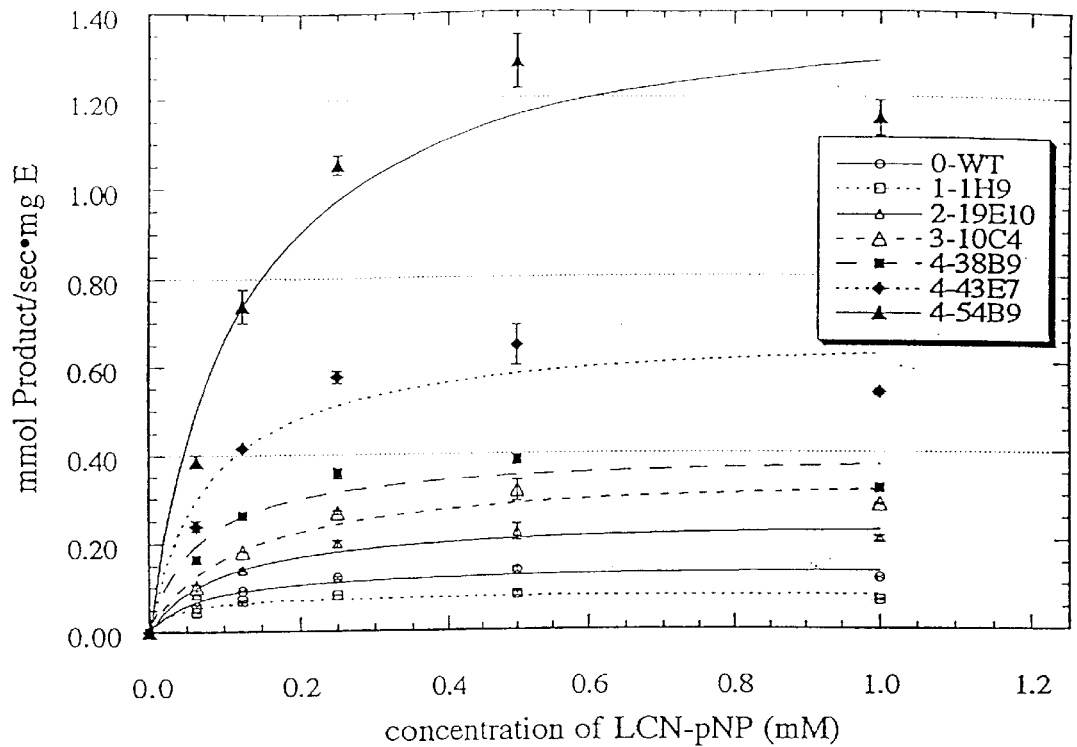
FIG. 9a is a plot of variant wild type pNB esterase kinetics on LCN-pNP in 1% DMF. Enzymes listed were added to a 30° C. reaction solution consisting of 0.1 M PIPES (pH 7.0), 1% DMF, and varying concentrations of LCN-pNP.

FIGS. 9a, b and c show the results of similar kinetic analyses performed using the LCN-pNP substrate with which three out of the four rounds of screening were carried out. In these plots the results of directed evolution are clearly seen. In 1, 15, and 30% DMF concentrations (FIGS. 9a, 9b, and 9c), the two variants least active on this substrate are the wild type enzyme and 1-1H9. This is not surprising given that neither of these enzymes had been screened on this substrate. Additionally, as the concentration of DMF increases, the activity of 1-1H9 increases with respect to wild type, so that in 30% DMF (FIG. 9c) enzymes display identical kinetics. The next enzyme from the bottom is 2-19E10 from the second generation of mutagenesis and screening. This variant increases the maximum reaction rate by a factor of two over wild type and three over its parent 1-1H9 at low percentages of DMF. The activity increase is sensitive to the presence of DMF, decreasing to a smaller improvement in 30% DMF. This trend continues with the 3-10C4 variant, which is 50% faster at producing product than its 2-19E10 parent in 1% DMF. 3-10C4 does not lose activity as rapidly as its parent in DMF and is 100% faster than 2-19E10 in 30% DMF. 3-10C4 is the parent of the remaining variants, all of which show enhanced activity. 4-38B9 shows the least amount of improvement, with a 20% increase in activity in 1% DMF. This increase in activity is enhanced in DMF to 50% in 30% DMF. 4-43E7 shows a constant two-fold increase in activity across all DMF ranges, and 4-54B9 is the most active of all the variants with a constant four-fold increase in activity over its parent. It is approximately 16 times more active than wild type pNB esterase. By comparing the scales of the axes, 4-54B9 retains the same activity in 30% DMF as the wild-type enzyme in 1% DMF.

Figure 10A:
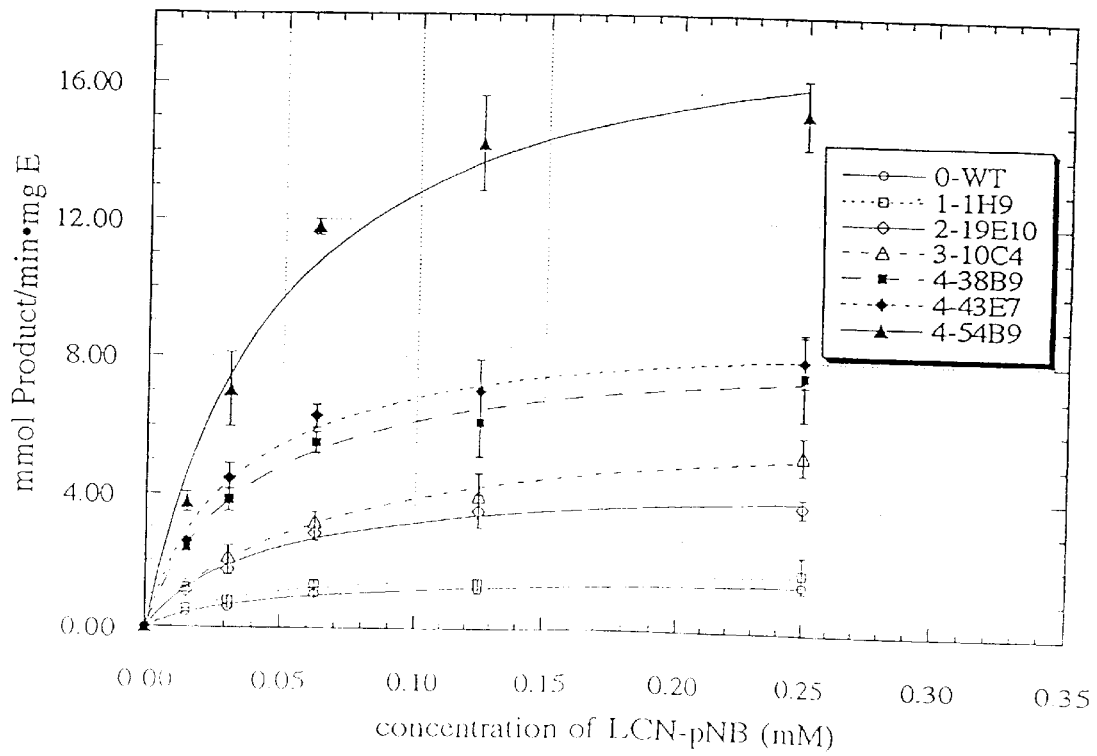
FIG. 10a is a plot of variant and wild type pNB esterase reaction kinetics on LCN-pNB in 1% DMF. Enzymes were added to a 30° C. reaction solution consisting of 0.1 M PIPES (pH 7.0), 1% DMF, and varying concentrations of LCN-pNB.
Figure 10B:
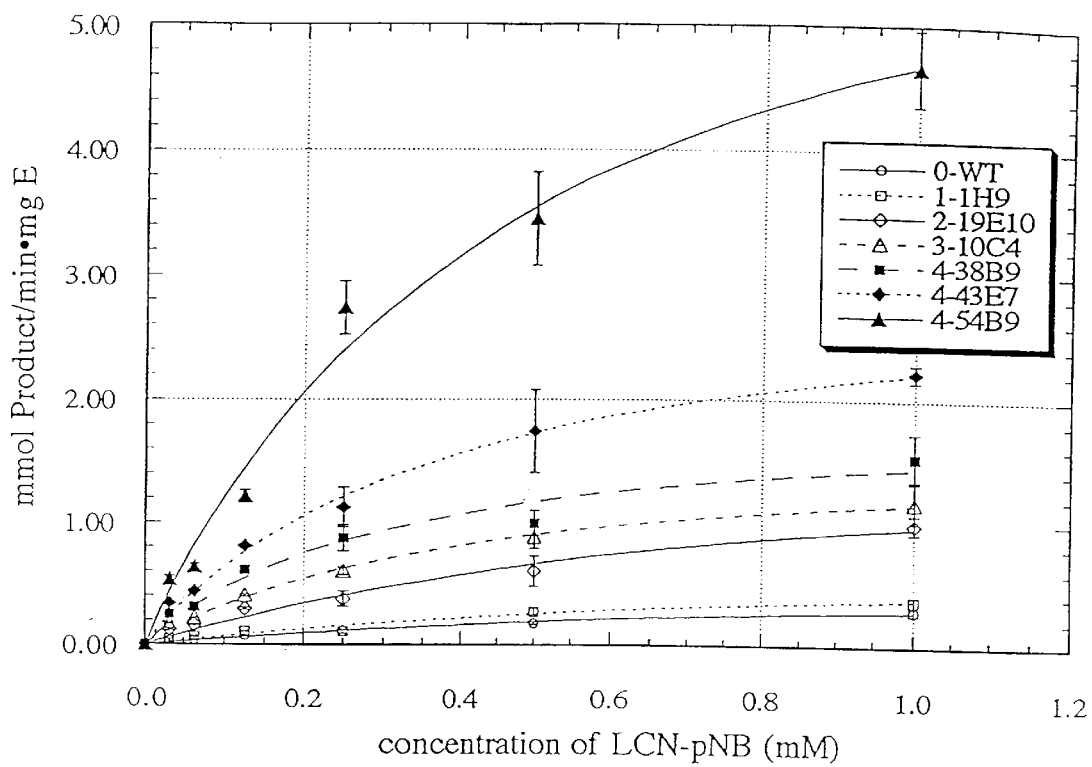
FIG. 10b is a plot of variant and wild type pNB esterase reaction kinetics on LCN-pNB in 15% DMF. Enzyme were added to a 30° C. reaction solution consisting of 0.1 M PIPES (pH 7.0), 15% DMF, and varying concentrations of LCN-pNB.

FIGS. 10a and b show the kinetic data obtained on the target LCN-pNB substrate. All the same trends are observed on the LCN-pNB substrate that were seen on the screening substrate (i.e. the fourth generation variants are more active than the third generation variant, which is more active than the second generation variant, etc.), with only minor exceptions. The first exception is that 1-1H9 no longer lags wild type in specific activity on this substrate. The second is that many of the variants, and especially those in the fourth generation, exhibit slightly lower increases in activity over wild type. For example 4-54B9 is now approximately 14 times more active than wild type on LCN-pNB, versus 16 times wild type on LCN-pNP. Additionally, DMF has a bigger negative effect on the LCN-pNB hydrolysis reaction than it does the hydrolysis of LCN-pNP. On LCN-pNP, 15% DMF reduces the maximal activity by a factor of two in the two best variants in 1% DMF, while 15% DMF affects the LCN-pNB hydrolysis by reducing the maximal activity by a factor of three over the 1% DMF activity.

Figure 12:
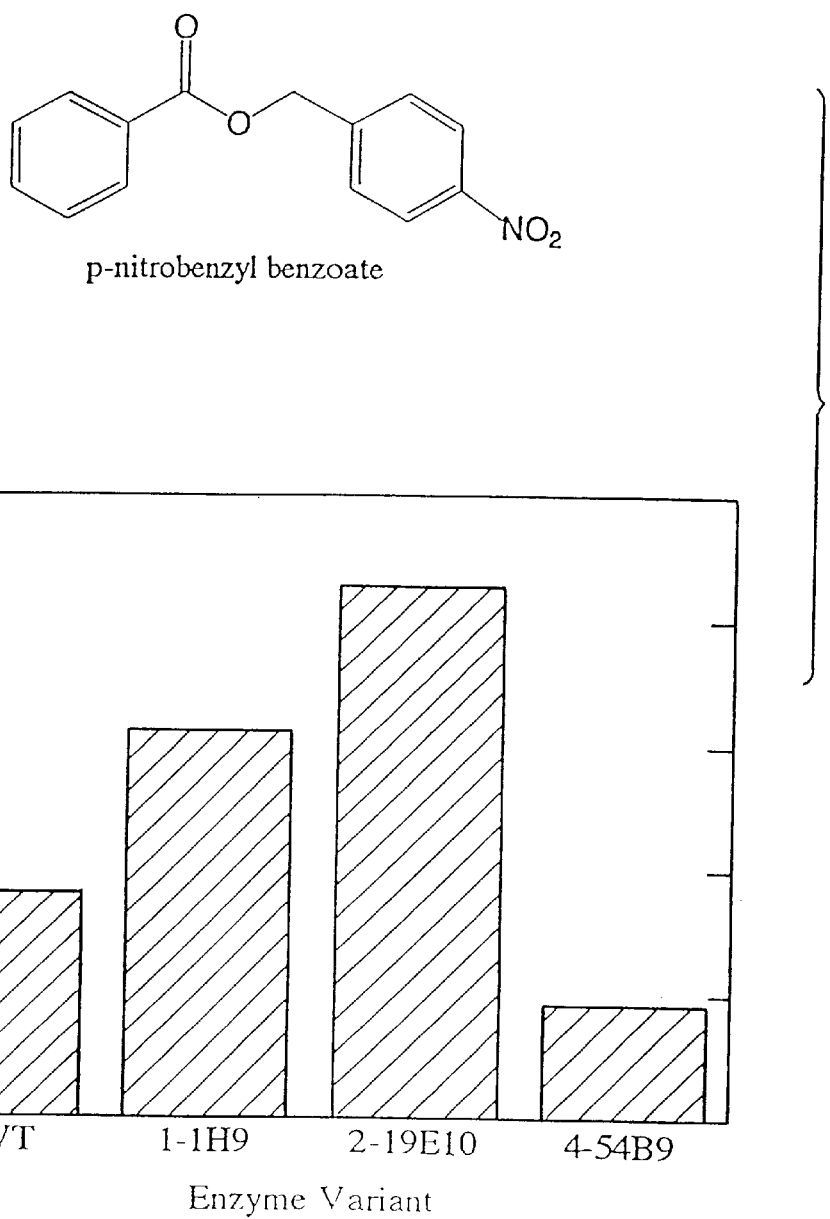
FIG. 12 shows graphic results of HPLC measurement of product of variant and wild type pNB esterase reaction on 1.0 mM p-nitrobenzyl benzoate in 20% DMF. The reaction was performed in 0.1 M PIPES (pH 7.0), 20% DMF and 1.0 mM substrate, 30° C.

The results shown in the Figures were used to calculate the $k_{cat}$, $K_M$ and $k_{cat}/K_M$ values reported in Table 3. In the case of the pNPA substrate, only $k_{cat}/K_M$ is reported because the solubility of the pNPA substrate did not permit the high substrate concentrations required to accurately determine the individual $k_{cat}$ and $K_M$ parameters. DMF dramatically increases $K_M$ while also decreasing $k_{cat}$. For the LCN substrates, the mutations accumulated during directed evolution mitigate the increased $K_M$. The effects on $k_{cat}$, however, are more prominent: $k_{cat}$ increases more than 9-fold from wild type to 4-54B9 in 15% DMF, while $K_M$ decreases by less than a factor of two on LCN-pNB. This result reflects the relatively high substrate concentration used during screening (0.8 mM). At substrate concentrations on the order of $K_M$, increased specific activity will result mainly from improvements in $k_{cat}$. These improvements are the most useful for enzymes intended to be used for transformations in high substrate concentrations.

combinations in FIGS. 11 and 12. L-glutamine pNB is soluble in aqueous buffer. Its enzyme-catalyzed deprotection in the absence of DMF is shown in FIG. 11a. All the pNB esterases tested catalyze this reaction, with wild type being the most active. The activity of the enzyme variant decreases from generation to generation. The results are altered significantly, however, when 20% DMF is added (FIG. 11b). Under these conditions, 2-19E10 pNB esterase demonstrates the most activity toward removing the pNB-protecting group from L-glutamine p-nitrobenzyl ester. The first generation variant 1-1H9 outperforms wild type by 20%, and the second generation variant 2-19E10 outperforms the wild type enzyme by 60%. The fourth generation variant 4-54B9 apparently introduces a substitution which disrupts the earlier generations' enhancements of activity: this enzyme has lost the ability to catalyze this reaction better than wild type.

Figure 9B:
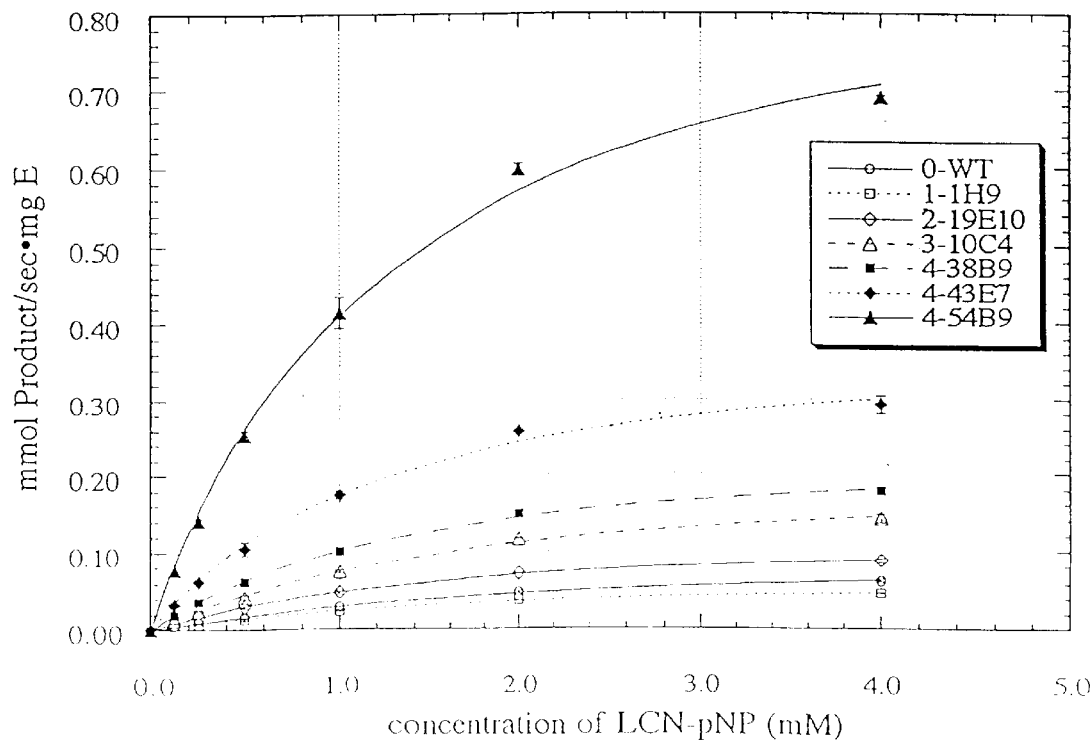
FIG. 9b is a plot of variant and wild type pNB esterase reaction kinetics on LCN-pNP in 15% DMF. Enzymes were added to a 30° C. reaction solution consisting of 0.1 M PIPES (pH 7.0), 15% DMF, and varying concentrations of LCN-pNP.
Figure 9C:
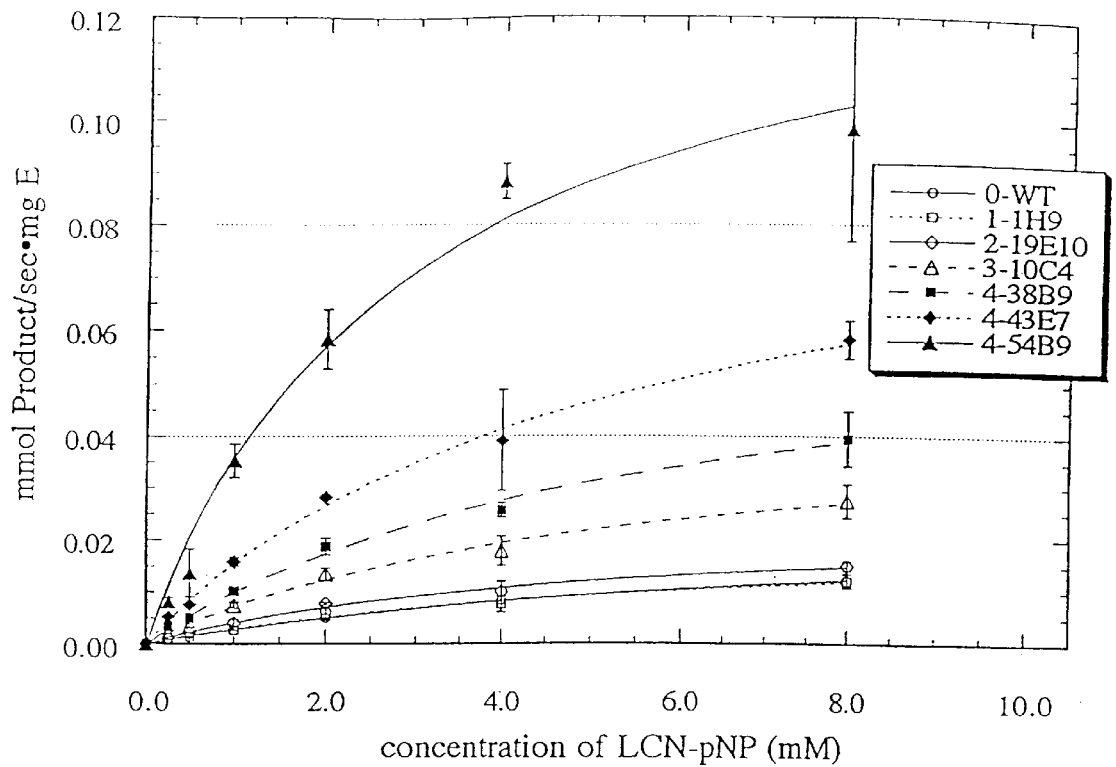
FIG. 9c is a plot of variant and wild type pNB esterase reaction kinetics on LCN-pNP in 30% DMF. Enzymes were added to a 30° C. reaction solution consisting of 0.1 M PIPES (pH 7.0), 30% DMF, and varying concentrations of LCN-pNP.

The hydrolysis of p-nitrobenzyl benzoate, reported in FIG. 12, shows the same trends demonstrated in FIG. 9b,

TABLE 3

Variants p-nitrophenyl acetate

| | 0% DMF kcat/Km | 15% DMF kcat/Km | 30% DMF kcat/Km |
|---|---|---|---|
| 0-WT | 5.67 | 0.94 | 0.24 |
| 1-1H9 | 4.05 | 1.08 | 0.32 |
| 2-19E10 | 3.20 | 0.89 | 0.28 |
| 3-10C4 | 2.50 | 0.86 | 0.33 |
| 4-38B9 | 3.04 | 1.03 | 0.36 |
| 4-43E7 | 2.42 | 0.81 | 0.29 |
| 4-54B9 | 2.57 | 0.64 | 0.27 | p-nitrophenyl loracarbef nucleus

| | 0% DMF | | 15% DMF | | | 30% DMF | |
|---|---|---|---|---|---|---|---|
| kcat | Km | kcat/Km | kcat | Km | kcat/Km | kcat | Km | kcat/Km |
| 0-WT | 0.14 | 0.07 | 2.11 | 0.10 | 2.36 | 0.04 | 0.024 | 7.55 | 0.003 |
| 1-1H9 | 0.08 | 0.03 | 2.47 | 0.07 | 1.84 | 0.04 | 0.021 | 6.05 | 0.003 |
| 2-19E10 | 0.25 | 0.09 | 2.68 | 0.12 | 1.50 | 0.08 | 0.023 | 4.67 | 0.005 |
| 3-10C4 | 0.35 | 0.11 | 3.15 | 0.21 | 1.77 | 0.12 | 0.044 | 5.18 | 0.009 |
| 4-38B9 | 0.39 | 0.06 | 6.18 | 0.25 | 1.41 | 0.17 | 0.067 | 5.68 | 0.012 |
| 4-43E7 | 0.67 | 0.08 | 8.51 | 0.40 | 1.27 | 0.31 | 0.094 | 5.09 | 0.018 |
| 4-54B9 | 1.44 | 0.12 | 12.09 | 0.93 | 1.27 | 0.73 | 0.141 | 2.92 | 0.048 | p-nitrobenzyl loracarbef nucleus

| | 0% DMF | | | 15% DMF | |
|---|---|---|---|---|---|
| | kcat | Km | kcat/Km | kcat | Km | kcat/Km |
| 0-WT | 1.64 | 0.04 | 38.27 | 0.54 | 0.88 | 0.61 |
| 1-1H9 | 1.94 | 0.04 | 50.75 | 0.69 | 0.85 | 0.82 |
| 2-19E10 | 4.59 | 0.04 | 102.59 | 1.81 | 0.87 | 2.09 |
| 3-10C4 | 6.53 | 0.07 | 96.37 | 1.62 | 0.40 | 4.05 |
| 4-38B9 | 8.51 | 0.04 | 222.47 | 1.89 | 0.31 | 6.17 |
| 4-43E7 | 9.13 | 0.03 | 271.06 | 3.02 | 0.37 | 8.11 |
| 4-54B9 | 18.96 | 0.05 | 396.41 | 6.84 | 0.46 | 14.74 |

Performance of Evolved Enzymes on Other Substrates

To determine the extent to which the newly-evolved enzymes exhibited increased general p-nitrobenzyl esterase activity, four purified pNB esterases (0-WT, 1-1H9, 2-19E10, and 4-54B9) were assayed on L-glutamine p-nitrobenzyl ester and p-nitrobenzyl benzoate by HPLC, as described in Materials and Methods. The resulting product peak areas are shown for the different substrate/enzyme although more dramatically. Because p-nitrobenzyl benzoate is not soluble in aqueous buffer, the assays on this substrate were performed only in 20% DMF. In this environment, 1-1H9 is 60% better than wild type, and 2-19E10 is 2.5 times better than wild type. 4-54B9 again has lost the ability to outperform previous generation variants, including the wild type pNB esterase.

pH Studies

Figure 13:
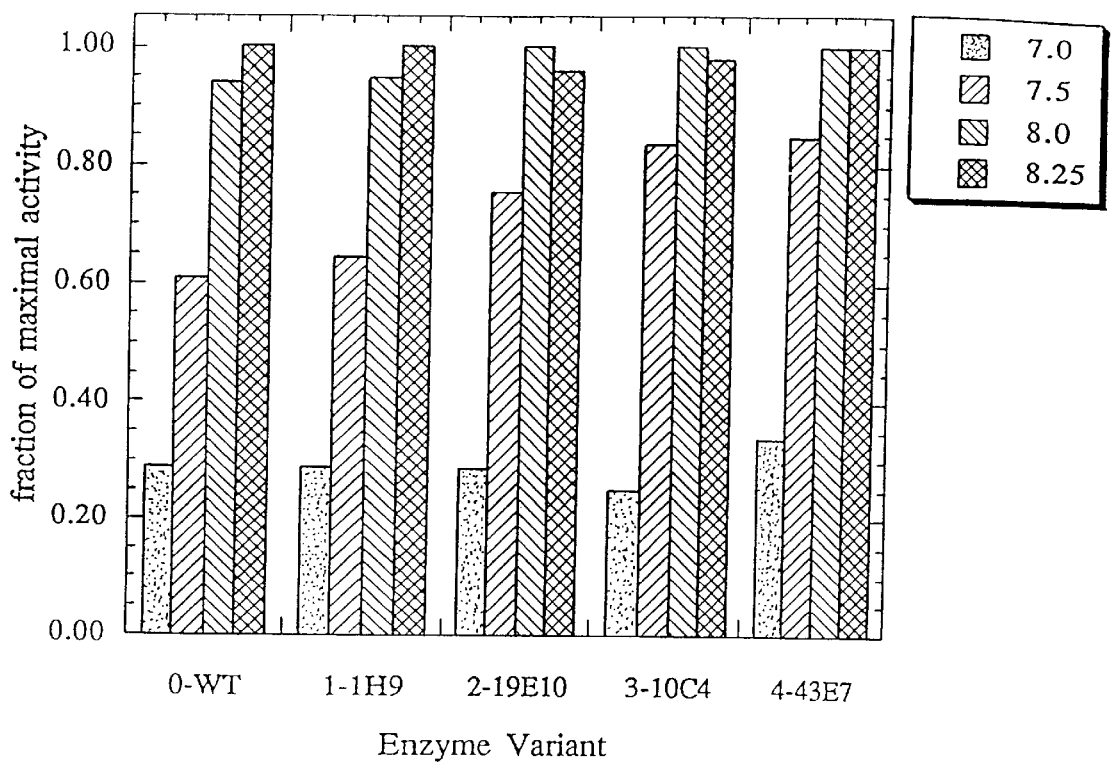
FIG. 13 shows the pH-activity profiles from pH 7.0 to 8.25 for a variant from each generation. The activity values for each variant are normalized to its maximal value. The enzyme samples were added to a 30° C. reaction solution consisting of 1% DMF, 0.5 mM p-nitrophenyl loracarbef nucleus, and 0.1 M PIPES (pH 7.0 to 8.25).

The pH optimum for activity of wild-type pNB esterase is 8.3 (6), while the screening for evolved pNB esterases was carried out at pH 7.0. To determine to what extent the pH-activity profiles of the pNB esterase were altered, or may have drifted, as a result of directed evolution at pH 7.0, the enzymes' abilities to hydrolyze the LCN-pNP screening substrate was measured as a function of pH. The activities normalized to the maximum activity for enzyme variants from each of the four generations are shown in FIG. 13. While the pH optima of the enzyme variants have not changed significantly, the pH-activity profiles of those from later generations have broadened slightly. In other words, reaction rates at lower pH values increase slightly for the modified enzymes which probably once again reflects the choice of pH 7.0 for screening.

Sequence Analysis

FIG. 3 presents the aligned DNA sequences of all the variants sequenced during this study. The variants are listed in order by generation, and the sequences start with DNA base one (A of the first codon ATG). The DNA bases conserved between all members of this pNB esterase family are boxed. Where a mutation has occurred, the column of DNA bases is not boxed, and a dash is indicated in the consensus sequence at the bottom of each set of rows.

FIG. 4 presents the amino acid sequence alignment of the pNB esterase family as translated from the DNA sequence alignment in FIG. 3. As before, the variants are listed in order by generation. The sequences start with amino acid one, and the DNA bases conserved between all members of this pNB esterase family are boxed. Where a mutation has occurred, the column of amino acid residues is not boxed, and a dash is indicated in the consensus sequence at the bottom of each set of rows.

Figure 2:
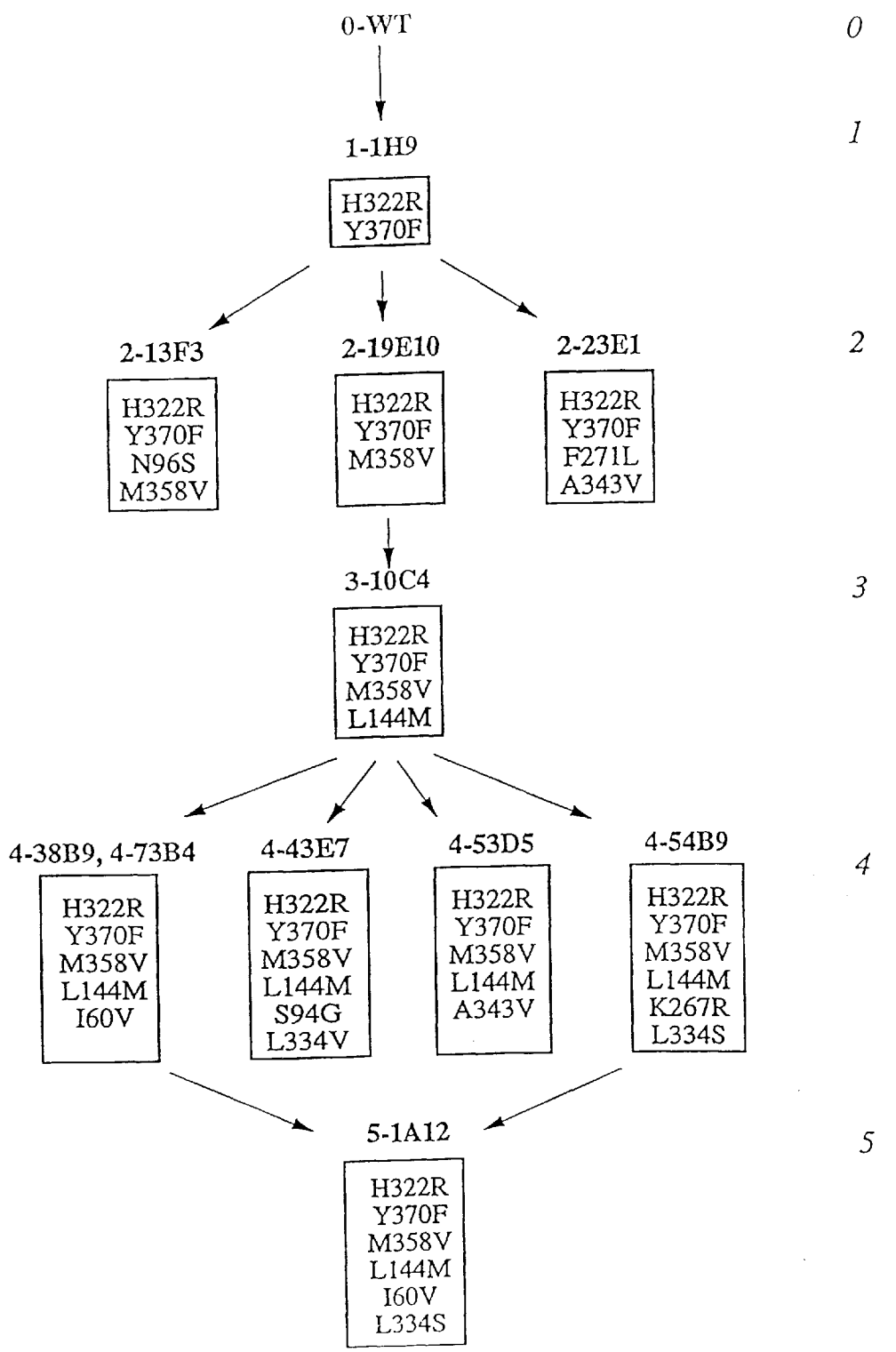
FIG. 2 is a diagram showing the amino acid substitution progression in para-nitrobenzyl esterase variants. The esterase variants are labeled in bold-type and boxed beneath each label are the amino acid substitutions present in each variant. The amino acid substitutions were determined by translation of DNA sequencing results.
Figure 3A:
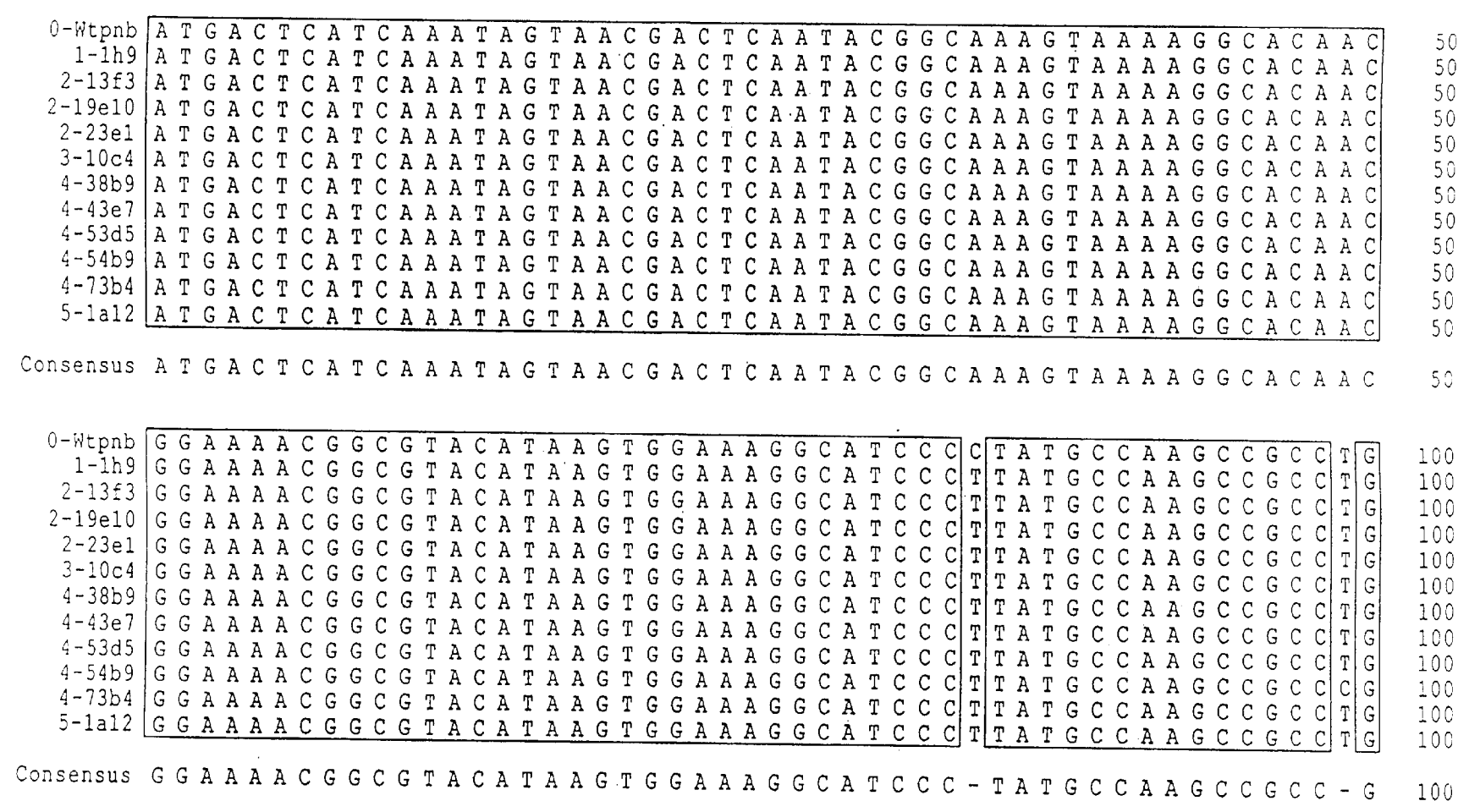
Figure 3B:
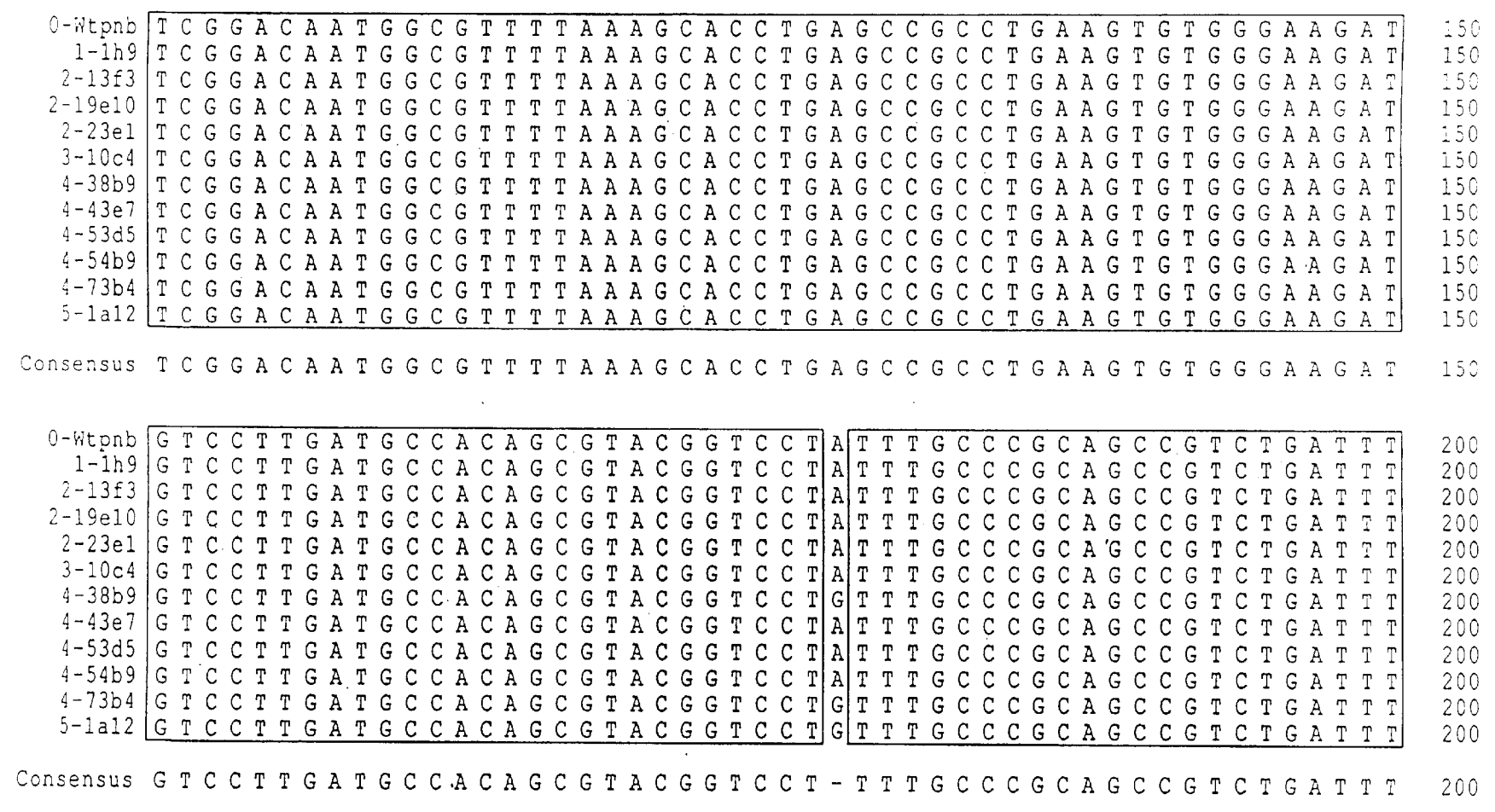
Figure 3C:
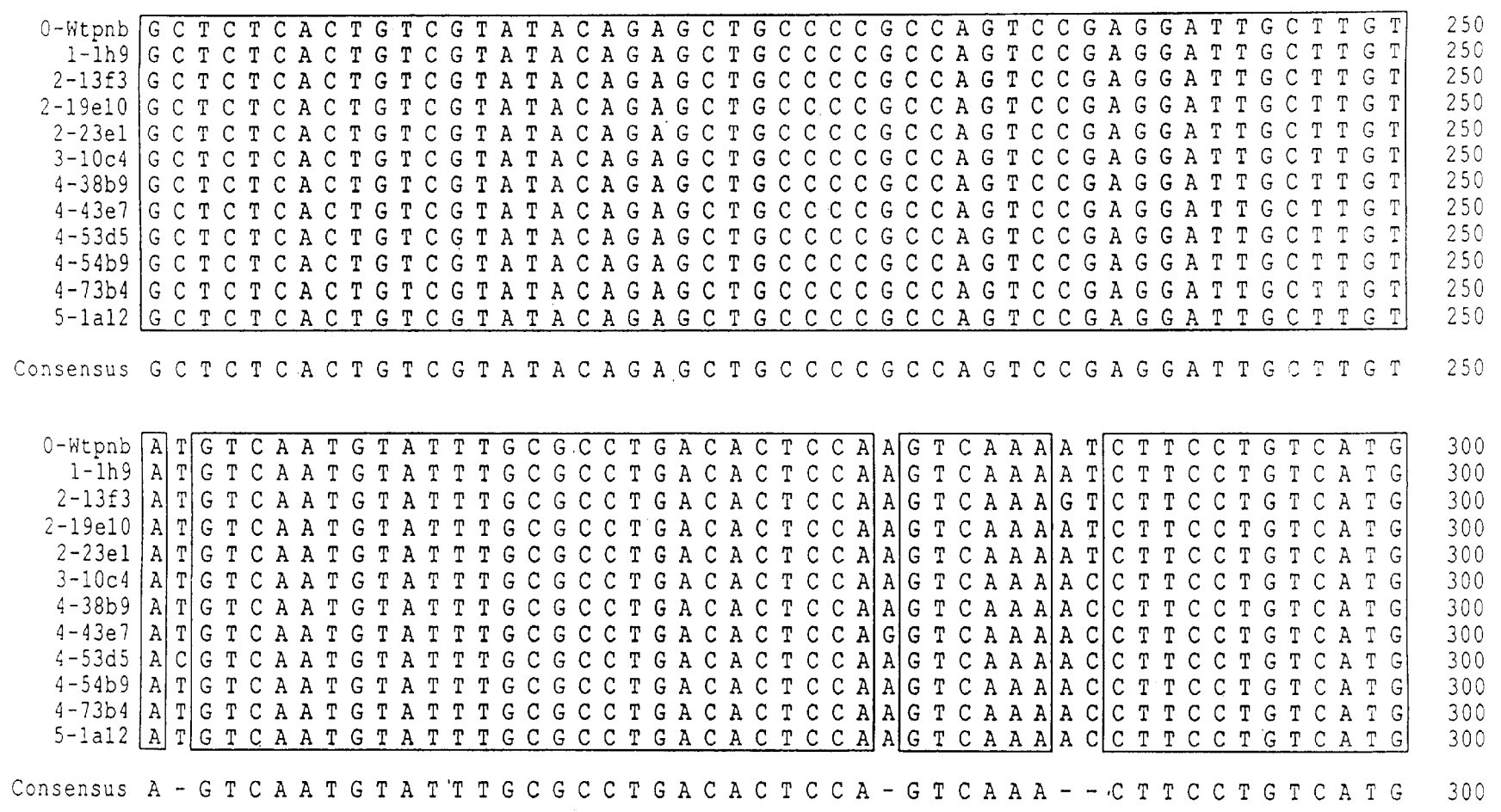
Figure 3D:
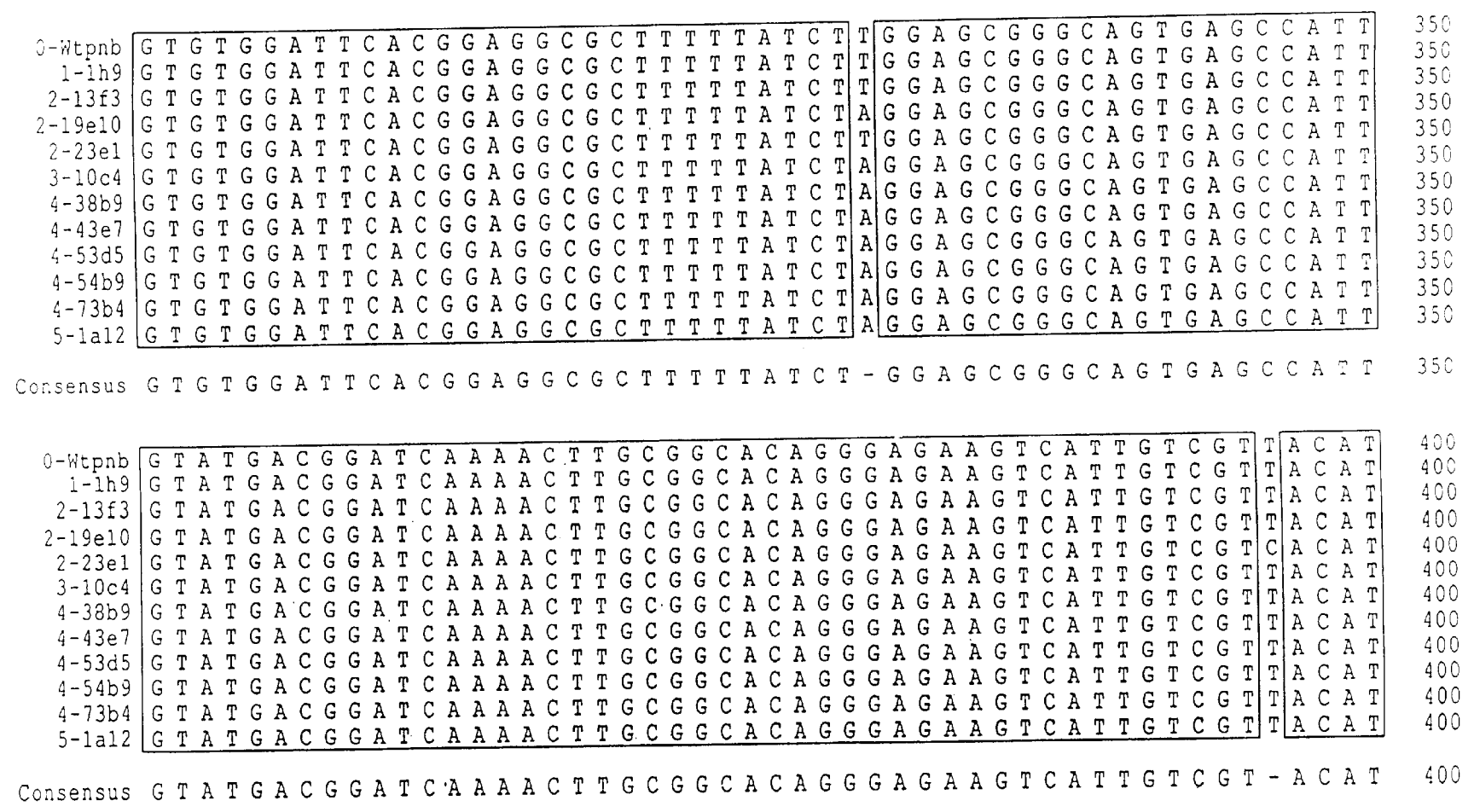
Figure 3E:
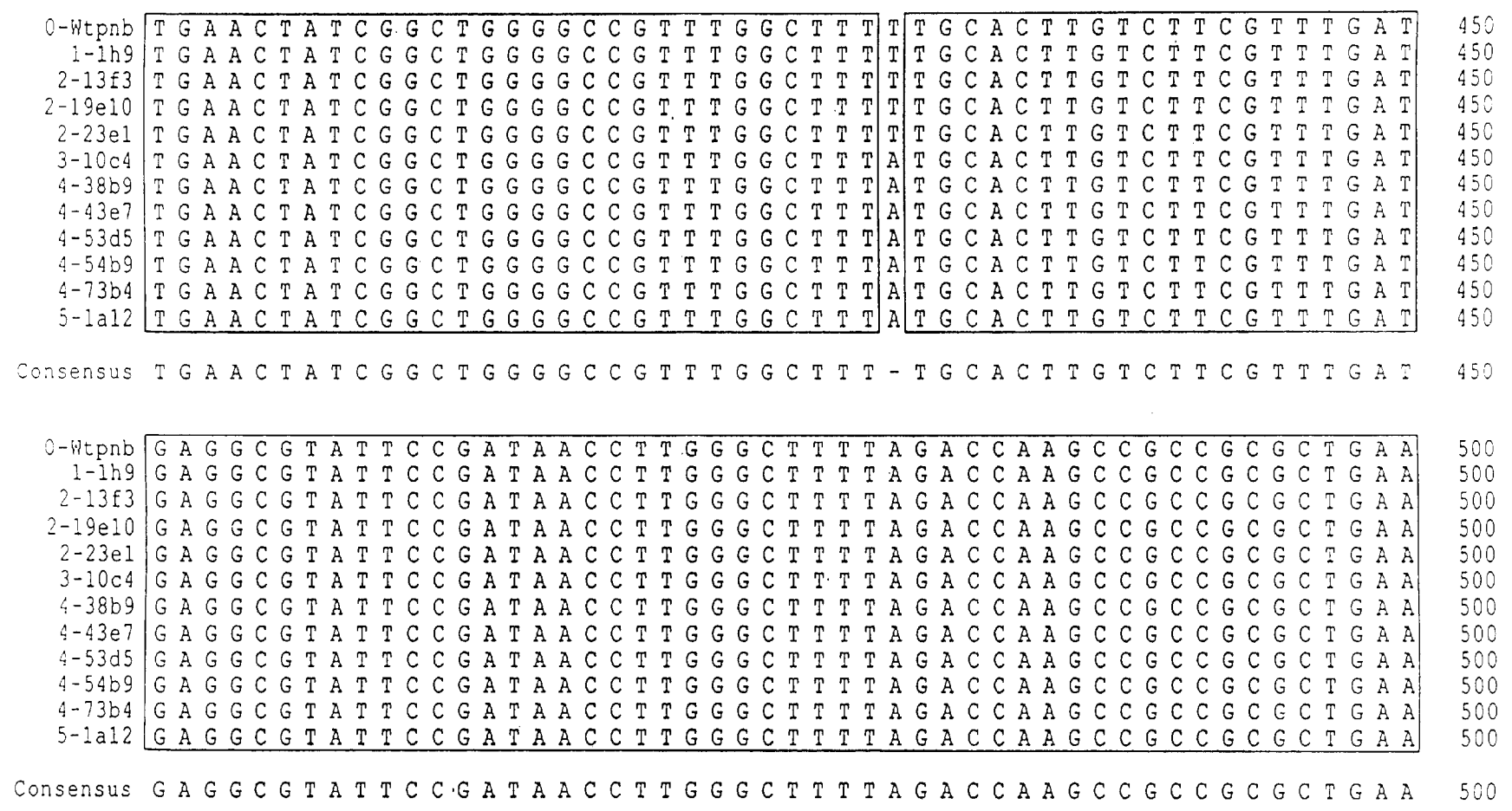
Figure 3F:
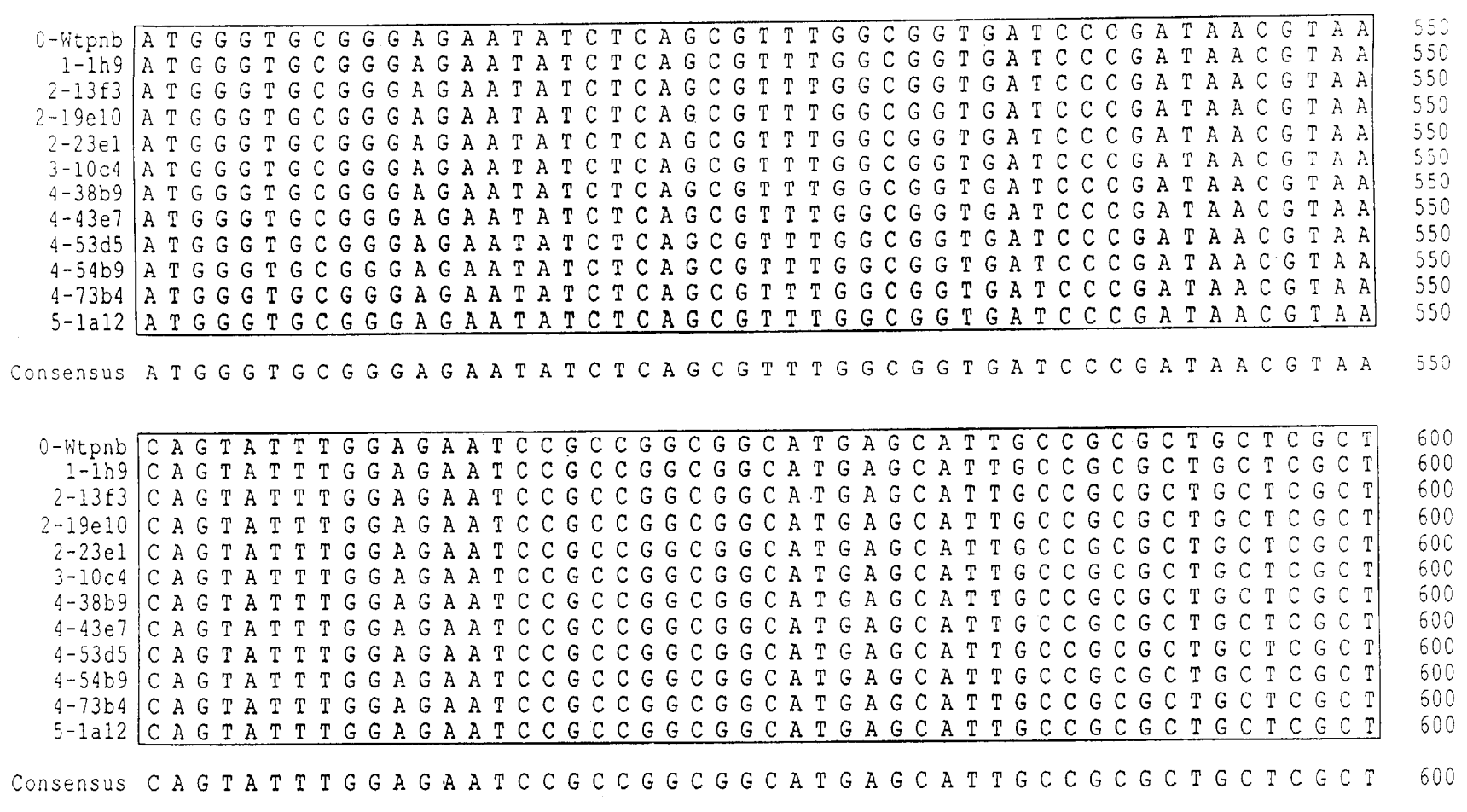
Figure 3G:
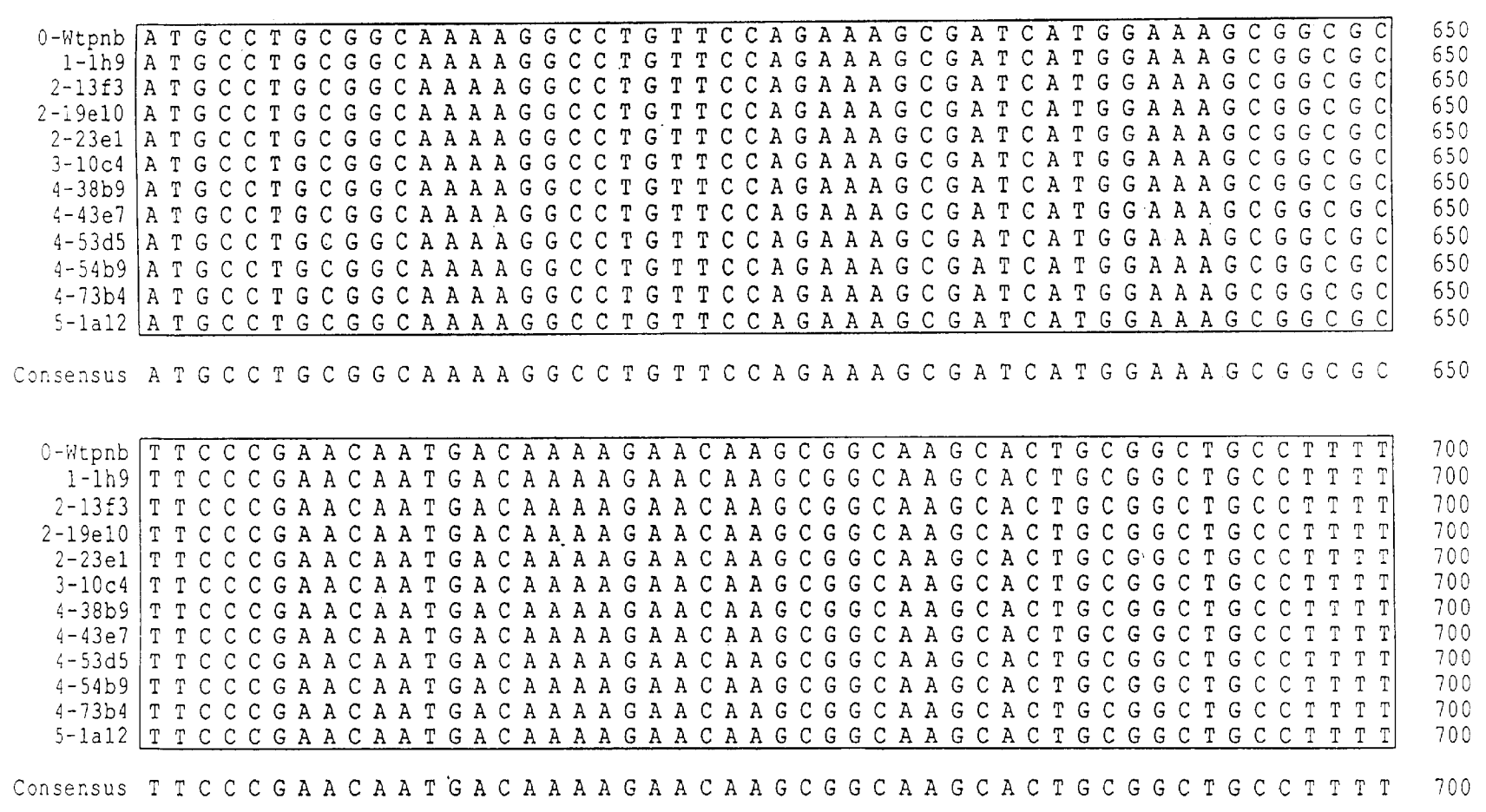
Figure 3H:
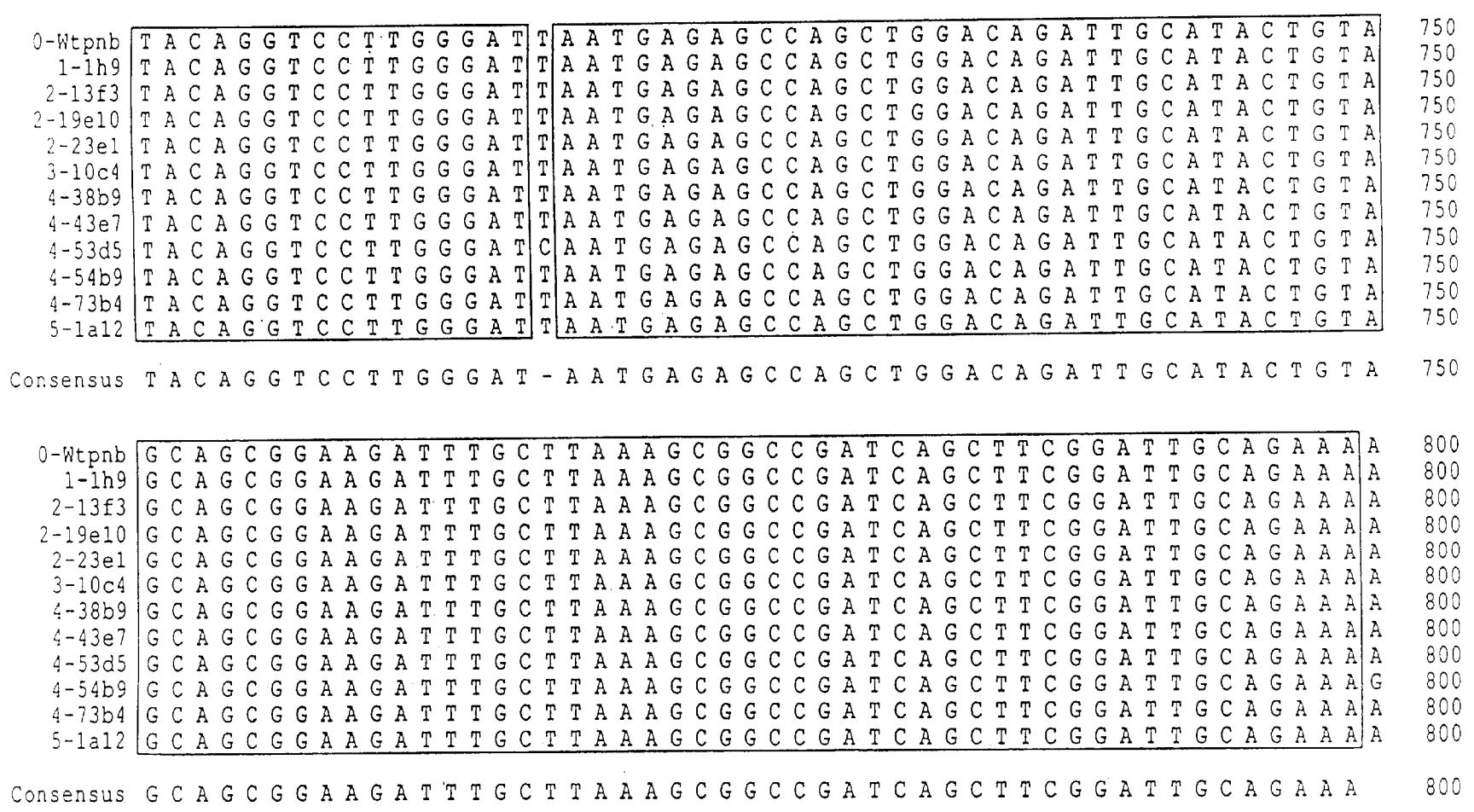
Figure 3I:
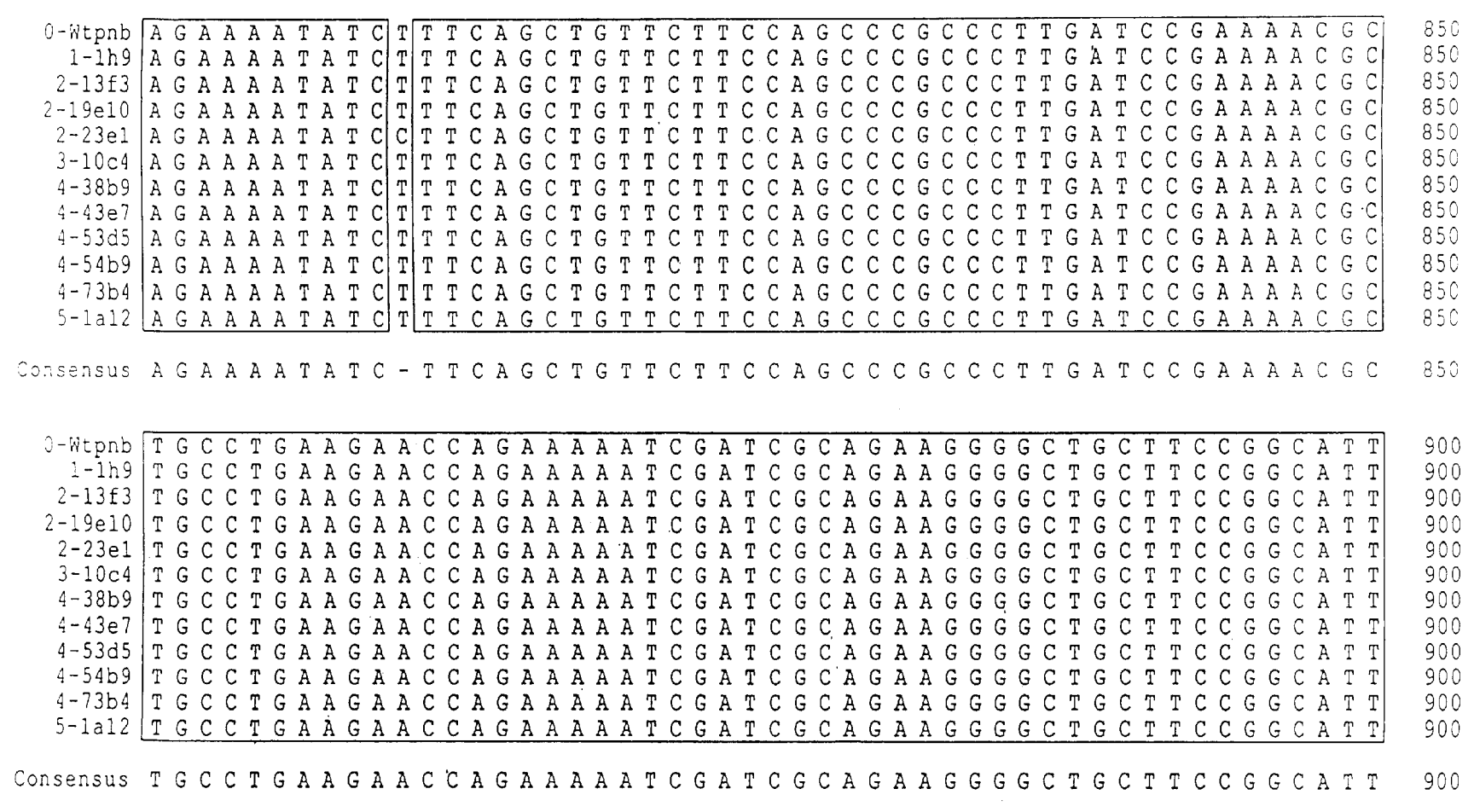
Figure 3J:
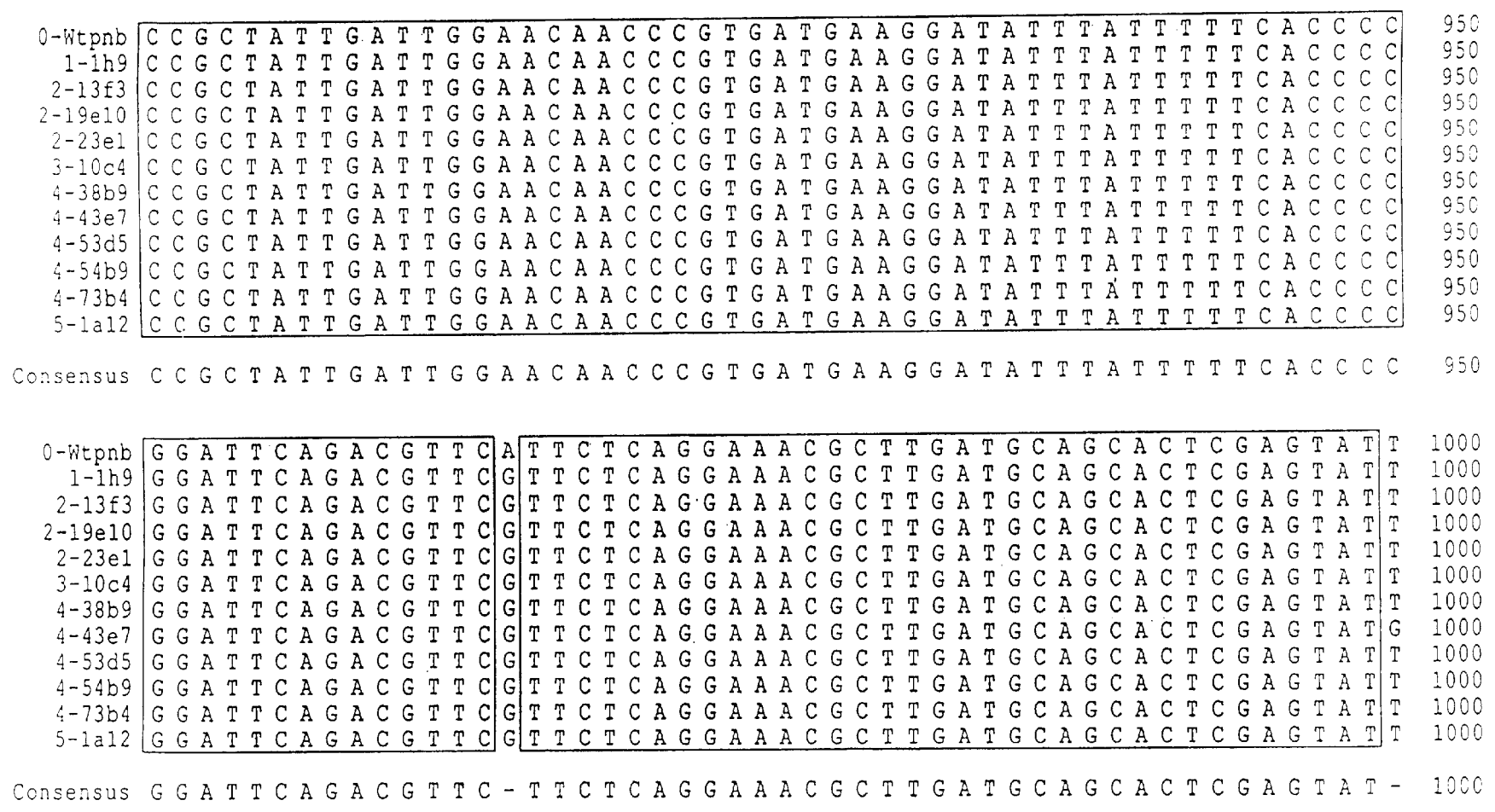
Figure 3K:
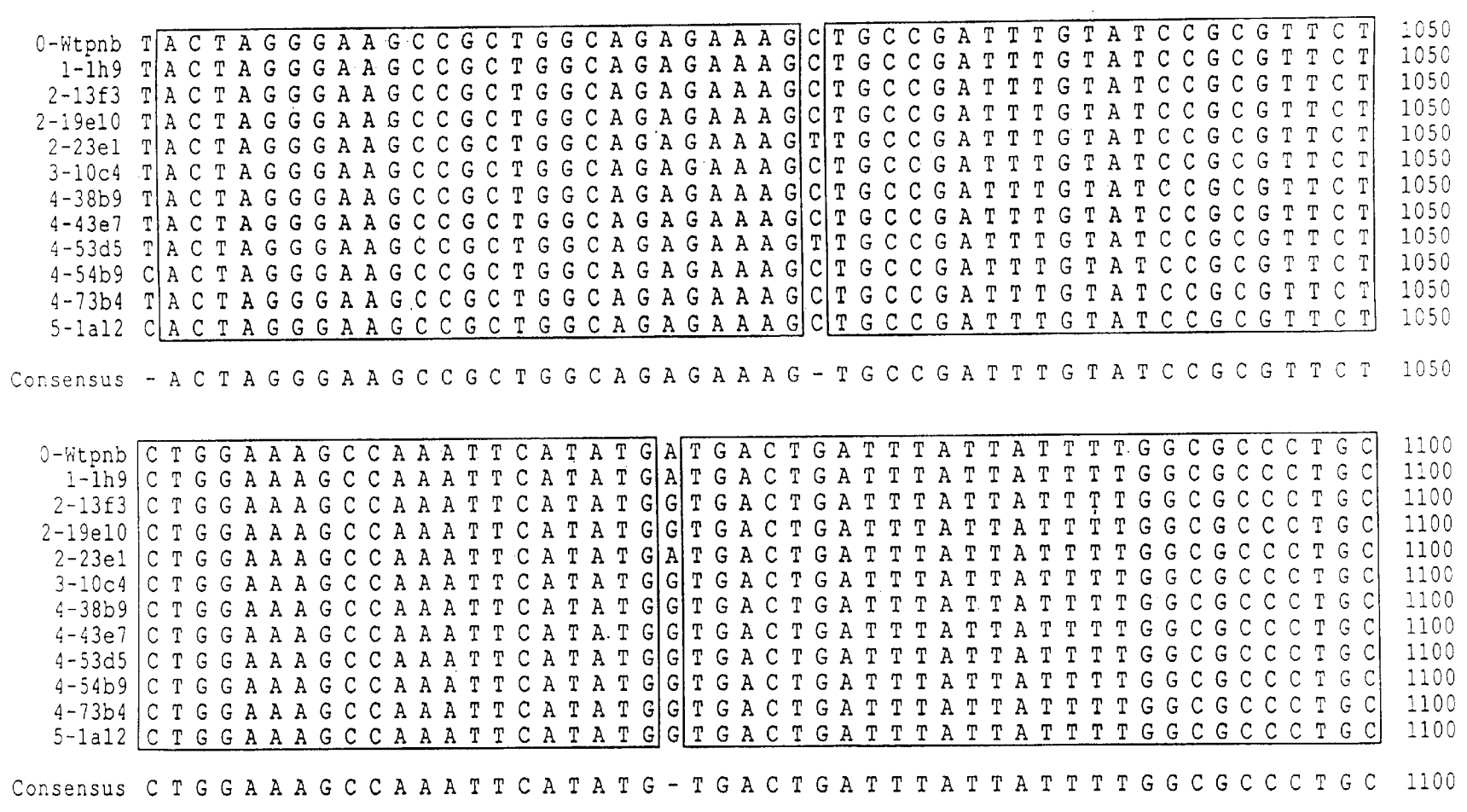
Figure 3L:
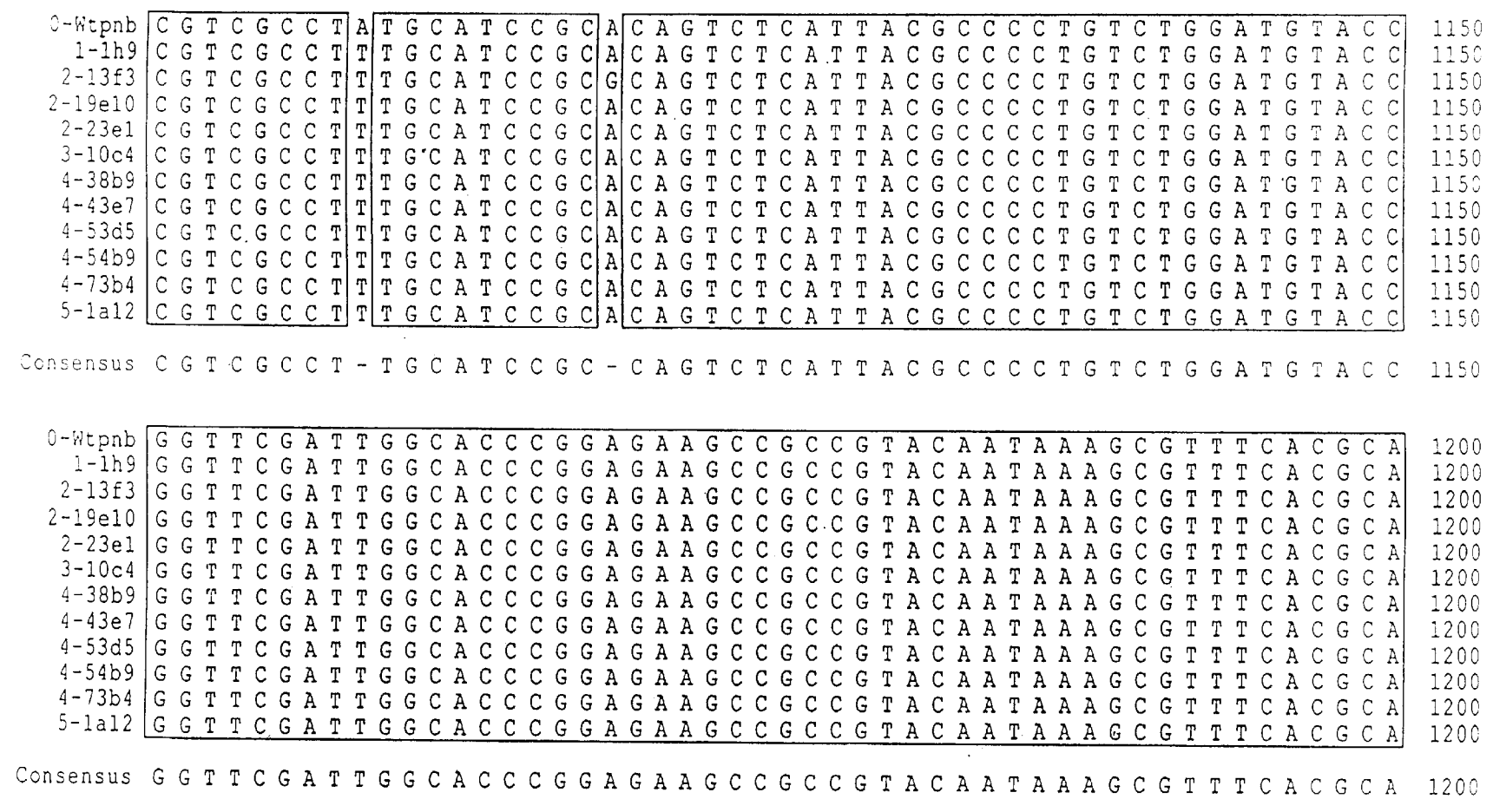
Figure 3M:
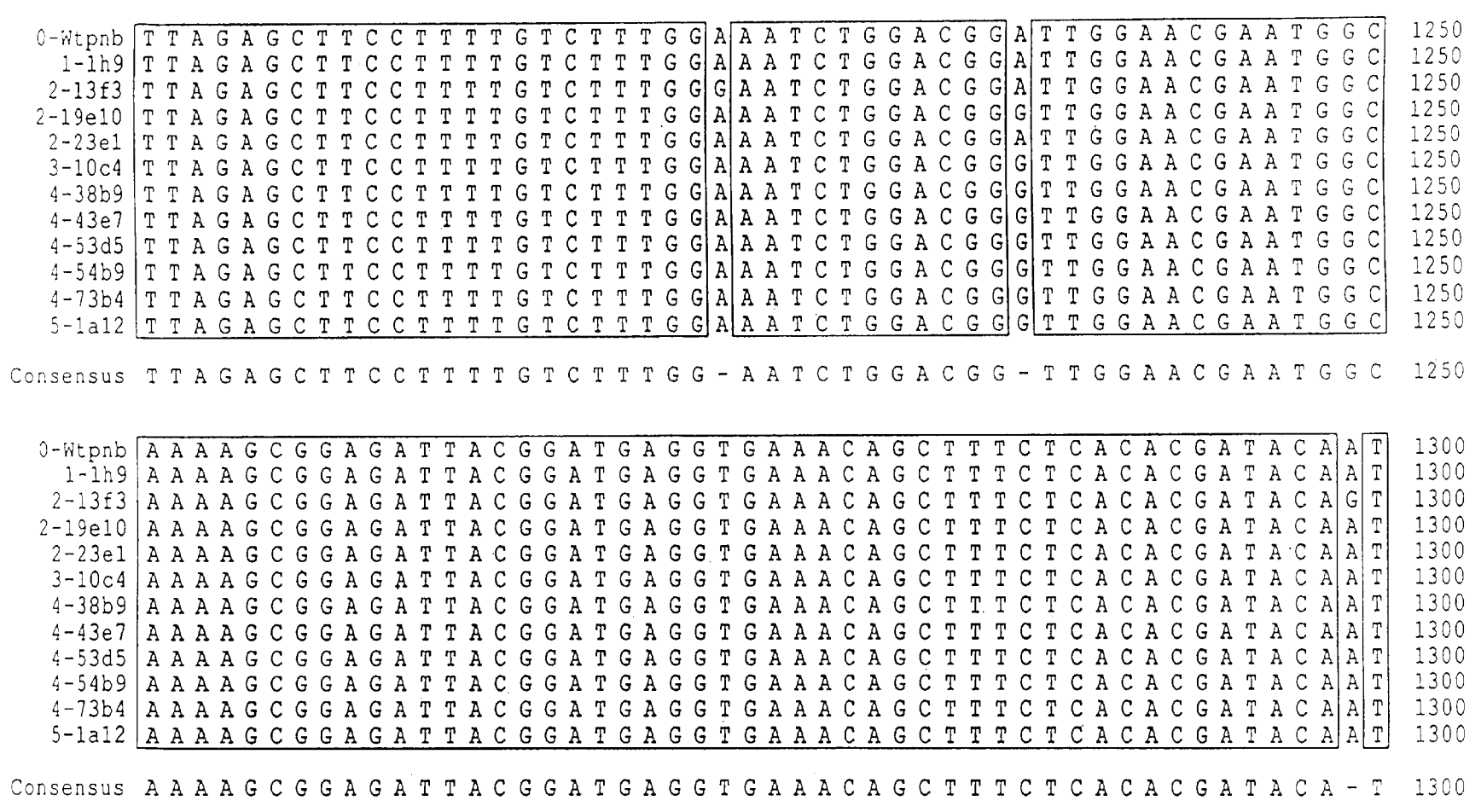
Figure 4A:
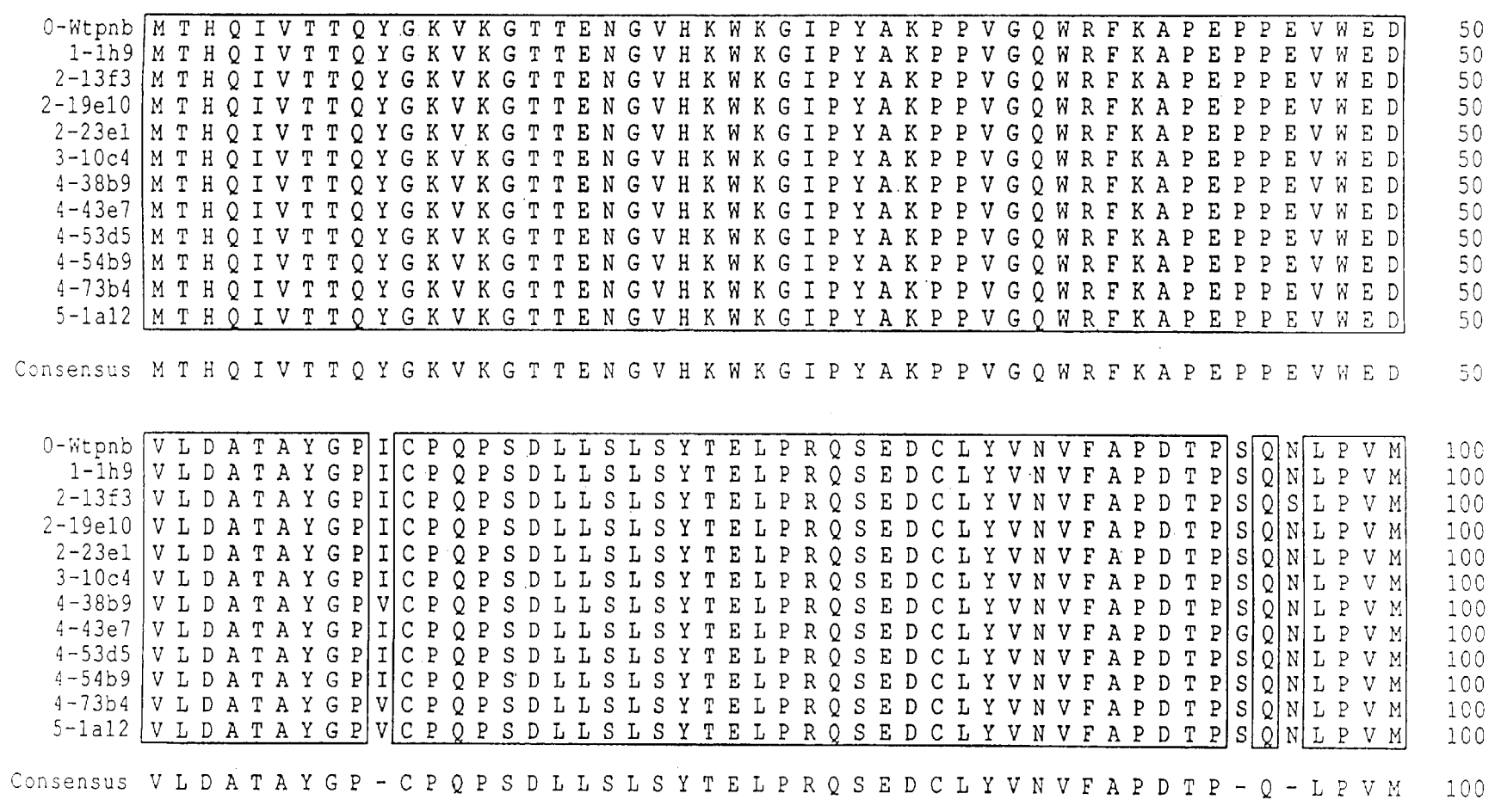
Figure 4B:
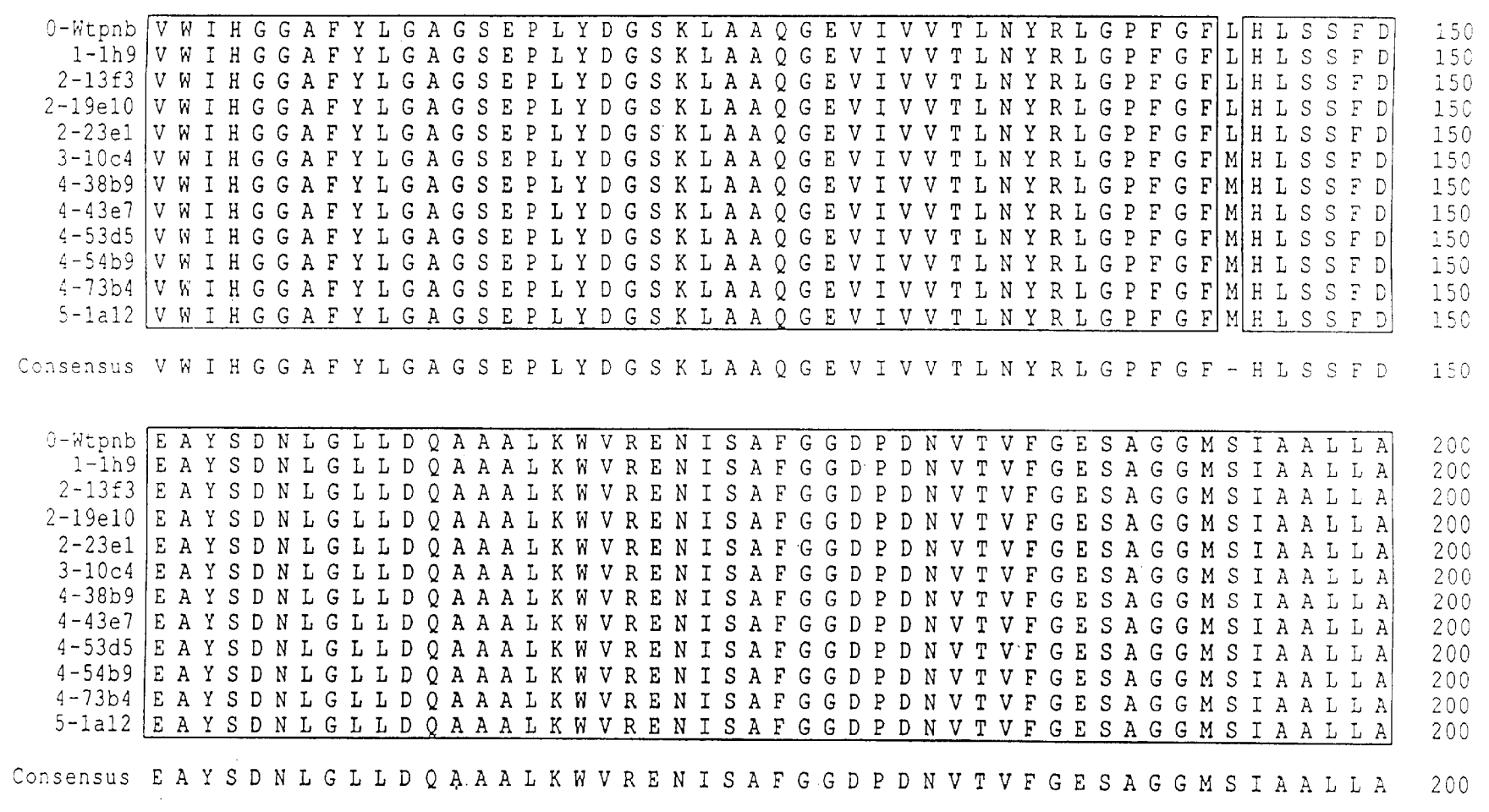
Figure 4C:
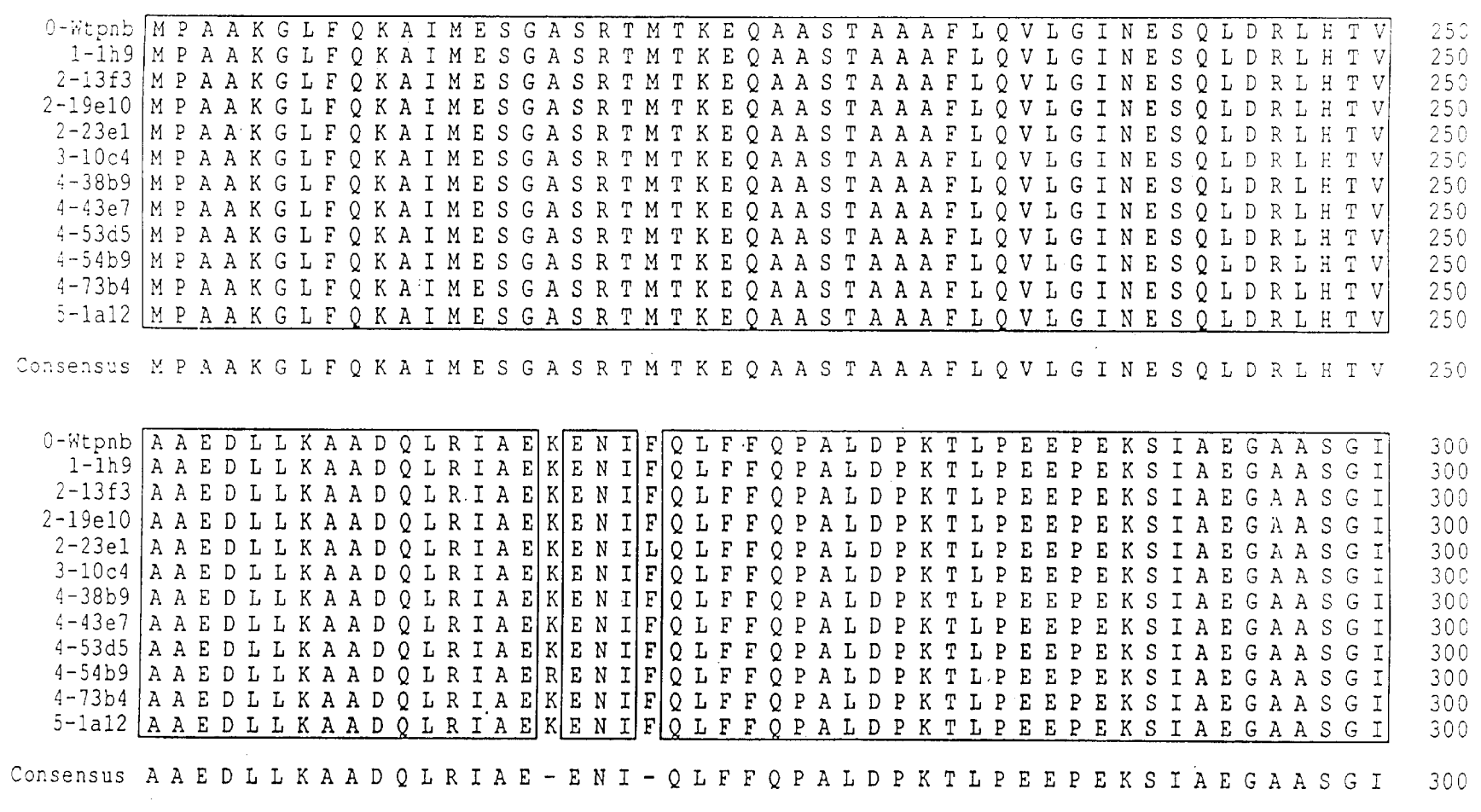
Figure 4D:
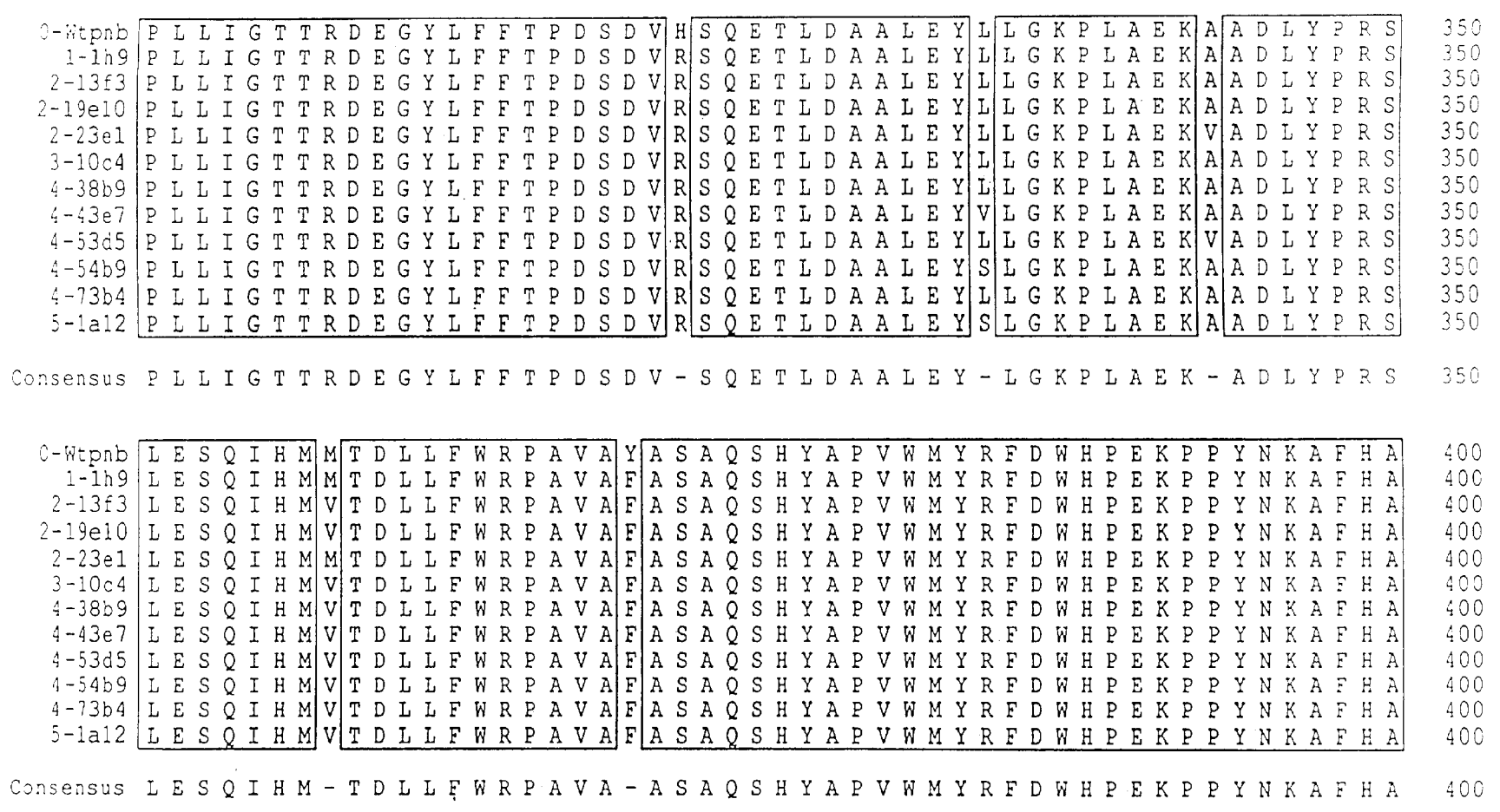
Figure 4E:
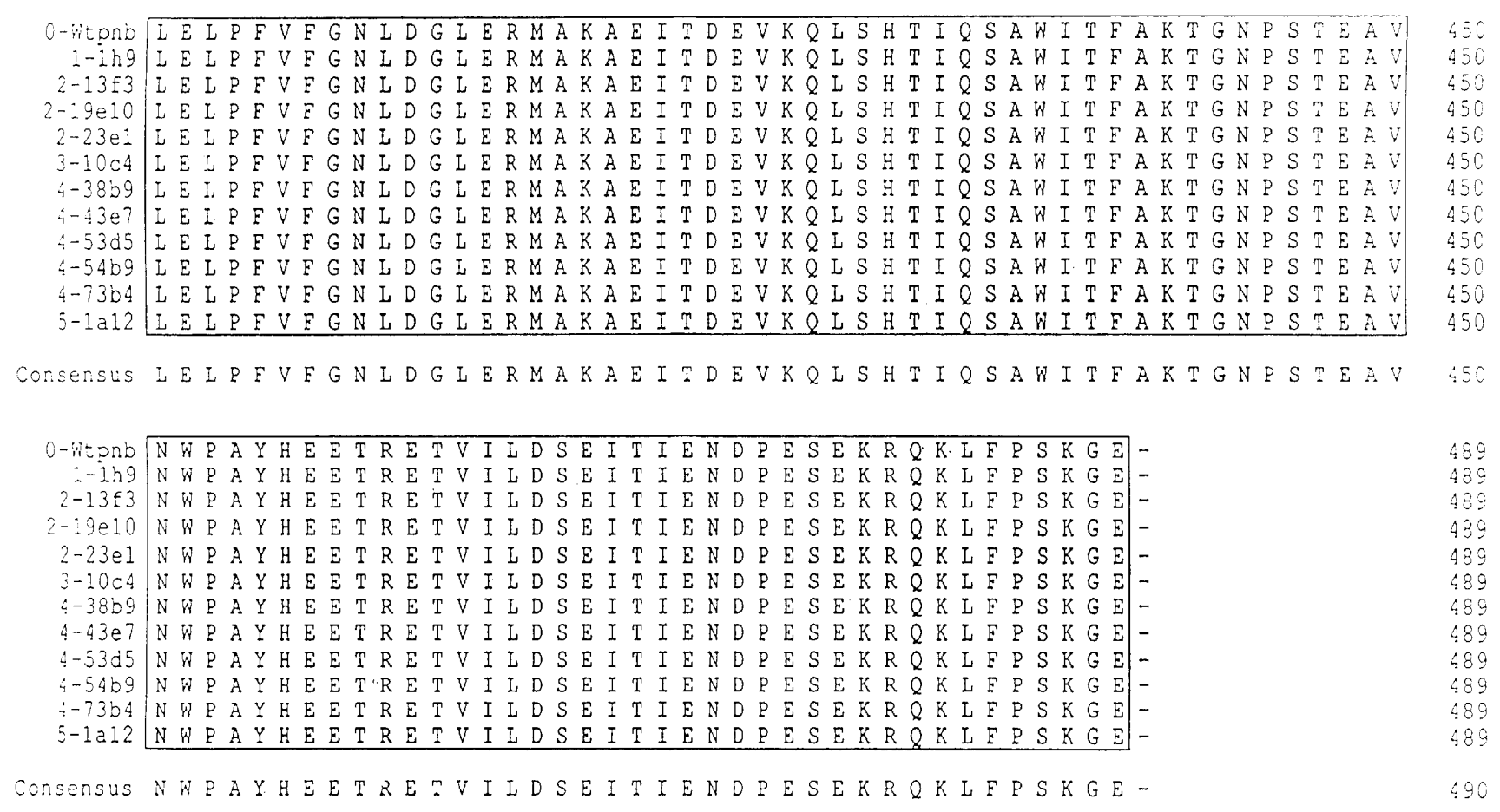

FIG. 2 is an "evolution tree" summarizing the amino acid substitutions and positions resulting from the amino acid sequence information in FIG. 4. All three clones sequenced from the second generation contain the substitutions observed in the 1-1H9 sequence, as well as a few new additional substitutions. This can be seen at the DNA level in FIG. 3 and at the protein level in FIG. 2. Two of the second generation clones contain the same DNA substitution, an A to G substitution at position 1075, which gives rise to the substitution of methionine at position 358 by valine. This residue is believed to be responsible for the increased specific activity of these two clones, as it is the only non-silent mutation in clone 2-19E10, whose catalytic activity is slightly better than 2-13F3. 2-19E10 was chosen to parent the third round of mutagenesis. One silent and one translated substitution are added to the evolutionary sequence in 3-10C4; a T to A substitution at position 433 gives rise to leucine 144 substituted by methionine. The next five sequences are progeny of 3-10C4 from the fourth generation. All have the eight DNA base substitutions of 3-10C4 in common as the cumulative result of the three previous rounds of evolution. 4-38B9 and 4-73B4 each contain only an identical open reading frame substitution, an A to G change at position 181, leading to isoleucine at position 60 changed to valine. As a result, these two variants are listed together in FIG. 2. 4-43E7 and 4-54B9 each contain two substitutions; one occurs within identical codons in the DNA sequence, giving rise to changes in leucine 334 to valine in 4-43E7 and serine in 4-54B9.

5-1A12 was created as a combination of 4-38B9 and 4-54B9 by cutting and religating these two genes near the 1000 DNA base position. 5-1A12 is therefore expected to contain the isoleucine 60 to valine substitution from 4-38B9 and the leucine 334 to serine substitution from 4-54B9.

The location versus frequency of substitution was examined and the locations of substitutions resulting in amino acid changes appears distinctly non-random. Fully half of the translated substitutions DNA mutations lie within a 144 base pair stretch of DNA (less than 10% of the open reading frame). This is due to the fact that a non-random selection of enzymes were chosen for sequencing (only those exhibiting improved activity). This region of the amino acid sequence plays an important role in substrate recognition and enzyme activity.

Random Mutagenesis

The frequency of substitutions as a function of position within the gene sequence was determined. It was found that the locations of DNA substitutions in the sequenced genes are well distributed throughout the target sequence. Thus the error-prone PCR technique generates variations at random locations. The types of substitutions generated, however, are not random. Of the 29 unique substitutions, 25 were substitutions changing an A or T, 4 were substitutions of C, and none were substitutions of G. These bases were changed almost half of the time to G, with A to G changes making up the majority ($9/10$) of these substitutions. This non-randomness is also shown in the number of transition (purine to purine changes—A to G or C to T) to transversion (purine to pyrimidine changes—A to T/G or C to A/G or T to A/G) substitutions, where the transitions outnumber the transversions 24 to 5.

The conditions used in these examples (differing from normal PCR conditions by increases in all four dNTP concentrations) give a reported error-rate of between 1.5 and 4 base substitutions per 1000 bases. Under these conditions, the substitutions should be predominantly transitions (e.g. A to G), no transversions (e.g. A to T), and a small fraction of insertion or deletions. The sequence data presented here demonstrate a significant bias towards A to G substitutions, especially in the first two generations. We found that the substitution frequency was at the higher limit of the expected range, with the 1-1H9 variant demonstrating a substitution rate of 3.5 substitutions per 1000 bases, and highly populated with A to G changes. The third and fourth PCR reactions yielded lower mutation frequencies, with only 1 to 2.5 substitutions per 1000 bases. Transition substitutions still outnumbered transversion substitutions by 3 to 1. In no case was a G mutated.

Substitution bias in the resulting protein sequences also arises from the fact that the DNA sequence is translated to the amino acid sequence through the triplet coding ribosomes. Twenty amino acids are encoded by sixty-one triplet DNA codons, the distribution of these codons is far from even. For example, tryptophan is coded for by only one of the 64 triplet codons (TGG), while Leu is encoded by six. Single base changes within a codon are the only type of base changes we can expect to see, as the probability of making two random substitutions within one codon is small. On average, only five to six new amino acids are available to replace each amino acid in the original sequence by single base substitution. Thus, the translation process introduces non-randomness in the amino acid sequence. This is useful for directed evolution in accordance with the present invention, when one does not want to radically alter an enzyme that has some catalytic activity, but rather wants to incorporate small changes which enhance the enzyme's ability to perform. This bias towards conservative amino acid substitutions is demonstrated in the examples with most changes being conservative ones, such as tyrosine 370 to phenylalanine in 1-1H9, phenylalanine 271 to leucine in 2-23E1, and isoleucine 60 to valine in 4-38B9.

MATERIALS AND METHODS

DNA

The plasmid pNB106R was provided by Eli Lilly & Co (Indianapolis, Ind.). This plasmid contains the pNB esterase gene under the control of an altered 1 promoter, pL106 (U.S. patent application Ser. No. 07/739,280) (4). The plasmid also contains a temperature sensitive 1 CI repressor which inactivates the pL106 promoter below 35° C. Further, the plasmid contains an $E.\ coli$ origin of replication, a plasmid copy control gene, and a tetracycline resistance gene.

Computer Work

Homology searches and sequence alignments were performed at the California Institute of Technology's Sequence Analysis Facility using the GCG Sequence Analysis Software Package version 8.0 from the Genetics Computer Group (University Research Park, Madison, Wis.). BLAST searches of the Brookhaven Protein Data Bank (PDB), the SWISS-PROT database, the Protein Information Resource database, and the translated GenBank database were performed at the National Center for Biotechnology Information using a BLAST network service. PHYLIP was used at the same facility to construct evolutionary trees.

Restriction of DNA

Plasmid and fragment DNA when required were cut with Bam HI and Xba I (Boerhinger Mannheim, Germany) in restriction buffer B at 37° C. for one hour. The resulting linear DNA was then run on a 1% agarose gel and separated into bands according to size. The appropriately sized band was excised from the gel and extracted using either the GeneClean (Bio101, Vista Calif.) or Qiagen (Chatsworth, Calif.) method. In both cases purified DNA was eluted in Tris-EDTA buffer.

Random Mutagenesis

The pNB esterase gene (1470 base pairs (bp)) in pNB106R is flanked by an Xba I restriction site 51 bp before the start of the ORF and by a Bam HI site 313 bp downstream from the stop codon (4). PCR primers (3'-GAGCACATCAGATCTATTAAC-5' and 3'-GGAGTGGCTCACAGTCGGT-GG-5') were synthesized to complement regions 25 bp upstream of the Xba I site and 143 bp downstream of the Bam HI site to allow andom mutagenesis over a 2000 bp region including the entire pNB esterase open reading frame. A solution containing 1 mM dNTPs, 16.6 mM $(NH_4)_2SO_4$, 67 mMTris-HCl (pH 8.8), 6.1 mM $MgCl_2$, 6.7 mM EDTA (pH 8.0), and 10 mM b-mercaptoethanol, 6 mg of forward and reverse primers, 10 ng of plasmid pNB106R and 2.5 units of Taq DNA polymerase (Perkin Elmer-Cetus, Foster City, Calif.) in a total volume of 100 mL were covered with 2–3 drops of light mineral oil (Sigma, St. Louis, Mo.)). The sample was then placed in a well containing 2–3 drops of mineral oil of a Precision Scientific thermal cycler. The thermal cycler repeats the following steps: 1 minute at 94° C., 2 minutes at 42° C., and 1 minute at 72° C. for 25 cycles. These conditions should generate an error frequency of approximately one substitution per 1000 bases, or approximately 1.5 substitutions per gene copy (10). The fragment of DNA amplified by this technique was then subjected to a phenol/chloroform extraction and ethanol precipitation. The DNA was restricted and purified as described above.

Competent Cell Preparation

Competent TG1 cells were prepared according to the CaCl2 method (40). TG1 cells were grown overnight at 37° C. in a 3 mL culture of LB broth. The cells were diluted 1:200 in fresh LB and allowed to grow to an $OD_{600}$ of 0.35 to 0.40. They were placed on ice for 1 hour and spun at maximum speed in a 4° C. Beckman tabletop centrifuge. The cell pellet was resuspended in 0.5 volumes of 0.1 M $CaCl_2$ and allowed to sit on ice for 30 minutes to 1 hour and recentrifuged as before. The cell pellets were resuspended in sterile 0.02 volumes of 0.1 M $CaCl_2$, 10% v/v glycerol and frozen at −70° C. until use.

Ligation and Transformation

Ligation reactions were performed using T4 DNA ligase (Boerhinger-Mannheim, Germany). Vector DNA (the entire pNB106R plasmid excluding the pNB esterase gene between Xba I and Bam HI), insert DNA (the pNB esterase gene between Xba I and Bam HI), 10X ligation buffer, water and enzyme were combined and incubated at 4° C. overnight (12–16 hours). The solution was incubated with previously prepared competent cells on ice for 1 hour. The cells were then heat shocked at 42° C. for 1 minute, supplied with an equal volume of LB media, and incubated at 30° C. for 45 minutes. This solution was then plated onto LB plates containing tetracycline to 20 mg/mL (LB tet plates).

Screening

Transformants arising from ligations of pNBE vector and randomly mutagenized inserts were allowed to grow for 36 to 48 hours before shifting to 42° C. to induce expression of the pNB esterase gene. After an eight hour induction period, each colony was picked with a sterile toothpick and resuspended in a unique well of a 96 well plate containing 200 mL of 0.1 M Tris-HCl (pH 7.0). The turbidity of each well was measured as the absorbance at 620 nm adjusted by a cell-free reference well by a 96 well plate reader. A 20 mL aliquot from each well was pipetted into a second 96 well plate, to which was added 200 mL of a substrate solution containing 0.8 mM para-nitrophenyl acetate (pNPA) and 0.4% (v/v) acetonitrile or para-nitrophenyl loracarbef nucleus (LCN-pNP), 0.1M Tris-HCl (pH 7.0), and between 0 and 30% v/v dimethylformamide (EM Science Guaranteed Reagent grade). The resulting reaction was monitored using the 96 well plate reader at 405 nm. Reactions were typically monitored for 11 data points varying from 15 seconds between data points for 0% DMF measurements to 180 seconds between data points for 30% DMF. The slopes of the best-fit lines through the resulting 11 data points for each of the 96 wells were normalized by the corresponding absorbance at 620 nm measured previously. These normalized values were compared, and the wells exhibiting the highest activity to turbidity ratios were plated onto LB tet plates. Two single colonies from these plates were restreaked on LB tet plates to provide single colony isolates for further testing. Two single colonies from each of these second plates (four colonies total) were then arrayed onto LB tet plates using sterile toothpicks. This collection of potential variants was then rescreened using the activity to turbidity ratio assay again. Of those that showed better activity to turbidity than wild type, the best three were chosen for larger scale culture and purification.

Crude screening was performed on the fourth generation variants using the LCN-pNB substrate using a similar whole cell assay. 0.10 ml samples of the resuspended colonies were removed from each well of the 96 well plate and added to a quartz cuvette containing a 1000 ml reaction solution consisting of 2.5% DMF, 0.1 M Tris-HCl (pH 7.0), and 0.25 mM LCN-pNB. The absorbance at 291 nm of each sample was measured for 2.5 min. using a UV spectrophotometer. Initial rates were measured for both the LCN-pNP substrate in the 96 well plate assay (above) and the LCN-pNB substrate in quartz cuvettes. Both sets of slopes generated from the initial rate data were normalized to the turbidity measurements at 620 nm.

Cell Culture

Single colonies were inoculated into 5 mL LB tet culture tubes and allowed to grow overnight at 30° C. The contents of these tubes were then used to inoculate a one-liter culture of LB tet and allowed to grow to maximum turbidity. These one-liter cultures were decanted into sterile centrifuge bottles and spun at 6000 rpms in a JA-10 rotor for 15 minutes in a Beckman centrifuge. The cell pellets were resuspended in LB tet pre-warmed to 42° C. The flasks were placed in a 42° C. incubator and allowed to shake for 8 hours (4). The cells were harvested by similar centrifugation and resuspended in a centrifuge tube in 25 mL of Buffer A (Lysis Buffer), consisting of 10 mM potassium phosphate, 1 mM b-mercaptoethanol, and 0.5 mM EDTA (pH 7.0).

Cell Lysis

A French Press was used to lyse the harvested cells. The lysis was accomplished by placing the chilled sample into a steel housing, which was compressed to 20,000 atmospheres. A small needle valve was then opened and the cells were released to ambient conditions, causing the cells to rupture. This process was repeated three times to insure complete lysis. The steel housing was kept chilled prior to use at 4° C. and the samples were stored before and after on ice.

Purification

After lysis the cell debris was pelleted by centrifugation at 12,000 g in a JA-20 rotor for 15 minutes at 4° C. (6). The cell lysate supernatant was adjusted to pH 5.0 with HCl, and the newly formed precipitate was removed by centrifugation at 12,000 g in a Beckman JA-20 rotor for 30 minutes at 4° C. The supernatant volume was measured and ammonium sulfate was dissolved to 45% saturation at 0° C. For reference, the ammonium sulfate saturation amount used for calculations was 41.22 g/100 mL solution at 0° C. The solution was chilled to 0° C. on ice for 5 minutes and centrifuged in a JA-20 rotor at 12,000 g for 30 min. at 4° C. The supernatant was transferred to a new centrifuge tube, where ammonium sulfate was added to bring the final amount to 85% saturation at 0° C. Centrifugation was performed as before, and the supernatant discarded. The pellet was redissolved in Buffer B (10 mM Tris-HCl, 50 mM NaCl, 1 mM b-mercaptoethanol, and 0.5 mM EDTA (pH 8.5)), placed in an Amicon® spin filtration unit (Centricon-10) and buffer exchanged three times with Buffer B to remove the ammonium sulfate. The resulting protein sample was applied to a DEAE-sepharose column (2.5 cm ID×10 cm high) pre-equilibrated in Buffer B. The column was rinsed with buffer B until the baseline was restored. The column was then rinsed with buffer C (10 mM Tris-HCl (pH 7.0) 50 mM NaCl) until the pH reached 7.0. An NaCl gradient from 50 to 500 mM in buffer C (300 mls total volume) was passed through the column and fractions collected. Those fractions containing activity were pooled and then applied to an immobilized metal affinity chromatography (IMAC) column (2.5 cm ID×10 cm high, Fast-flow Chelating Sepharose, Pharmacia, Sweden) prepared as per the manufacturer's instructions. The column was first pre-treated by rinsing with three column volumes of (one column volume was approximately 50 ml) 0.5 M NaCl, 50 mM EDTA (pH 8.5) to remove all chelated metal ions, 2 M NaCl to remove any ionically bound material, and 1 M NaOH to remove any denatured protein. Copper as 100 mM copper sulfate in 100 mM sodium acetate pH 4.6 was reloaded onto the IMAC column, washed with 20 mM sodium phosphate, 0.5 M NaCl, 50 mM imidazole (pH 7.2) until pH 7.2, and finally equilibrated with five column volumes of 20 mM sodium phosphate, 0.5 M NaCl, 1 mM imidazole for loading. The sample was applied to the column and the column washed with the 1 mM imidazole solution until baseline was restored. A linear gradient formed by 100 mls of 1 mM and 10 mM imidazole solutions (200 mls total volume) was applied, and fractions were collected. All tubes demonstrating higher than background activity were pooled, concentrated, and buffer exchanged into 0.1 M Tris-HCl (pH 7.0) in the Amicon Centricon-10 units as before.

SDS-Page Gels

SDS-Page gels were used to determine purity of protein solutions. Separating gels were made of 10% acrylamide and allowed to gel under butanol. After gelling the butanol was removed and a 4% acrylamide stacking gel was poured on top of the separating gel. Up to 5 $\mu$L of concentrated protein samples were mixed with 20 $\mu$L loading buffer (10% glycerol, 1% SDS, etc.) and boiled for 4 minutes. The 25 $\mu$L samples were loaded onto the gel and run at 200 V for approximately 30 minutes, at which time the loading buffer dye reached the bottom of the gel. The gel was removed from the apparatus and stained using a Coomasie blue stain solution. After staining a minimum of 45 minutes, the Coomasie blue stain was poured off and destain was added. This was allowed to incubate until the solution approximated the color of the gel, at which time the destain was poured off and new destain was added. The gel was then dried and sealed in plastic for further handling.

Protein Concentration Assays

Protein samples were assayed using the Bio-Rad Protein Assay Reagent. The reagent was diluted 1:4 in water and filtered to remove any particulates. 20 $\mu$L of protein sample was combined with 980 $\mu$L of dilute reagent in a 2 mL spectrophotometer cuvette and allowed to incubate for 10–30 minutes. The samples' absorbance was then measured at 595 nm and compared to that of a sample of known enzyme concentration.

Kinetic Assays

Kinetic assays were performed on three substrates: pNPA, LCN-pNP, and p-nitrobenzyl loracarbef nucleus (LCN-pNB). For pNPA and LCN-pNP substrates, final concentrations varying from 0.0625 mM to 16 mM and 0, 15, and 30% DMF in 0.1 M PIPES (pH 7.0) were combined with equal volumes of enzyme samples. These samples were mixed simultaneously in a 96 well plate and monitored with the 96 well plate reader. The absorbance values were recorded, linearly regressed, and then used for calculating kinetic parameters. For the LCN-pNB substrate, final concentrations varying from 0.0156 mM to 8.0 mM and 0, 15 and 30% DMF in PIPES (pH 7.0) were combined with enzyme samples in a quartz cuvette and were measured in a spectrophotometer at 289 nm. All assays were measured in triplicate.

Additionally, assays on pNB containing substrates were performed by adding a reaction mix containing 1.0 mM substrate in 1 to 20% DMF and 0.1 M phosphate buffer (pH 7.0) to a small volume of enzyme solution, incubating at room temperature for 20 to 60 minutes, and then stopping the reaction with an equal volume of acetonitrile. The samples were then injected into an HPLC containing a C18 chromatography column and reaction products were separated using a gradient between 95% 1 mM triethylamine pH 2.5/5% methanol and 100% methanol. The resulting peaks were monitored at 270 nm and recorded on an IBM PC data acquisition system. These peaks were then numerically integrated and used for comparison between enzyme samples.

Directed Evolution of Thermostable Esterases

In the continuation of this example, the p-nitrobenzyl esterase gene was subjected to five generations of random point mutagenesis and screening for increased thermostability. Activity was measured on the pNPA substrate. The production of the yellow-colored para-nitrophenol resulting from hydrolysis of this substrate was monitored in a 96-well plate reader. Thermostable enzymes were identified in a rapid screen which measured the ratio of the residual hydrolytic activity of the mutant enzymes after incubation of the induced cultures at high temperature to their initial activity. Clones displaying less than 20% of the initial activity of the parent were removed from consideration and not analyzed further. Positive mutants (those with high ratio values and greater than 20% of the initial activity) were rescreened in a more thorough assay as set forth below. The best mutants or mutants were then purified and analyzed by differential scanning calorimetry (DSC). The mutant with the highest melting temperature was used to parent the next generation.

The first library was created by mutagenic PCR of the pNB esterase variant 2-19E10 which is identified in the preceding portion of this example. It will be understood that any of the previously described variants can be used in place of 2-19E10 variant. Mutagenic PCR was carried out under conditions that were expected to result in an average of 2 amino acid changes per gene. Screening this library for enhanced thermostability yielded several positive clones, two of which were recombined to create gene 1A5D1 SEQ. ID. NO: 25), which contains 10 DNA changes which encode 5 amino acid changes with respect to wild-type (SEQ. ID. NO: 26) to produce a modified esterase which exhibits a melting temperature ($T_m$) of 57.3° C., as compared to the 52.5° C. $T_m$ of the wild-type enzyme. Gene 1A5D1 (SEQ. ID. NO: 25) was randomly mutated to create a second generation library. The mutant from this library with the highest thermostability index, 2A12 (SEQ. ID. NO: 28), was purified and found to have a $T_m$ of 58.2° C. by DSC. This process was repeated a total of five times, with screening of 500–2,000 clones in each generation.

Screening 1500 clones from the random library prepared from gene 5H3 (SEQ. ID. NO: 33) did not result in any new clones with significant increases in their thermostability. However, a mutant (6H7—SEQ. ID. NO: 35) with a marginal increase in stability was found. A second 6th-generation library was then prepared by using a method for DNA recombination (36). The genes from the five best clones from the 5th generation library were amplified and randomly recombined. Screening 1500 clones from this library yielded a mutant (6sF9—SEQ. ID. NO: 38) more stable than any of its parents ($T_m$=66.5° C.). The amino acid mutations arising from these DNA changes and responsible for the increases in enzyme stability and activity are listed in Table 4. DNA mutations and the codons they are located in are indicated in the left hand column. Amino acid changes arising from non-silent mutations are indicated in the next column. If a gene contains a particular mutation, it is indicated by a "yes" in the table. Table 5 sets forth a summary of the melting temperatures, as measured by differential scanning calorimetry (DSC), of the most stable enzyme from each generation. DSC was performed in 0.1 M PIPES (pH 7.0), and $T_m$ values were determined from the maximum value of the transition.

TABLE 4

| Mutation | AA change | 1A5D1 | 2A12 | 3H5 | 4G4 | 5H3 | 6H7 | 6sF9 |
|---|---|---|---|---|---|---|---|---|
| ATC 27 → ATA | | yes | | | | | | |
| CCC 28 → CCT | | yes | yes | yes | yes | yes | yes | |
| CCT 33 → CCC | | | yes | yes | yes | yes | yes | yes |
| ATT 60 → GTT | Ile 60 Val | yes | yes | yes | yes | yes | yes | yes |
| AAT 96 → AAC | | yes | yes | yes | yes | yes | yes | yes |
| CCT 110 → CTA | | yes | yes | yes | yes | yes | yes | yes |
| GCA 125 → GCG | | | | | | | yes | yes |
| TTG 144 → ATG | Leu 144 Met | yes | yes | yes | yes | yes | yes | yes |
| TTC 274 → CTC | Phe 274 Leu | | | | | yes | yes | |
| TTA 313 → TTC | Leu 313 Phe | | | | | yes | yes | yes |
| CAT 322 → CGT | His 322 Arg | yes | yes | | | | | |
| CAT 322 → TGT | His 322 Cys | | | yes | | | | |

TABLE 4-continued

| Mutation | AA change | 1A5D1 | 2A12 | 3H5 | 4G4 | 5H3 | 6H7 | 6sF9 |
|---|---|---|---|---|---|---|---|---|
| CAT 322 → TAT | His 322 Tyr | | | | yes | yes | yes | yes |
| GCT 343 → GTT | Ala 343 Val | | yes | yes | yes | yes | yes | yes |
| ATG 358 → GTG | Met 358 Val | yes | yes | yes | yes | yes | yes | yes |
| TAT 370 → TTT | Tyr 370 Phe | yes | yes | yes | yes | yes | yes | yes |
| TTT 398 → TTA | Phe 398 Leu | | | | | | yes | |
| GGA 412 → GAG | Gly 412 Glu | | | | | | | yes |
| GGA 412 → GGG | | yes | yes | yes | yes | yes | yes | |
| TCT 429 → TCC | | | | | | | | yes |
| ATC 437 → ACC | Ile 437 Thr | | | yes | yes | yes | yes | yes |

TABLE 5

| Mutant | Melting Temperature (° C.) |
|---|---|
| WT | 52.5 |
| A5D1 | 57.3 |
| 2A12 | 58.2 |
| 3H5 | 62.0 |
| 4G4 | 64.2 |
| 5H3 | 65.1 |
| 6H7 | 65.4 |
| 6sF9 | 66.5 |

In Situ Analysis

Figure 14:
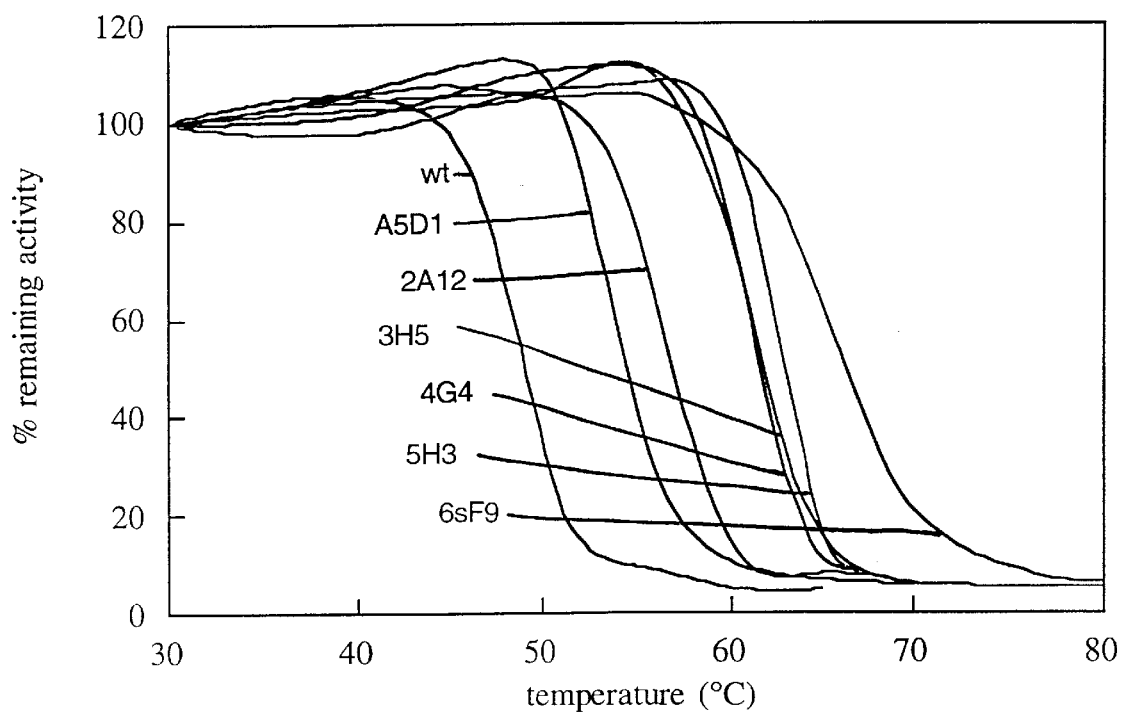
FIG. 14 is a graph showing activities of thermostable variants from successive mutant generations as a function of temperature, measured in situ. Aliquots of induced cultures were incubated at a given temperature for 10 minutes, placed on ice and then assayed in a 96 well plate reader at room temperature for activity towards the pNPA substrate (0.25 mM). The change in OD 405 over time monitored the release of p-nitrophenol and was used as a measure of the enzyme activity. All values for each enzyme are normalized to the value obtained using a 30° C. heat treatment. The temperature at which the enzyme begins to inactivate increases with each successive generation.

After identification by the initial screen, potentially thermostable mutants were regrown and induced. Aliquots of these cultures were incubated for 10 minutes at various temperatures, then assayed for activity at room temperature. FIG. 14 shows the results from these assays for genes selected as parent enzymes from each generation. In each successive generation, the temperature at which the enzyme begins to inactivate increases.

Differential Scanning Calorimetry

Figure 15:
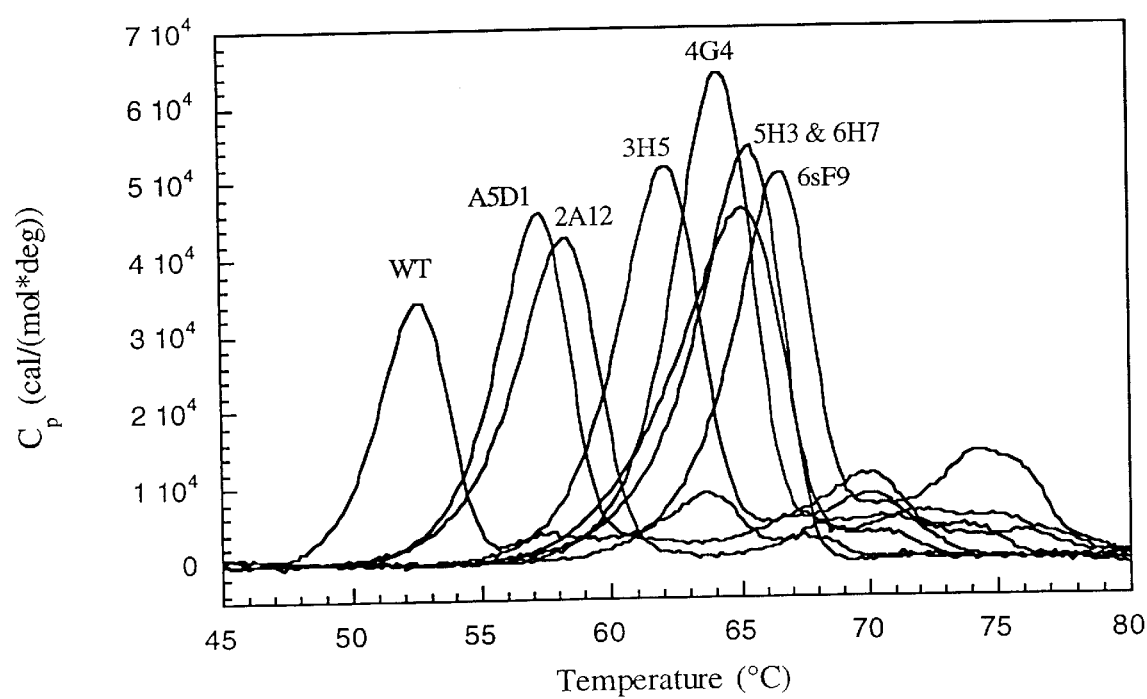
FIG. 15 is a graph showing differential scanning calorimetry (DSC) traces of the wild-type pNB esterase (WT) and the most thermally stable mutants from generations 1 (A5D1) through 6 (6H7 and 6sF9). Analyses were done with purified enzyme (14.5–15.5 $\mu$M) in 0.1 M PIPES (pH 7.0.

Results from the differential scanning calorimetry (DSC) analysis for the most thermostable enzyme from each generation are shown in FIG. 15. Melting temperature values obtained from these data are shown in Table 6. With each successive generation, there is an increase in the $T_m$ of the enzyme. With the exception of mutant 6H7 (SEQ. ID. NO: 36), the change in $T_m$ from parent to daughter is greater than the experimental variation. Mutant 6sF9 (SEQ. ID. NO: 38) has a $T_m$ of 66° C., 14° C. higher than the $T_m$ of the wild-type enzyme.

The reversibility of the thermal denaturation was checked for several mutants by repeating the calorimetric measurements immediately after the first DSC measurement. Even when the first DSC scan was stopped near the top of the first peak, there was no evidence of refolding in the second scan (data not shown). Thus, the irreversible step in the thermal denaturation is not responsible for the second peak seen in the DSC traces (see FIG. 15). This second peak may be due to aggregation.

The irreversibility of pNBE unfolding as demonstrated by the lack of a significant change in heat capacity for heat denatured samples prevents the extraction of free energies from the DSC data. Analysis of the DSC data using the method of Sanchez-Ruiz for irreversible transitions (37; 38) indicates that the thermal denaturation may not be a simple two state irreversible transition.

Activities of the Thermostable Enzymes

Figure 16:
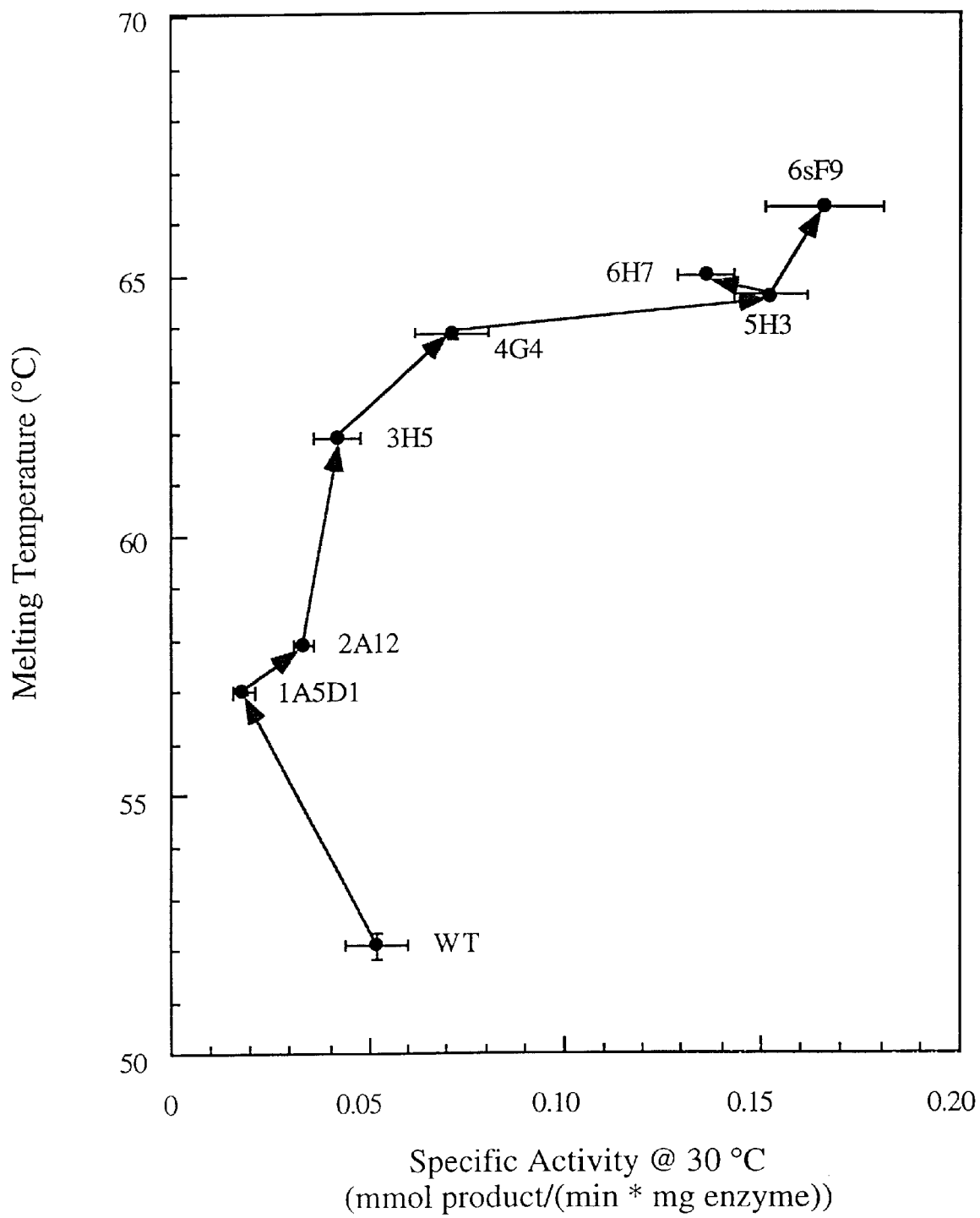
FIG. 16 is a graph showing specific activities and melting temperatures of thermostable mutants from generations 1–6. The $T_m$ of purified enzyme was determined by DSC. Specific activity was determined at 30° C. on p-nitrophenyl acetate (0.25 mM) in 0.1 M PIPES buffer (pH 7.0). Compared to the wild-type, enzymes from the fifth and sixth generations exhibit significant increases in both specific activity and stability.

The in vitro activity of 6sF9 (SEQ. ID. NO: 38) (the sixth generation shuffled mutant) at 30° C. is three times higher than the wild-type specific activity (FIG. 16). The $K_m$ of 6sF9 is three times lower than that of the wild-type pNBE at 30° C. In addition, the $v_{max}$ of 6sF9 is nearly twice that of the wild-type enzyme. Thus, both the substrate binding and the catalytic rate are improved over the wild-type values.

Figure 17:
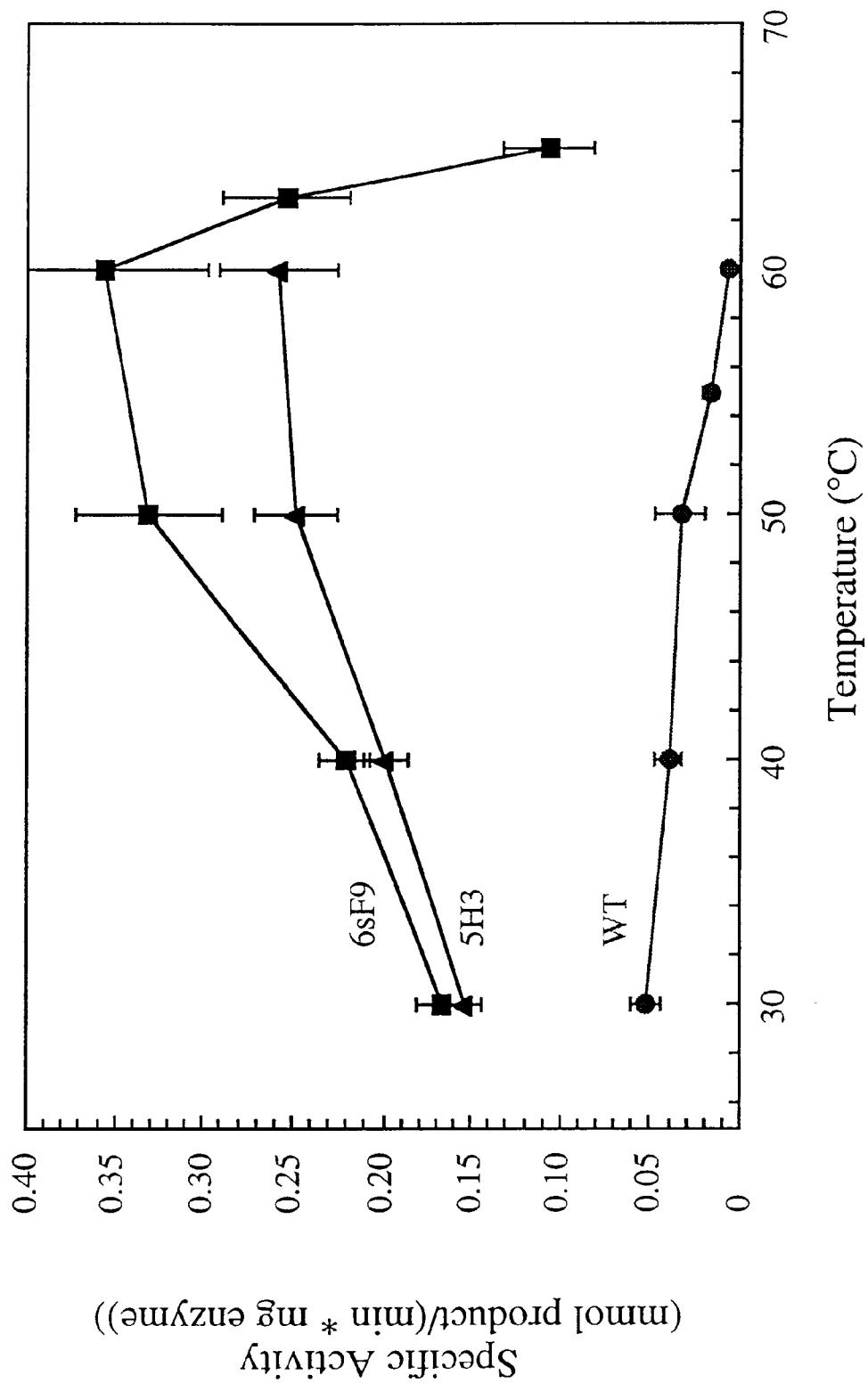
FIG. 17 is a graph showing the dependence of enzyme activity on temperature, for the wild-type (WT) and evolved (5H3, 6sF9) esterases. Activities on p-nitrophenyl acetate (0.25 mM) in 0.1 M PIPES (pH 7.0) were measured spectrophotometrically. While the specific activity of the WT shows no increase with increasing temperature in this range, the specific activity of 6sF9 increases up to 60° C.

The response of the enzymatic activity to temperature is also altered in our evolved enzymes. FIG. 17 shows the activity-temperature profiles for purified fifth (5H3—SEQ. ID. NO: 34) and sixth (6sF9—SEQ. ID. NO: 38) generation enzymes. The activities of the thermostable variants are significantly greater than the wild-type pNBE over the entire temperature range studied. The wild-type pNBE does not show a significant increase in specific activity upon raising the temperature from 30 to 40° C., whereas 6sF9 (SEQ. ID. NO: 38) shows an increase in specific activity of 30 percent upon raising the temperature to 40° C. (see FIG. 17). This increase in activity with temperature continues up to and including 60° C. The optimum temperature for 6sF9 (SEQ. ID. NO: 38) is more than 20° C. higher than the wild-type's despite the lack of selection for activity at high temperatures.

Materials and Methods

Genes, vectors and bacterial strains.

This example used the same basic procedures as the previous example. Plasmid pNB106R was designed by Zock et al. (4) and contains the 1.5 kb wild-type pNBE gene from *Bacillus subtilis* under control of a temperature sensitive promoter. This plasmid was used as the source of the wild-type gene, and for expression and sequencing of all mutants.

Random Mutagenesis

The random mutagenesis procedure was based on the procedure of Cadwell & Joyce (42). Due to the length of the esterase gene, no manganese was required to obtain the desired level of mutagenesis. Primers RM1A (5'-CAATTATCTAGACTACACGAG) (SEQ. ID. NO: 39) and RM2A (5'-GGTGGCTGACACTCGGTGAGG) (SEQ. ID. NO: 40) flank the gene beyond the XbaI and BamH1 restriction sites present in the plasmid. 40 ng of each primer was mixed with 10 ng of the expression plasmid containing the parent esterase gene in a 100 μl PCR reaction. The reaction conditions were as follows: 50 mM KCl, 10 mM Tris (pH 8.5), 0.1% Triton X-100, 7 mM $MgCl_2$, 1 mM dCTP, 1 mM TTP, 0.2 mM dATP, 0.2 mM dGTP, and 5 U Taq polymerase (Promega, Madison, Wis.). The reaction was thermocycled for 25 cycles of 94° C., 1 minute; 45° C., 1 minute; 72° C., 1 minute. Amplification of the 2 kb product was checked by running a small aliquot of the reaction on an agarose gel.

DNA Shuffling

In vitro recombination was based on the method described by Stemmer (36), with modifications in the fragmentation reaction as described by Lorimer and Pastan (39). The five genes selected from the fifth generation were amplified under standard PCR conditions using the primers described above. The amplified DNA was purified using a DNA purification column (Promega, Madison, Wis.), and equimolar amounts of the genes were mixed. 2 µg of this mixture was mixed on ice in a 50 µl reaction containing 50 mM Tris-HCl (pH 7.4), 10 mM $MnCl_2$, and 0.04 units of DNAse I (Boerhinger Mannheim, Indianapolis, Ind.). The reaction was incubated at 15° C. minutes then heated to 90° for 10 minutes to stop the reaction. A small aliquot of the reaction was run on an agarose gel to verify that the digestion was complete and fragment size was close to 50 bp. Fragments were purified on a G50 spin column (Boehringer Mannheim) or Centri-Sep column (Princeton Separations, Adelphia, N.J.). 10 µl of the fragments were reassembled in a 20 µl PCR reaction that contained no primers. Several drops of mineral oil were added to the reaction prior to thermocycling for 40 cycles at: 94° C., 1 minute; 55° C., 1 minute; 72° C., 1 minute+5 second/cycle. Assembly was checked by running 2 µl of the reaction on an agarose gel. If no smear was visible, or if the smear did not contain fragments as large as 2 kb, the reaction was allowed to proceed for an additional 10 cycles. 1 µl of the reassembly reaction was then used as template in a 100 µl standard PCR reaction.

Library production

Products from the mutagenic PCR reactions or shuffling reaction were purified using a DNA purification column (Promega) and cloned (using XbaI and BamHI restriction sites) back into the expression vector using standard molecular biology techniques (40). The resulting plasmids were transformed into freshly prepared (41) electrocompetent TG1 cells, which were plated on LB agar plates containing 20 µg/ml tetracycline. Colonies were picked with sterile toothpicks after 24 hours of growth into a well of a 96-well plate containing 200 µl of 2×YT medium with 20 µg/ml tetracycline. Plates were incubated at 30° C. for 24 hours to allow cell growth. The plates were then duplicated by transferring 5 µl from every well into a new plate containing fresh media and antibiotic. The original plates were stored, and the duplicate plates were grown for an additional 24 hours, after which the temperature was raised to 42° C. to induce expression to esterase variants. After 8 hours, the plates were screened.

Thermostability Screening Assay

For identification of pNBE variants that possessed increased thermostability, a 96-well plate thermostability screening assay was used as described in the previous example. From each well of the induced 96-well plate, 20 µl of cell culture was transferred to the corresponding wells of two new plates. One of these plates was directly assayed for enzyme activity ($A_i$) by the addition of 100 µl of 0.25 mM pNPA in 0.1 M Tris-HCl (pH 7.5). The duplicate plate was heat treated for 10 minutes at a specific temperature, removed from the oven, chilled on ice for 15 minutes, incubated for 30 minutes at room temperature and then assayed for residual activity ($A_r$). The esterase reaction was measured in a 96-well plate reader set at 405 nm to monitor the release of the yellow-colored p-nitrophenol. The ratio between $A_r$ and $A_i$ was determined and used as a stability index for each mutant. The temperature used for the heat treatment of each generation was set at the $T_m$-value for the parent of that generation.

Further Screening

Figure 18:
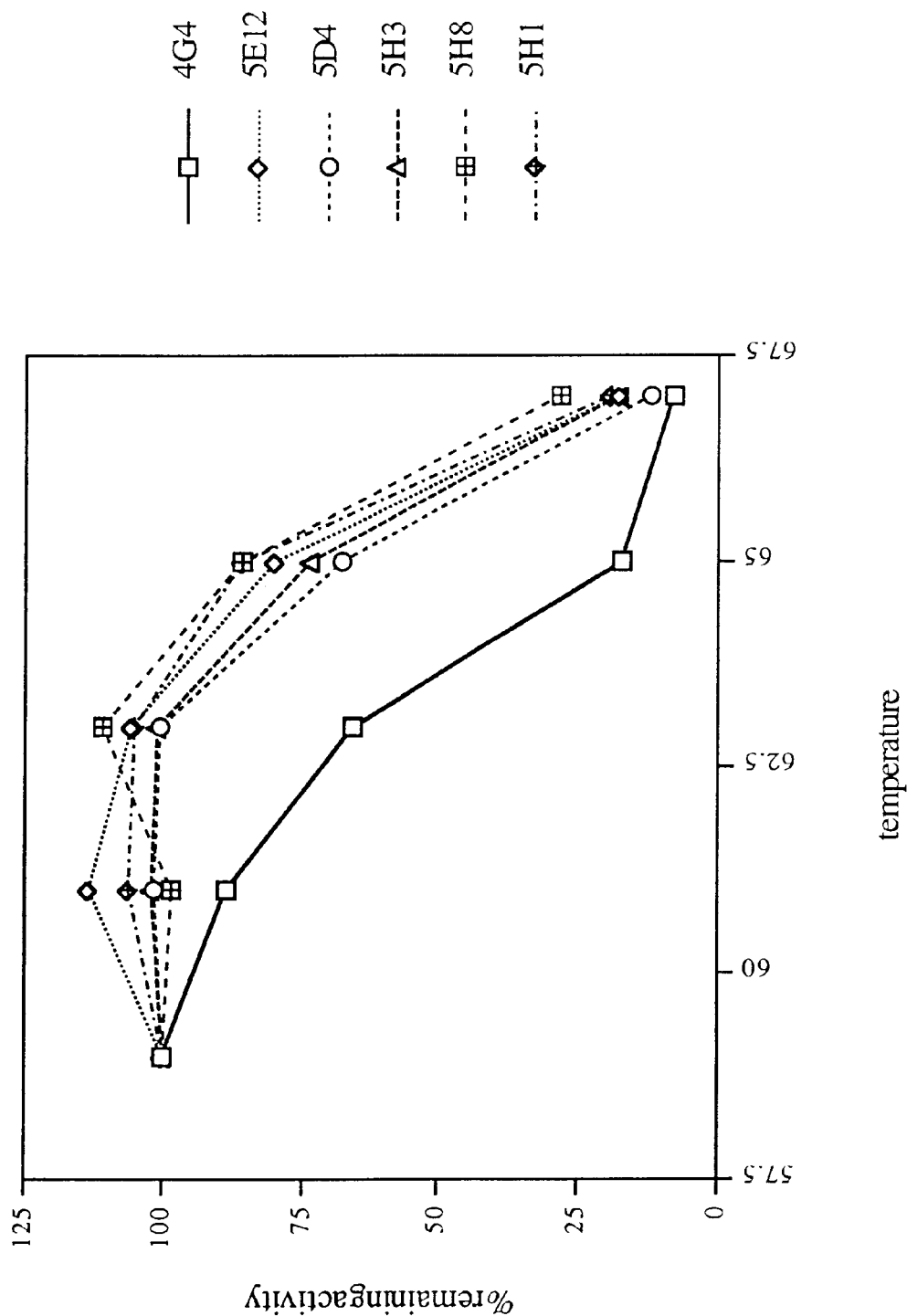
FIG. 18 shows a graph of the activities of the five most thermostable enzymes from the fifth generation as a function of temperature, measured in situ. 4G4 is the parent for the fifth generation. Aliquots of induced culture were incubated at different temperatures for 10 minutes, placed on ice and then assayed in a 96-well plate reader at room temperature for activity towards pNPA (0.25 mM) in 0.1 M Tris (pH 7.5).

The mutants with the highest stability index values were regrown in 5 ml cultures for further analysis. Mutants with less than 20% of the initial activity of the parent enzyme were removed from consideration, regardless of their stability index value. The 5 ml cultures were allowed to grow to saturation, then induced at 42° C. for 8 hours. After induction, 30 µl aliquots of the culture were removed to 500 µl tubes. The tubes were heated for 10 minutes, then placed on ice. Two 10 µl aliquots of the heat treated culture were then transferred to a 96-well plate for the esterase activity assay. Activity values were normalized to the activity at 30° C. and plotted to generate the graphs shown in FIGS. 14 and 18. The mutant from this assay which appeared to have the highest increase in thermostability over the parent enzyme was selected for purification and analysis by DSC.

Enzyme Purification wt pNBE and all variants were purified using a modified version of the procedure used in the previous example. Single colonies were normally inoculated into 5 mls of 2×YT tet culture medium and allowed to grow overnight at 32° C. to high turbidity. 2 mls of this culture was then used to inoculate 2 liters of 2×YT tet medium. The large culture was allowed to grow at 30° C. to saturation and temperature was then shifted to 42° C. for 8–9 hours to induce the production of the pNBE protein. The cells were harvested by centrifugation and resuspended in a buffer solution containing 10 mM Tris-HCl (pH 7.5), 1 mM β-mercaptoethanol, 0.5 mM EDTA and 0.2 mg/ml Lysozyme. This suspension was incubated at 37° C. for 45 minutes and then frozen (in liquid nitrogen) and thawed three times in order to lyse the cells efficiently. To reduce the viscosity of the lysed cell solution, 30 U Dnase I was added and then the solution was centrifuged to pellet the cell debris. The cell lysate supernatant was adjusted to pH 5.0 with 1 M HCl, and the newly formed precipitate was removed by centrifugation. 50% $(NH_4)_2SO_4$ was added to the supernatant, the solution was chilled on ice for 15–20 minutes and subjected to centrifugation. The pellet was removed and the ammonium sulfate concentration of the supernatant was increased to 85% $(NH_4)_2SO_4$ in order to precipitate the pNBE protein. This solution was subject to centrifugation and the pellet was redissolved in 20 mM triethanolamine (pH 7.5) 50 mM NaCl, 1 mM β-mercaptoethanol and 0.5 mM EDTA. The resulting protein solution was applied to a Q sepharose high performance column (Pharmacia, Uppsala, Sweden) preequilibrated with the same buffer. A NaCl gradient from 50 mM to 500 mM in 20 mM triethanolamine (pH 7.5) was passed through the column and fractions exhibiting pNBE activity were collected. These fractions were pooled, desalted and applied to a HiTrap chelating column (Pharmacia, Upsala, Sweden) charged with $Cu^{2+}$ and equilibrated with 20 mM sodium phosphate (pH 7.0) 500 mM NaCl and 1 mM imidazole. An imidazole gradient from 1 to 10 mM was used to elute the pNBE. Fractions exhibiting pNBE activity were analyzed on a SDS PAGE, and samples showing 90% purity or higher was used in further studies.

DSC Measurements

DSC was performed on a MicroCal MC-2 differential scanning micro-calorimeter (MicroCal Inc., Northampton, Mass.) with cell volumes of 1.18 mL, interfaced with an IBM-compatible personal computer. A scanning rate of 1° C./hour and protein concentrations of between 14.5 and 15.5 μM were all used for all experiments. Before measurements, samples were dialyzed for at least 14 hours against 100 mM PIPES (pH 7.0) with one change of buffer and degassed under stirring, in vacuo. The reference cell was filled with degassed buffer from the dialysis step. An over pressure of 2 atm dry nitrogen was maintained over the solutions in the cells throughout the scans to prevent any degassing during heating. Experimental traces were corrected for the calorimeter baseline obtained by scanning the appropriate buffer solution in both cells of this calorimeter. Data were analyzed and plotted using the window-based software package, Origin, supplied by MicroCal Inc.

Enzymatic Activity Assay

The pNBE activity was routinely measaured using p-nitrophenyl acetate as the substrate. 0.2 mM pNPA in 100 mM Tris-HCl (pH 7.5) were used in each case. The rate of the reaction was monitored at $A_{405}$ using a computer controlled plate reader (ThermoMax, Molecular Devices).

Thermal Inactivation Measurements

Thermal deactivation was measured as residual activity after 10 minutes incubation of 40 μl cell suspension at varying temperatures. After the heating step the samples were directly chilled on ice. Reactivation under these conditions could be excluded. 20 μl of the heat treated cell suspension was transferred to a 96-well plate and assayed for enzyme activity. Enzyme activity at 30° C. was used as 100% activity.

The preceding examples demonstrate the usefulness of the present invention in preparing, isolating and identifying esterases which have improved stability and/or ester hydrolysis activity in either aqueous or organic media relative to the natural enzyme.

For example, thermostable mutations can be used advantageously for purification of pNB esterases. Recombinant protein purification from bacterial and other host cells can be greatly simplified if the recombinant protein is significantly more stable than the host cell's proteins. A simple heat treatment will cause many of the host cell proteins to denature and precipitate, while the recombinant protein remains soluble. The soluble protein can then be easily separated from the precipitate, for example by centrifugation or filtration.

Conventional purification of pNB esterase involves an acid precipitation step at pH 5.0 which occurs immediately following cell lysis. In this step contaminating proteins are precipitated but the pNB esterase remains in solution. This is probably the most delicate step of the purification because precipitated protein can interfere with the pH measurement and the pH 7 lysis buffer is not an effective buffer around pH 5. At pHs below 5, the pNB esterase itself may begin to precipitate. Since the thermostable variants can survive heating at temperatures up to 55° C., a heating step provides a robust alternative to the delicate pH precipitation step.

To test this, cell lysates from cells expressing wild-type pNB esterase or mutant 6sF9 (SEQ. ID. NO: 38) were subject to heating at 55° C. After 5 minutes of incubation at 55° C., all of the samples became cloudy due to precipitated protein, and the samples containing wild type pNB esterase lost all of their esterase activity. The samples containing 6sF9 (SEQ. ID. NO: 38) lost two-thirds of activity after 30 minutes at 55° C. For all incubation times, the wild-type showed no pNB esterase bands above the background on an electrophoresis gel, indicating that the pNB esterase had precipitated out of solution. For incubations at 55° C. of 5 minutes and longer, a band corresponding to pNB esterase 6sF9 (SEQ. ID. NO: 38) was clearly visible on the gel. The intensity of this band did not vary with longer incubation time, indicating that the 6sF9 pNB esterase remained in solution.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

---

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 1470 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:

(A) ORGANISM:
        (C) INDIVIDUAL ISOLATE: 0-Wtpnb (ix) FEATURE:
        (A) NAME/KEY: CDS
        (B) LOCATION: complement (1..1470)

(xi) SEQUENCE DESCRIPTION: SEQ ID NO:1:

ATGACTCATC AAATAGTAAC GACTCAATAC GGCAAAGTAA AAGGCACAAC GGAAAACGGC        60

GTACATAAGT GGAAAGGCAT CCCCTATGCC AAGCCGCCTG TCGGACAATG GCGTTTTAAA       120

GCACCTGAGC CGCCTGAAGT GTGGGAAGAT GTCCTTGATG CCACAGCGTA CGGTCCTATT       180

TGCCCGCAGC CGTCTGATTT GCTCTCACTG TCGTATACAG AGCTGCCCCG CCAGTCCGAG       240

GATTGCTTGT ATGTCAATGT ATTTGCGCCT GACACTCCAA GTCAAAATCT TCCTGTCATG       300

GTGTGGATTC ACGGAGGCGC TTTTTATCTT GGAGCGGGCA GTGAGCCATT GTATGACGGA       360

TCAAAACTTG CGGCACAGGG AGAAGTCATT GTCGTTACAT TGAACTATCG GCTGGGGCCG       420

TTTGGCTTTT TGCACTTGTC TTCGTTTGAT GAGGCGTATT CCGATAACCT TGGGCTTTTA       480

GACCAAGCCG CCGCGCTGAA ATGGGTGCGG GAGAATATCT CAGCGTTTGG CGGTGATCCC       540

GATAACGTAA CAGTATTTGG AGAATCCGCC GGCGGCATGA GCATTGCCGC GCTGCTCGCT       600

ATGCCTGCGG CAAAAGGCCT GTTCCAGAAA GCGATCATGG AAAGCGGCGC TTCCCGAACA       660

ATGACAAAAG AACAAGCGGC AAGCACTGCG GCTGCCTTTT TACAGGTCCT TGGGATTAAT       720

GAGAGCCAGC TGGACAGATT GCATACTGTA GCAGCGGAAG ATTTGCTTAA AGCGGCCGAT       780

CAGCTTCGGA TTGCAGAAAA AGAAAATATC TTTCAGCTGT TCTTCCAGCC CGCCCTTGAT       840

CCGAAAACGC TGCCTGAAGA ACCAGAAAAA TCGATCGCAG AAGGGGCTGC TTCCGGCATT       900

CCGCTATTGA TTGGAACAAC CCGTGATGAA GGATATTTAT TTTTCACCCC GGATTCAGAC       960

GTTCATTCTC AGGAAACGCT TGATGCAGCA CTCGAGTATT TACTAGGGAA GCCGCTGGCA      1020

GAGAAAGCTG CCGATTTGTA TCCGCGTTCT CTGGAAAGCC AAATTCATAT GATGACTGAT      1080

TTATTATTTT GGCGCCCTGC CGTCGCCTAT GCATCCGCAC AGTCTCATTA CGCCCCTGTC      1140

TGGATGTACC GGTTCGATTG GCACCCGGAG AAGCCGCCGT ACAATAAAGC GTTTCACGCA      1200

TTAGAGCTTC CTTTTGTCTT TGGAAATCTG GACGGATTGG AACGAATGGC AAAAGCGGAG      1260

ATTACGGATG AGGTGAAACA GCTTTCTCAC ACGATACAAT CCGCGTGGAT CACGTTCGCT      1320

AAAACAGGAA ACCCAAGCAC CGAAGCTGTG AATTGGCCGG CGTATCATGA AGAAACGAGA      1380

GAGACGGTGA TTTTAGACTC AGAGATTACG ATCGAAAACG ATCCCGAATC TGAAAAAAGG      1440

CAGAAGCTAT TCCCTTCAAA AGGAGAATAA                                      1470

(2) INFORMATION FOR SEQ ID NO:2:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:2:

Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

```
Glu Asp Val Leu Asp Ala Thr Ala Tyr Gly Pro Ile Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480
```

Gln Lys Leu Phe Pro Ser Lys Gly Glu
              485

(2) INFORMATION FOR SEQ ID NO:3:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 1-1h9

(ix) FEATURE:
        (A) NAME/KEY: CDS
        (B) LOCATION: complement (1..1470)

(xi) SEQUENCE DESCRIPTION: SEQ ID NO:3:

```
ATGACTCATC AAATAGTAAC GACTCAATAC GGCAAAGTAA AAGGCACAAC GGAAAACGGC      60
GTACATAAGT GGAAAGGCAT CCCTTATGCC AAGCCGCCTG TCGGACAATG GCGTTTTAAA     120
GCACCTGAGC CGCCTGAAGT GTGGGAAGAT GTCCTTGATG CCACAGCGTA CGGTCCTATT     180
TGCCCGCAGC CGTCTGATTT GCTCTCACTG TCGTATACAG AGCTGCCCCG CCAGTCCGAG     240
GATTGCTTGT ATGTCAATGT ATTTGCGCCT GACACTCCAA GTCAAAATCT TCCTGTCATG     300
GTGTGGATTC ACGGAGGCGC TTTTTATCTT GGAGCGGGCA GTGAGCCATT GTATGACGGA     360
TCAAAACTTG CGGCACAGGG AGAAGTCATT GTCGTTACAT TGAACTATCG GCTGGGGCCG     420
TTTGGCTTTT TGCACTTGTC TTCGTTTGAT GAGGCGTATT CCGATAACCT TGGGCTTTTA     480
GACCAAGCCG CCGCGCTGAA ATGGGTGCGG GAGAATATCT CAGCGTTTGG CGGTGATCCC     540
GATAACGTAA CAGTATTTGG AGAATCCGCC GGCGGCATGA GCATTGCCGC GCTGCTCGCT     600
ATGCCTGCGG CAAAAGGCCT GTTCCAGAAA GCGATCATGG AAAGCGGCGC TTCCCGAACA     660
ATGACAAAAG AACAAGCGGC AAGCACTGCG GCTGCCTTTT TACAGGTCCT TGGGATTAAT     720
GAGAGCCAGC TGGACAGATT GCATACTGTA GCAGCGGAAG ATTTGCTTAA AGCGGCCGAT     780
CAGCTTCGGA TTGCAGAAAA AGAAAATATC TTTCAGCTGT TCTTCCAGCC CGCCCTTGAT     840
CCGAAAACGC TGCCTGAAGA ACCAGAAAAA TCGATCGCAG AAGGGGCTGC TTCCGGCATT     900
CCGCTATTGA TTGGAACAAC CCGTGATGAA GGATATTTAT TTTTCACCCC GGATTCAGAC     960
GTTCGTTCTC AGGAAACGCT TGATGCAGCA CTCGAGTATT TACTAGGGAA GCCGCTGGCA    1020
GAGAAAGCTG CCGATTTGTA TCCGCGTTCT CTGGAAAGCC AAATTCATAT GATGACTGAT    1080
TTATTATTTT GGCGCCCTGC CGTCGCCTTT GCATCCGCAC AGTCTCATTA CGCCCCTGTC    1140
TGGATGTACC GGTTCGATTG GCACCCGGAG AAGCCGCCGT ACAATAAAGC GTTTCACGCA    1200
TTAGAGCTTC CTTTTGTCTT TGGAAATCTG GACGGATTGG AACGAATGGC AAAAGCGGAG    1260
ATTACGGATG AGGTGAAACA GCTTTCTCAC ACGATACAAT CCGCGTGGAT CACGTTCGCT    1320
AAAACAGGAA ACCCAAGCAC CGAAGCTGTG AATTGGCCGG CGTATCATGA AGAAACGAGA    1380
GAGACGGTGA TTTTAGACTC AGAGATTACG ATCGAAAACG ATCCCGAATC TGAAAAAAGG    1440
CAGAAGCTAT TCCCTTCAAA AGGAGAATAA                                    1470
```

(2) INFORMATION FOR SEQ ID NO:4:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:4:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Pro Glu Val Trp
         35                  40                  45

Glu Asp Val Leu Asp Ala Thr Ala Tyr Gly Pro Ile Cys Pro Gln Pro
     50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

(2) INFORMATION FOR SEQ ID NO:5:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 2-19E10

(ix) FEATURE:
        (A) NAME/KEY: CDS
        (B) LOCATION: complement (1..1470)

(xi) SEQUENCE DESCRIPTION: SEQ ID NO:5:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCTG TCGGACAATG GCGTTTTAAA     120

GCACCTGAGC CGCCTGAAGT GTGGGAAGAT GTCCTTGATG CCACAGCGTA CGGTCCTATT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAATCT TCCTGTCATG     300

GTGTGGATTC ACGGAGGCGC TTTTTATCTA GGAGCGGGCA GTGAGCCATT GTATGACGGA     360

TCAAAACTTG CGGCACAGGG AGAAGTCATT GTCGTTACAT TGAACTATCG GCTGGGGCCG     420

TTTGGCTTTT TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTAT TTTTCACCCC GGATTCAGAC     960
```

```
GTTCGTTCTC AGGAAACGCT TGATGCAGCA CTCGAGTATT TACTAGGGAA GCCGCTGGCA    1020

GAGAAAGCTG CCGATTTGTA TCCGCGTTCT CTGGAAAGCC AAATTCATAT GGTGACTGAT    1080

TTATTATTTT GGCGCCCTGC CGTCGCCTTT GCATCCGCAC AGTCTCATTA CGCCCCTGTC    1140

TGGATGTACC GGTTCGATTG CACCCGGAG AAGCCGCCGT ACAATAAAGC GTTTCACGCA    1200

TTAGAGCTTC CTTTTGTCTT TGGAAATCTG GACGGGTTGG AACGAATGGC AAAAGCGGAG    1260

ATTACGGATG AGGTGAAACA GCTTTCTCAC ACGATACAAT CCGCGTGGAT CACGTTCGCT    1320

AAAACAGGAA ACCCAAGCAC CGAAGCTGTG AATTGGCCGG CGTATCATGA AGAAACGAGA    1380

GAGACGGTGA TTTTAGACTC AGAGATTACG ATCGAAAACG ATCCCGAATC TGAAAAAAGG    1440

CAGAAGCTAT TCCCTTCAAA AGGAGAATAA                                    1470
```

(2) INFORMATION FOR SEQ ID NO:6:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:6:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Glu Val Trp
            35                  40                  45

Glu Asp Val Leu Asp Ala Thr Ala Tyr Gly Pro Ile Cys Pro Gln Pro
50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
```

|               |               |               |
|---------------|---------------|---------------|
| 260           | 265           | 270           |

Leu Phe Phe Gln Pro Ala Leu Asp Pro Lys Thr Leu Pro Glu Glu Pro
          275                 280                 285

Glu Lys Ser Ile Ala Glu Ala Ala Ser Gly Ile Pro Leu Leu Ile
290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
              325                 330                 335

Lys Pro Leu Ala Glu Lys Ala Ala Asp Leu Tyr Pro Arg Ser Leu Glu
              340                 345                 350

Ser Gln Ile His Met Val Thr Asp Leu Leu Phe Trp Arg Pro Ala Val
              355                 360                 365

Ala Phe Ala Ser Ala Gln Ser His Tyr Ala Pro Val Trp Met Tyr Arg
370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                    405                 410                 415

Ala Lys Ala Glu Ile Thr Asp Glu Val Lys Gln Leu Ser His Thr Ile
              420                 425                 430

Gln Ser Ala Trp Ile Thr Phe Ala Lys Thr Gly Asn Pro Ser Thr Glu
              435                 440                 445

Ala Val Asn Trp Pro Ala Tyr His Glu Glu Thr Arg Glu Thr Val Ile
450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
              485

(2) INFORMATION FOR SEQ ID NO:7:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 3-10c4

(ix) FEATURE:
        (A) NAME/KEY: CDS
        (B) LOCATION: complement (1..1470)

(xi) SEQUENCE DESCRIPTION: SEQ ID NO:7:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCTG TCGGACAATG GCGTTTTAAA     120

GCACCTGAGC CGCCTGAAGT GTGGGAAGAT GTCCTTGATG CCACAGCGTA CGGTCCTATT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAACCT TCCTGTCATG     300

GTGTGGATTC ACGGAGGCGC TTTTTATCTA GGAGCGGGCA GTGAGCCATT GTATGACGGA     360
```

```
TCAAAACTTG CGGCACAGGG AGAAGTCATT GTCGTTACAT TGAACTATCG GCTGGGGCCG      420

TTTGGCTTTA TGCACTTGTC TTCGTTTGAT GAGGCGTATT CCGATAACCT TGGGCTTTTA      480

GACCAAGCCG CCGCGCTGAA ATGGGTGCGG GAGAATATCC AGCGTTTGG CGGTGATCCC      540

GATAACGTAA CAGTATTTGG AGAATCCGCC GGCGGCATGA GCATTGCCGC GCTGCTCGCT      600

ATGCCTGCGG CAAAAGGCCT GTTCCAGAAA GCGATCATGG AAAGCGGCGC TTCCCGAACA      660

ATGACAAAAG AACAAGCGGC AAGCACTGCG GCTGCCTTTT TACAGGTCCT TGGGATTAAT      720

GAGAGCCAGC TGGACAGATT GCATACTGTA GCAGCGGAAG ATTTGCTTAA AGCGGCCGAT      780

CAGCTTCGGA TTGCAGAAAA AGAAAATATC TTTCAGCTGT TCTTCCAGCC CGCCCTTGAT      840

CCGAAAACGC TGCCTGAAGA ACCAGAAAAA TCGATCGCAG AAGGGGCTGC TTCCGGCATT      900

CCGCTATTGA TTGGAACAAC CCGTGATGAA GGATATTTAT TTTTCACCCC GGATTCAGAC      960

GTTCGTTCTC AGGAAACGCT TGATGCAGCA CTCGAGTATT TACTAGGGAA GCCGCTGGCA     1020

GAGAAAGCTG CCGATTTGTA TCCGCGTTCT CTGGAAAGCC AAATTCATAT GGTGACTGAT     1080

TTATTATTTT GGCGCCCTGC CGTCGCCTTT GCATCCGCAC AGTCTCATTA CGCCCCTGTC     1140

TGGATGTACC GGTTCGATTG GCACCCGGAG AAGCCGCCGT ACAATAAAGC GTTTCACGCA     1200

TTAGAGCTTC CTTTTGTCTT TGGAAATCTG GACGGGTTGG AACGAATGGC AAAAGCGGAG     1260

ATTACGGATG AGGTGAAACA GCTTTCTCAC ACGATACAAT CCGCGTGGAT CACGTTCGCT     1320

AAAACAGGAA ACCCAAGCAC CGAAGCTGTG AATTGGCCGG CGTATCATGA AGAAACGAGA     1380

GAGACGGTGA TTTTAGACTC AGAGATTACG ATCGAAAACG ATCCCGAATC TGAAAAAAGG     1440

CAGAAGCTAT TCCCTTCAAA AGGAGAATAA                                      1470
```

(2) INFORMATION FOR SEQ ID NO:8:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:8:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Glu Val Trp
        35                  40                  45

Glu Asp Val Leu Asp Ala Thr Ala Tyr Gly Pro Ile Cys Pro Gln Pro
50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
            165                 170                 175
Gly Gly Asp Pro Asp Asn Val Thr Val Phe Gly Glu Ser Ala Gly Gly
            180                 185                 190
Met Ser Ile Ala Ala Leu Leu Ala Met Pro Ala Ala Lys Gly Leu Phe
            195                 200                 205
Gln Lys Ala Ile Met Glu Ser Gly Ala Ser Arg Thr Met Thr Lys Glu
            210                 215                 220
Gln Ala Ala Ser Thr Ala Ala Ala Phe Leu Gln Val Leu Gly Ile Asn
225                 230                 235                 240
Glu Ser Gln Leu Asp Arg Leu His Thr Val Ala Ala Glu Asp Leu Leu
            245                 250                 255
Lys Ala Ala Asp Gln Leu Arg Ile Ala Glu Lys Glu Asn Ile Phe Gln
            260                 265                 270
 Leu Phe Phe Gln Pro Ala Leu Asp Pro Lys Thr Leu Pro Glu Glu Pro
            275                 280                 285
Glu Lys Ser Ile Ala Glu Gly Ala Ala Ser Gly Ile Pro Leu Leu Ile
            290                 295                 300
Gly Thr Thr Arg Asp Glu Gly Tyr Leu Phe Phe Thr Pro Asp Ser Asp
305                 310                 315                 320
Val Arg Ser Gln Glu Thr Leu Asp Ala Ala Leu Glu Tyr Leu Leu Gly
            325                 330                 335
Lys Pro Leu Ala Glu Lys Ala Ala Asp Leu Tyr Pro Arg Ser Leu Glu
            340                 345                 350
Ser Gln Ile His Met Val Thr Asp Leu Leu Phe Trp Arg Pro Ala Val
            355                 360                 365
Ala Phe Ala Ser Ala Gln Ser His Tyr Ala Pro Val Trp Met Tyr Arg
            370                 375                 380
Phe Asp Trp His Pro Glu Lys Pro Pro Tyr Asn Lys Ala Phe His Ala
385                 390                 395                 400
Leu Glu Leu Pro Phe Val Phe Gly Asn Leu Asp Gly Leu Glu Arg Met
            405                 410                 415
Ala Lys Ala Glu Ile Thr Asp Glu Val Lys Gln Leu Ser His Thr Ile
            420                 425                 430
Gln Ser Ala Trp Ile Thr Phe Ala Lys Thr Gly Asn Pro Ser Thr Glu
            435                 440                 445
Ala Val Asn Trp Pro Ala Tyr His Glu Glu Thr Arg Glu Thr Val Ile
            450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
            485

(2) INFORMATION FOR SEQ ID NO:9:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
```

(A) ORGANISM:
(C) INDIVIDUAL ISOLATE: 4-38b9

(ix) FEATURE:
(A) NAME/KEY: CDS
(B) LOCATION: complement (1..1470)

(xi) SEQUENCE DESCRIPTION: SEQ ID NO:9:

| | |
|---|---:|
| ATGACTCATC AAATAGTAAC GACTCAATAC GGCAAAGTAA AAGGCACAAC GGAAAACGGC | 60 |
| GTACATAAGT GGAAAGGCAT CCCTTATGCC AAGCCGCCTG TCGGACAATG GCGTTTTAAA | 120 |
| GCACCTGAGC CGCCTGAAGT GTGGGAAGAT GTCCTTGATG CCACAGCGTA CGGTCCTGTT | 180 |
| TGCCCGCAGC CGTCTGATTT GCTCTCACTG TCGTATACAG AGCTGCCCCG CCAGTCCGAG | 240 |
| GATTGCTTGT ATGTCAATGT ATTTGCGCCT GACACTCCAA GTCAAAACCT TCCTGTCATG | 300 |
| GTGTGGATTC ACGGAGGCGC TTTTTATCTA GGAGCGGGCA GTGAGCCATT GTATGACGGA | 360 |
| TCAAAACTTG CGGCACAGGG AGAAGTCATT GTCGTTACAT GAACTATCG GCTGGGGCCG | 420 |
| TTTGGCTTTA TGCACTTGTC TTCGTTTGAT GAGGCGTATT CCGATAACCT TGGGCTTTTA | 480 |
| GACCAAGCCG CCGCGCTGAA ATGGGTGCGG GAGAATATCT CAGCGTTTGG CGGTGATCCC | 540 |
| GATAACGTAA CAGTATTTGG AGAATCCGCC GGCGGCATGA GCATTGCCGC GCTGCTCGCT | 600 |
| ATGCCTGCGG CAAAAGGCCT GTTCCAGAAA GCGATCATGG AAAGCGGCGC TTCCCGAACA | 660 |
| ATGACAAAAG AACAAGCGGC AAGCACTGCG GCTGCCTTTT TACAGGTCCT TGGGATTAAT | 720 |
| GAGAGCCAGC TGGACAGATT GCATACTGTA GCAGCGGAAG ATTTGCTTAA AGCGGCCGAT | 780 |
| CAGCTTCGGA TTGCAGAAAA AGAAAATATC TTTCAGCTGT TCTTCCAGCC CGCCCTTGAT | 840 |
| CCGAAAACGC TGCCTGAAGA ACCAGAAAAA TCGATCGCAG AAGGGGCTGC TTCCGGCATT | 900 |
| CCGCTATTGA TTGAACAAC CCGTGATGAA GGATATTTAT TTTTCACCCC GGATTCAGAC | 960 |
| GTTCGTTCTC AGGAAACGCT TGATGCAGCA CTCGAGTATT TACTAGGGAA GCCGCTGGCA | 1020 |
| GAGAAAGCTG CCGATTTGTA TCCGCGTTCT CTGGAAAGCC AAATTCATAT GGTGACTGAT | 1080 |
| TTATTATTTT GGCGCCCTGC CGTCGCCTTT GCATCCGCAC AGTCTCATTA CGCCCCTGTC | 1140 |
| TGGATGTACC GGTTCGATTG GCACCCGGAG AAGCCGCCGT ACAATAAAGC GTTTCACGCA | 1200 |
| TTAGAGCTTC CTTTTGTCTT TGGAAATCTG GACGGGTTGG AACGAATGGC AAAAGCGGAG | 1260 |
| ATTACGGATG AGGTGAAACA GCTTTCTCAC ACGATACAAT CCGCGTGGAT CACGTTCGCT | 1320 |
| AAAACAGGAA ACCCAAGCAC CGAAGCTGTG AATTGGCCGG CGTATCATGA AGAAACGAGA | 1380 |
| GAGACGGTGA TTTTAGACTC AGAGATTACG ATCGAAAACG ATCCCGAATC TGAAAAAAGG | 1440 |
| CAGAAGCTAT TCCCTTCAAA AGGAGAATAA | 1470 |

(2) INFORMATION FOR SEQ ID NO:10:

(i) SEQUENCE CHARACTERISTICS:
(A) LENGTH: 489 amino acids
(B) TYPE: amino acid
(D) TOPOLOGY: linear (ii) MOLECULE TYPE: enzyme (xi) SEQUENCE DESCRIPTION: SEQ ID NO:10:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45
```

-continued

```
Glu Asp Val Leu Asp Ala Thr Ala Tyr Gly Pro Val Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Thr Leu Asn Tyr Arg Leu Gly Pro Phe Gly Phe Met
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480
```

Gln Lys Leu Phe Pro Ser Lys Gly Glu
            485

(2) INFORMATION FOR SEQ ID NO:11:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 4-43e7

(ix) FEATURE:
        (A) NAME/KEY: CDS
        (B) LOCATION: complement (1..1470)

(xi) SEQUENCE DESCRIPTION: SEQ ID NO:11:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCTG TCGGACAATG GCGTTTTAAA     120

GCACCTGAGC CGCCTGAAGT GTGGGAAGAT GTCCTTGATG CCACAGCGTA CGGTCCTATT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAG GTCAAAACCT TCCTGTCATG     300

GTGTGGATTC ACGGAGGCGC TTTTTATCTA GGAGCGGGCA GTGAGCCATT GTATGACGGA     360

TCAAAACTTG CGGCACAGGG AGAAGTCATT GTCGTTACAT TGAACTATCG GCTGGGGCCG     420

TTTGGCTTTA TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTAT TTTTCACCCC GGATTCAGAC     960

GTTCGTTCTC AGGAAACGCT TGATGCAGCA CTCGAGTATT TACTAGGGAA GCCGCTGGCA    1020

GAGAAAGCTG CCGATTTGTA TCCGCGTTCT CTGGAAAGCC AAATTCATAT GGTGACTGAT    1080

TTATTATTTT GGCGCCCTGC CGTCGCCTTT GCATCCGCAC AGTCTCATTA CGCCCCTGTC    1140

TGGATGTACC GGTTCGATTG GCACCCGGAG AAGCCGCCGT ACAATAAAGC GTTTCACGCA    1200

TTAGAGCTTC CTTTTGTCTT TGGAAATCTG GACGGGTTGG AACGAATGGC AAAAGCGGAG    1260

ATTACGGATG AGGTGAAACA GCTTTCTCAC ACGATACAAT CCGCGTGGAT CACGTTCGCT    1320

AAAACAGGAA ACCCAAGCAC CGAAGCTGTG AATTGGCCGG CGTATCATGA AGAAACGAGA    1380

GAGACGGTGA TTTTAGACTC AGAGATTACG ATCGAAAACG ATCCCGAATC TGAAAAAAGG    1440

CAGAAGCTAT TCCCTTCAAA AGGAGAATAA                                    1470
```

(2) INFORMATION FOR SEQ ID NO:12:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:12:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Gly Gln Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Val Leu Gly
                325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365
```

|     |     |     |     |     |     |     |     |     |     |     |     |
| --- | --- | --- | --- | --- | --- | --- | --- | --- | --- | --- | --- |
| Ala | Phe | Ala | Ser | Ala | Gln | Ser | His | Tyr | Ala | Pro | Val | Trp | Met | Tyr | Arg |
|     | 370 |     |     |     | 375 |     |     |     |     | 380 |     |

Phe Asp Trp His Pro Glu Lys Pro Pro Tyr Asn Lys Ala Phe His Ala
385                     390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465             470                 475                 480

Gln Lys Leu Phe Pro Ser Lys Gly Glu
                485

(2) INFORMATION FOR SEQ ID NO:13:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 4-54b9

(ix) FEATURE:
        (A) NAME/KEY: CDS
        (B) LOCATION: complement (1..1470)

(xi) SEQUENCE DESCRIPTION: SEQ ID NO:13:

| | | | | | |
|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCCG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |
| GATTGCTTGT | ATGTCAATGT | ATTTGCGCCT | GACACTCCAA | GTCAAAACCT | TCCTGTCATG | 300 |
| GTGTGGATTC | ACGGAGGCGC | TTTTTATCTA | GGAGCGGGCA | GTGAGCCATT | GTATGACGGA | 360 |
| TCAAAACTTG | CGGCACAGGG | AGAAGTCATT | GTCGTTACAT | TGAACTATCG | GCTGGGGCCG | 420 |
| TTTGGCTTTA | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATTAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | TTTCAGCTGT | TCTTCCAGCC | CGCCCTTGAT | 840 |
| CCGAAAACGC | TGCCTGAAGA | ACCAGAAAAA | TCGATCGCAG | AAGGGGCTGC | TTCCGGCATT | 900 |
| CCGCTATTGA | TTGGAACAAC | CCGTGATGAA | GGATATTTAT | TTTTCACCCC | GGATTCAGAC | 960 |

```
GTTCGTTCTC AGGAAACGCT TGATGCAGCA CTCGAGTATT TACTAGGGAA GCCGCTGGCA   1020

GAGAAAGCTG CCGATTTGTA TCCGCGTTCT CTGGAAAGCC AAATTCATAT GGTGACTGAT   1080

TTATTATTTT GGCGCCCTGC CGTCGCCTTT GCATCCGCAC AGTCTCATTA CGCCCCTGTC   1140

TGGATGTACC GGTTCGATTG GCACCCGGAG AAGCCGCCGT ACAATAAAGC GTTTCACGCA   1200

TTAGAGCTTC CTTTTGTCTT TGGAAATCTG GACGGGTTGG AACGAATGGC AAAAGCGGAG   1260

ATTACGGATG AGGTGAAACA GCTTTCTCAC ACGATACAAT CCGCGTGGAT CACGTTCGCT   1320

AAAACAGGAA ACCCAAGCAC CGAAGCTGTG AATTGGCCGG CGTATCATGA AGAAACGAGA   1380

GAGACGGTGA TTTTAGACTC AGAGATTACG ATCGAAAACG ATCCCGAATC TGAAAAAAGG   1440

CAGAAGCTAT TCCCTTCAAA AGGAGAATAA                                   1470
```

(2) INFORMATION FOR SEQ ID NO:14:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:14:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Glu Val Trp
         35                  40                  45

Glu Asp Val Leu Asp Ala Thr Ala Tyr Gly Pro Ile Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Arg Glu Asn Ile Phe Gln
```

|     |     |     | 260 |     |     |     | 265 |     |     |     | 270 |     |
| --- | --- | --- | --- | --- | --- | --- | --- | --- | --- | --- | --- | --- |

Leu Phe Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Ser Leu Gly
            325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
            355                 360                 365

Ala Phe Ala Ser Ala Gln Ser His Tyr Ala Pro Val Trp Met Tyr Arg
            370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                    405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
            485

(2) INFORMATION FOR SEQ ID NO:15:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 2-13f3

(ix) FEATURE:
        (A) NAME/KEY: CDS
        (B) LOCATION: complement (1..1470)

(xi) SEQUENCE DESCRIPTION: SEQ ID NO:15:

ATGACTCATC AAATAGTAAC GACTCAATAC GGCAAAGTAA AAGGCACAAC GGAAAACGGC    60

GTACATAAGT GGAAAGGCAT CCCTTATGCC AAGCCGCCTG TCGGACAATG GCGTTTTAAA   120

GCACCTGAGC CGCCTGAAGT GTGGGAAGAT GTCCTTGATG CCACAGCGTA CGGTCCTATT   180

TGCCCGCAGC CGTCTGATTT GCTCTCACTG TCGTATACAG AGCTGCCCCG CCAGTCCGAG   240

GATTGCTTGT ATGTCAATGT ATTTGCGCCT GACACTCCAA GTCAAAGTCT TCCTGTCATG   300

GTGTGGATTC ACGGAGGCGC TTTTTATCTT GGAGCGGGCA GTGAGCCATT GTATGACGGA   360

```
TCAAAACTTG CGGCACAGGG AGAAGTCATT GTCGTTACAT TGAACTATCG GCTGGGGCCG      420

TTTGGCTTTT TGCACTTGTC TTCGTTTGAT GAGGCGTATT CCGATAACCT TGGGCTTTTA      480

GACCAAGCCG CCGCGCTGAA ATGGGTGCGG GAGAATATCT CAGCGTTTGG CGGTGATCCC      540

GATAACGTAA CAGTATTTGG AGAATCCGCC GGCGGCATGA GCATTGCCGC GCTGCTCGCT      600

ATGCCTGCGG CAAAAGGCCT GTTCCAGAAA GCGATCATGG AAAGCGGCGC TTCCCGAACA      660

ATGACAAAAG AACAAGCGGC AAGCACTGCG GCTGCCTTTT TACAGGTCCT TGGGATTAAT      720

GAGAGCCAGC TGGACAGATT GCATACTGTA GCAGCGGAAG ATTTGCTTAA AGCGGCCGAT      780

CAGCTTCGGA TTGCAGAAAA AGAAAATATC TTTCAGCTGT TCTTCCAGCC CGCCCTTGAT      840

CCGAAAACGC TGCCTGAAGA ACCAGAAAAA TCGATCGCAG AAGGGGCTGC TTCCGGCATT      900

CCGCTATTGA TTGGAACAAC CCGTGATGAA GGATATTTAT TTTTCACCCC GGATTCAGAC      960

GTTCGTTCTC AGGAAACGCT TGATGCAGCA CTCGAGTATT TACTAGGGAA GCCGCTGGCA     1020

GAGAAAGCTG CCGATTTGTA TCCGCGTTCT CTGGAAAGCC AAATTCATAT GGTGACTGAT     1080

TTATTATTTT GGCGCCCTGC CGTCGCCTTT GCATCCGCGC AGTCTCATTA CGCCCCTGTC     1140

TGGATGTACC GGTTCGATTG GCACCCGGAG AAGCCGCCGT ACAATAAAGC GTTTCACGCA     1200

TTAGAGCTTC CTTTTGTCTT TGGGAATCTG GACGGATTGG AACGAATGGC AAAAGCGGAG     1260

ATTACGGATG AGGTGAAACA GCTTTCTCAC ACGATACAGT CCGCGTGGAT CACGTTCGCT     1320

AAAACAGGAA ACCCAAGCAC CGAAGCTGTG AATTGGCCGG CGTATCATGA AGAAACGAGA     1380

GAGACGGTGA TTTTAGACTC AGAGATTACG ATCGAAAACG ATCCCGAATC TGAAAAAAGG     1440

CAGAAGCTAT TCCCTTCAAA AGGAGAATAA                                     1470
```

(2) INFORMATION FOR SEQ ID NO:16:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:16:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Ser
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
                165                 170                 175
Gly Gly Asp Pro Asp Asn Val Thr Val Phe Gly Glu Ser Ala Gly Gly
            180                 185                 190
Met Ser Ile Ala Ala Leu Leu Ala Met Pro Ala Ala Lys Gly Leu Phe
        195                 200                 205
Gln Lys Ala Ile Met Glu Ser Gly Ala Ser Arg Thr Met Thr Lys Glu
    210                 215                 220
Gln Ala Ala Ser Thr Ala Ala Ala Phe Leu Gln Val Leu Gly Ile Asn
225                 230                 235                 240
Glu Ser Gln Leu Asp Arg Leu His Thr Val Ala Ala Glu Asp Leu Leu
                245                 250                 255
Lys Ala Ala Asp Gln Leu Arg Ile Ala Glu Lys Glu Asn Ile Phe Gln
                260                 265                 270
Leu Phe Phe Gln Pro Ala Leu Asp Pro Lys Thr Leu Pro Glu Glu Pro
            275                 280                 285
Glu Lys Ser Ile Ala Glu Gly Ala Ala Ser Gly Ile Pro Leu Leu Ile
    290                 295                 300
Gly Thr Thr Arg Asp Glu Gly Tyr Leu Phe Phe Thr Pro Asp Ser Asp
305                 310                 315                 320
Val Arg Ser Gln Glu Thr Leu Asp Ala Ala Leu Glu Tyr Leu Leu Gly
                325                 330                 335
Lys Pro Leu Ala Glu Lys Ala Ala Asp Leu Tyr Pro Arg Ser Leu Glu
                340                 345                 350
Ser Gln Ile His Met Val Thr Asp Leu Leu Phe Trp Arg Pro Ala Val
            355                 360                 365
Ala Phe Ala Ser Ala Gln Ser His Tyr Ala Pro Val Trp Met Tyr Arg
        370                 375                 380
Phe Asp Trp His Pro Glu Lys Pro Pro Tyr Asn Lys Ala Phe His Ala
385                 390                 395                 400
Leu Glu Leu Pro Phe Val Phe Gly Asn Leu Asp Gly Leu Glu Arg Met
                405                 410                 415
Ala Lys Ala Glu Ile Thr Asp Glu Val Lys Gln Leu Ser His Thr Ile
                420                 425                 430
Gln Ser Ala Trp Ile Thr Phe Ala Lys Thr Gly Asn Pro Ser Thr Glu
            435                 440                 445
Ala Val Asn Trp Pro Ala Tyr His Glu Glu Thr Arg Glu Thr Val Ile
        450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
                485

(2) INFORMATION FOR SEQ ID NO:17:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
```

(A) ORGANISM:
(C) INDIVIDUAL ISOLATE: 2-23e1

(ix) FEATURE:
(A) NAME/KEY: CDS
(B) LOCATION: complement (1..1470)

(xi) SEQUENCE DESCRIPTION: SEQ ID NO:17:

| | |
|---|---|
| ATGACTCATC AAATAGTAAC GACTCAATAC GGCAAAGTAA AAGGCACAAC GGAAAACGGC | 60 |
| GTACATAAGT GGAAAGGCAT CCCTTATGCC AAGCCGCCTG TCGGACAATG GCGTTTTAAA | 120 |
| GCACCTGAGC CGCCTGAAGT GTGGGAAGAT GTCCTTGATG CCACAGCGTA CGGTCCTATT | 180 |
| TGCCCGCAGC CGTCTGATTT GCTCTCACTG TCGTATACAG AGCTGCCCCG CCAGTCCGAG | 240 |
| GATTGCTTGT ATGTCAATGT ATTTGCGCCT GACACTCCAA GTCAAAATCT TCCTGTCATG | 300 |
| GTGTGGATTC ACGGAGGCGC TTTTTATCTT GGAGCGGGCA GTGAGCCATT GTATGACGGA | 360 |
| TCAAAACTTG CGGCACAGGG AGAAGTCATT GTCGTCACAT TGAACTATCG GCTGGGGCCG | 420 |
| TTTGGCTTTT TGCACTTGTC TTCGTTTGAT GAGGCGTATT CCGATAACCT TGGGCTTTTA | 480 |
| GACCAAGCCG CCGCGCTGAA ATGGGTGCGG GAGAATATCT CAGCGTTTGG CGGTGATCCC | 540 |
| GATAACGTAA CAGTATTTGG AGAATCCGCC GGCGGCATGA GCATTGCCGC GCTGCTCGCT | 600 |
| ATGCCTGCGG CAAAAGGCCT GTTCCAGAAA GCGATCATGG AAAGCGGCGC TTCCCGAACA | 660 |
| ATGACAAAAG AACAAGCGGC AAGCACTGCG GCTGCCTTTT TACAGGTCCT TGGGATTAAT | 720 |
| GAGAGCCAGC TGGACAGATT GCATACTGTA GCAGCGGAAG ATTTGCTTAA AGCGGCCGAT | 780 |
| CAGCTTCGGA TTGCAGAAAA AGAAAATATC CTTCAGCTGT TCTTCCAGCC CGCCCTTGAT | 840 |
| CCGAAAACGC TGCCTGAAGA ACCAGAAAAA TCGATCGCAG AAGGGGCTGC TTCCGGCATT | 900 |
| CCGCTATTGA TTGAACAAC CCGTGATGAA GGATATTTAT TTTTCACCCC GGATTCAGAC | 960 |
| GTTCGTTCTC AGGAAACGCT TGATGCAGCA CTCGAGTATT TACTAGGGAA GCCGCTGGCA | 1020 |
| GAGAAAGTTG CCGATTTGTA TCCGCGTTCT CTGGAAAGCC AAATTCATAT GATGACTGAT | 1080 |
| TTATTATTTT GGCGCCCTGC CGTCGCCTTT GCATCCGCAC AGTCTCATTA CGCCCCTGTC | 1140 |
| TGGATGTACC GGTTCGATTG GCACCCGGAG AAGCCGCCGT ACAATAAAGC GTTTCACGCA | 1200 |
| TTAGAGCTTC CTTTTGTCTT TGGAAATCTG GACGGATTGG AACGAATGGC AAAAGCGGAG | 1260 |
| ATTACGGATG AGGTGAAACA GCTTTCTCAC ACGATACAAT CCGCGTGGAT CACGTTCGCT | 1320 |
| AAAACAGGAA ACCCAAGCAC CGAAGCTGTG AATTGGCCGG CGTATCATGA AGAAACGAGA | 1380 |
| GAGACGGTGA TTTTAGACTC AGAGATTACG ATCGAAAACG ATCCCGAATC TGAAAAAAGG | 1440 |
| CAGAAGCTAT TCCCTTCAAA AGGAGAATAA | 1470 |

(2) INFORMATION FOR SEQ ID NO:18:

(i) SEQUENCE CHARACTERISTICS:
(A) LENGTH: 489 amino acids
(B) TYPE: amino acid
(D) TOPOLOGY: linear (ii) MOLECULE TYPE: enzyme (xi) SEQUENCE DESCRIPTION: SEQ ID NO:18:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Pro Glu Val Trp
         35                  40                  45
```

-continued

```
Glu Asp Val Leu Asp Ala Thr Ala Tyr Gly Pro Ile Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Leu
130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Leu Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
     290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Phe Ala Ser Ala Gln Ser His Tyr Ala Pro Val Trp Met Tyr Arg
370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
450                 455                 460

Leu Asp Ser Glu Ile Thr Ile Glu Asn Asp Pro Glu Ser Glu Lys Arg
465                 470                 475                 480
```

Gln Lys Leu Phe Pro Ser Lys Gly Glu
                485

(2) INFORMATION FOR SEQ ID NO:19:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 4-53d5

(ix) FEATURE:
        (A) NAME/KEY: CDS
        (B) LOCATION: complement (1..1470)

(xi) SEQUENCE DESCRIPTION: SEQ ID NO:19:

| | | | | | |
|---|---|---|---|---|---|
| ATGACTCATC | AAATAGTAAC | GACTCAATAC | GGCAAAGTAA | AAGGCACAAC | GGAAAACGGC | 60 |
| GTACATAAGT | GGAAAGGCAT | CCCTTATGCC | AAGCCGCCTG | TCGGACAATG | GCGTTTTAAA | 120 |
| GCACCTGAGC | CGCCTGAAGT | GTGGGAAGAT | GTCCTTGATG | CCACAGCGTA | CGGTCCTATT | 180 |
| TGCCCGCAGC | CGTCTGATTT | GCTCTCACTG | TCGTATACAG | AGCTGCCCCG | CCAGTCCGAG | 240 |
| GATTGCTTGT | ACGTCAATGT | ATTTGCGCCT | GACACTCCAA | GTCAAAACCT | TCCTGTCATG | 300 |
| GTGTGGATTC | ACGGAGGCGC | TTTTTATCTA | GGAGCGGGCA | GTGAGCCATT | GTATGACGGA | 360 |
| TCAAAACTTG | CGGCACAGGG | AGAAGTCATT | GTCGTTACAT | TGAACTATCG | GCTGGGGCCG | 420 |
| TTTGGCTTTA | TGCACTTGTC | TTCGTTTGAT | GAGGCGTATT | CCGATAACCT | TGGGCTTTTA | 480 |
| GACCAAGCCG | CCGCGCTGAA | ATGGGTGCGG | GAGAATATCT | CAGCGTTTGG | CGGTGATCCC | 540 |
| GATAACGTAA | CAGTATTTGG | AGAATCCGCC | GGCGGCATGA | GCATTGCCGC | GCTGCTCGCT | 600 |
| ATGCCTGCGG | CAAAAGGCCT | GTTCCAGAAA | GCGATCATGG | AAAGCGGCGC | TTCCCGAACA | 660 |
| ATGACAAAAG | AACAAGCGGC | AAGCACTGCG | GCTGCCTTTT | TACAGGTCCT | TGGGATCAAT | 720 |
| GAGAGCCAGC | TGGACAGATT | GCATACTGTA | GCAGCGGAAG | ATTTGCTTAA | AGCGGCCGAT | 780 |
| CAGCTTCGGA | TTGCAGAAAA | AGAAAATATC | TTTCAGCTGT | TCTTCCAGCC | CGCCCTTGAT | 840 |
| CCGAAAACGC | TGCCTGAAGA | ACCAGAAAAA | TCGATCGCAG | AAGGGGCTGC | TTCCGGCATT | 900 |
| CCGCTATTGA | TTGAACAAC | CCGTGATGAA | GGATATTTAT | TTTTCACCCC | GGATTCAGAC | 960 |
| GTTCGTTCTC | AGGAAACGCT | TGATGCAGCA | CTCGAGTATT | TACTAGGGAA | GCCGCTGGCA | 1020 |
| GAGAAAGTTG | CCGATTTGTA | TCCGCGTTCT | CTGGAAAGCC | AAATTCATAT | GGTGACTGAT | 1080 |
| TTATTATTTT | GGCGCCCTGC | CGTCGCCTTT | GCATCCGCAC | AGTCTCATTA | CGCCCCTGTC | 1140 |
| TGGATGTACC | GGTTCGATTG | GCACCCGGAG | AAGCCGCCGT | ACAATAAAGC | GTTTCACGCA | 1200 |
| TTAGAGCTTC | CTTTTGTCTT | TGGAAATCTG | GACGGGTTGG | AACGAATGGC | AAAAGCGGAG | 1260 |
| ATTACGGATG | AGGTGAAACA | GCTTTCTCAC | ACGATACAAT | CCGCGTGGAT | CACGTTCGCT | 1320 |
| AAAACAGGAA | ACCCAAGCAC | CGAAGCTGTG | AATTGGCCGG | CGTATCATGA | AGAAACGAGA | 1380 |
| GAGACGGTGA | TTTTAGACTC | AGAGATTACG | ATCGAAAACG | ATCCCGAATC | TGAAAAAAGG | 1440 |
| CAGAAGCTAT | TCCCTTCAAA | AGGAGAATAA | | | | 1470 |

(2) INFORMATION FOR SEQ ID NO:20:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:20:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Pro Glu Val Trp
            35                  40                  45

Glu Asp Val Leu Asp Ala Thr Ala Tyr Gly Pro Ile Cys Pro Gln Pro
        50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
                180                 185                 190

Met Ser Ile Ala Ala Leu Leu Ala Met Pro Ala Ala Lys Gly Leu Phe
            195                 200                 205

Gln Lys Ala Ile Met Glu Ser Gly Ala Ser Arg Thr Met Thr Lys Glu
        210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
                260                 265                 270

Leu Phe Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
        290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
                340                 345                 350

Ser Gln Ile His Met Val Thr Asp Leu Leu Phe Trp Arg Pro Ala Val
            355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

(2) INFORMATION FOR SEQ ID NO:21:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 5-1a12

(ix) FEATURE:
        (A) NAME/KEY: CDS
        (B) LOCATION: complement (1..1470)

(xi) SEQUENCE DESCRIPTION: SEQ ID NO:21:

```
ATGACTCATC AAATAGTAAC GACTCAATAC GGCAAAGTAA AAGGCACAAC GGAAAACGGC    60

GTACATAAGT GGAAAGGCAT CCCTTATGCC AAGCCGCCTG TCGGACAATG GCGTTTTAAA   120

GCACCTGAGC CGCCTGAAGT GTGGGAAGAT GTCCTTGATG CCACAGCGTA CGGTCCTGTT   180

TGCCCGCAGC CGTCTGATTT GCTCTCACTG TCGTATACAG AGCTGCCCCG CCAGTCCGAG   240

GATTGCTTGT ATGTCAATGT ATTTGCGCCT GACACTCCAA GTCAAAACCT TCCTGTCATG   300

GTGTGGATTC ACGGAGGCGC TTTTTATCTA GGAGCGGGCA GTGAGCCATT GTATGACGGA   360

TCAAAACTTG CGGCACAGGG AGAAGTCATT GTCGTTACAT TGAACTATCG GCTGGGGCCG   420

TTTGGCTTTA TGCACTTGTC TTCGTTTGAT GAGGCGTATT CCGATAACCT TGGGCTTTTA   480

GACCAAGCCG CCGCGCTGAA ATGGGTGCGG GAGAATATCT CAGCGTTTGG CGGTGATCCC   540

GATAACGTAA CAGTATTTGG AGAATCCGCC GGCGGCATGA GCATTGCCGC GCTGCTCGCT   600

ATGCCTGCGG CAAAAGGCCT GTTCCAGAAA GCGATCATGG AAAGCGGCGC TTCCCGAACA   660

ATGACAAAAG AACAAGCGGC AAGCACTGCG GCTGCCTTTT TACAGGTCCT TGGGATTAAT   720

GAGAGCCAGC TGGACAGATT GCATACTGTA GCAGCGGAAG ATTTGCTTAA AGCGGCCGAT   780

CAGCTTCGGA TTGCAGAAAA AGAAAATATC TTTCAGCTGT TCTTCCAGCC CGCCCTTGAT   840

CCGAAAACGC TGCCTGAAGA ACCAGAAAAA TCGATCGCAG AAGGGGCTGC TTCCGGCATT   900

CCGCTATTGA TTGGAACAAC CCGTGATGAA GGATATTTAT TTTTCACCCC GGATTCAGAC   960
```

-continued

```
GTTCGTTCTC AGGAAACGCT TGATGCAGCA CTCGAGTATT TACTAGGGAA GCCGCTGGCA      1020

GAGAAAGCTG CCGATTTGTA TCCGCGTTCT CTGGAAAGCC AAATTCATAT GGTGACTGAT      1080

TTATTATTTT GGCGCCCTGC CGTCGCCTTT GCATCCGCAC AGTCTCATTA CGCCCCTGTC      1140

TGGATGTACC GGTTCGATTG CCACCCGGAG AAGCCGCCGT ACAATAAAGC GTTTCACGCA      1200

TTAGAGCTTC CTTTTGTCTT TGGAAATCTG GACGGGTTGG AACGAATGGC AAAAGCGGAG      1260

ATTACGGATG AGGTGAAACA GCTTTCTCAC ACGATACAAT CCGCGTGGAT CACGTTCGCT      1320

AAAACAGGAA ACCCAAGCAC CGAAGCTGTG AATTGGCCGG CGTATCATGA AGAAACGAGA      1380

GAGACGGTGA TTTTAGACTC AGAGATTACG ATCGAAAACG ATCCCGAATC TGAAAAAAGG      1440

CAGAAGCTAT TCCCTTCAAA AGGAGAATAA                                       1470
```

(2) INFORMATION FOR SEQ ID NO:22:

(i) SEQUENCE CHARACTERISTICS:
      (A) LENGTH: 489 amino acids
      (B) TYPE: amino acid
      (D) TOPOLOGY: linear (ii) MOLECULE TYPE: enzyme (xi) SEQUENCE DESCRIPTION: SEQ ID NO:22:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Glu Val Trp
        35                  40                  45

Glu Asp Val Leu Asp Ala Thr Ala Tyr Gly Pro Val Cys Pro Gln Pro
50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
                180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
        210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
```

|     |     |     |     | 260 |     |     |     | 265 |     |     |     | 270 |     |     |
| --- | --- | --- | --- | --- | --- | --- | --- | --- | --- | --- | --- | --- | --- | --- |

Leu Phe Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Ser Leu Gly
            325                 330                 335

Lys Pro Leu Ala Glu Lys Ala Ala Asp Leu Tyr Pro Arg Ser Leu Glu
            340                 345                 350

Ser Gln Ile His Met Val Thr Asp Leu Leu Phe Trp Arg Pro Ala Val
            355                 360                 365

Ala Phe Ala Ser Ala Gln Ser His Tyr Ala Pro Val Trp Met Tyr Arg
370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

(2) INFORMATION FOR SEQ ID NO:23:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: consensus (ix) FEATURE:
        (A) NAME/KEY: CDS
        (B) LOCATION: complement (1..1470)

(xi) SEQUENCE DESCRIPTION: SEQ ID NO:23:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCCG TCGGACAATG GCGTTTTAAA     120

GCACCTGAGC CGCCTGAAGT GTGGGAAGAT GTCCTTGATG CCACAGCGTA CGGTCCTGTT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAACCT TCCTGTCATG     300

GTGTGGATTC ACGGAGGCGC TTTTTATCTA GGAGCGGGCA GTGAGCCATT GTATGACGGA     360
```

```
TCAAAACTTG CGGCACAGGG AGAAGTCATT GTCGTTACAT TGAACTATCG GCTGGGGCCG       420

TTTGGCTTTA TGCACTTGTC TTCGTTTGAT GAGGCGTATT CCGATAACCT TGGGCTTTTA       480

GACCAAGCCG CCGCGCTGAA ATGGGTGCGG GAGAATATCT CAGCGTTTGG CGGTGATCCC       540

GATAACGTAA CAGTATTTGG AGAATCCGCC GGCGGCATGA GCATTGCCGC GCTGCTCGCT       600

ATGCCTGCGG CAAAAGGCCT GTTCAGAAAA GCGATCATGG AAAGCGGCGC TTCCCGAACA       660

ATGACAAAAG AACAAGCGGC AAGCACTGCG GCTGCCTTTT TACAGGTCCT TGGGATTAAT       720

GAGAGCCAGC TGGACAGATT GCATACTGTA GCAGCGGAAG ATTTGCTTAA AGCGGCCGAT       780

CAGCTTCGGA TTGCAGAAAA AGAAAATATC TTTCAGCTGT TCTTCCAGCC CGCCCTTGAT       840

CCGAAAACGC TGCCTGAAGA ACCAGAAAAA TCGATCGCAG AAGGGGCTGC TTCCGGCATT       900

CCGCTATTGA TTGGAACAAC CCGTGATGAA GGATATTTAT TTTTCACCCC GGATTCAGAC       960

GTTTATTCTC AGGAAACGCT TGATGCAGCA CTCGAGTATT TACTAGGGAA GCCGCTGGCA      1020

GAGAAAGTTG CCGATTTGTA TCCGCGTTCT CTGGAAAGCC AAATTCATAT GGTGACTGAT      1080

TTATTATTTT GGCGCCCTGC CGTCGCCTTT GCATCCGCAC AGTCTCATTA CGCCCCTGTC      1140

TGGATGTACC GGTTCGATTG GCACCCGGAG AAGCCGCCGT ACAATAAAGC GTTTCACGCA      1200

TTAGAGCTTC CTTTTGTCTT TGGAAATCTG GACGGRTTGG AACGAATGGC AAAAGCGGAG      1260

ATTACGGATG AGGTGAAACA GCTTTCTCAC ACGATACAAT CCGCGTGGAY CACGTTCGCT      1320

AAAACAGGAA ACCCAAGCAC CGAAGCTGTG AATTGGCCGG CGTATCATGA AGAAACGAGA      1380

GAGACGGTGA TTTTAGACTC AGAGATTACG ATCGAAAACG ATCCCGAATC TGAAAAAAGG      1440

CAGAAGCTAT TCCCTTCAAA AGGAGAATAA                                      1470

(2) INFORMATION FOR SEQ ID NO:24:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (xi) SEQUENCE DESCRIPTION: SEQ ID NO:24:

Met Thr His Gln Ile Val Thr Thr Gln Tyr Gly Lys Val Lys Gly Thr
  1               5                  10                  15

Thr Glu Asn Gly Val His Leu Trp Lys Gly Ile Pro Tyr Ala Lys Pro
                 20                  25                  30

Pro Val Gly Gln Trp Arg Phe Lys Ala Pro Glu Pro Glu Val Trp
             35                  40                  45

Glu Asp Val Leu Asp Ala Thr Ala Tyr Gly Pro Xaa Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Xaa Gln Xaa
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Xaa
130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
                165                 170                 175
Gly Gly Asp Pro Asp Asn Val Thr Val Phe Gly Glu Ser Ala Gly Gly
            180                 185                 190
Met Ser Ile Ala Ala Leu Leu Ala Met Pro Ala Ala Lys Gly Leu Phe
            195                 200                 205
Gln Lys Ala Ile Met Glu Ser Gly Ala Ser Arg Thr Met Thr Lys Glu
    210                 215                 220
Gln Ala Ala Ser Thr Ala Ala Ala Phe Leu Gln Val Leu Gly Ile Asn
225                 230                 235                 240
Glu Ser Gln Leu Asp Arg Leu His Thr Val Ala Ala Glu Asp Leu Leu
                245                 250                 255
Lys Ala Ala Asp Gln Leu Arg Ile Ala Glu Xaa Glu Asn Ile Xaa Gln
                260                 265                 270
Leu Phe Phe Gln Pro Ala Leu Asp Pro Lys Thr Leu Pro Glu Glu Pro
            275                 280                 285
Glu Lys Ser Ile Ala Glu Gly Ala Ala Ser Gly Ile Pro Leu Leu Ile
    290                 295                 300
Gly Thr Thr Arg Asp Glu Gly Tyr Leu Phe Phe Thr Pro Asp Ser Asp
305                 310                 315                 320
Val Xaa Ser Gln Glu Thr Leu Asp Ala Ala Leu Glu Tyr Xaa Leu Gly
                325                 330                 335
Lys Pro Leu Ala Glu Lys Xaa Ala Asp Leu Tyr Pro Arg Ser Leu Glu
            340                 345                 350
Ser Gln Ile His Met Xaa Thr Asp Leu Leu Phe Trp Arg Pro Ala Val
            355                 360                 365
Ala Xaa Ala Ser Ala Gln Ser His Tyr Ala Pro Val Trp Met Tyr Arg
    370                 375                 380
Phe Asp Trp His Pro Glu Lys Pro Pro Tyr Asn Lys Ala Phe His Ala
385                 390                 395                 400
Leu Glu Leu Pro Phe Val Phe Gly Asn Leu Asp Gly Leu Glu Arg Met
                405                 410                 415
Ala Lys Ala Glu Ile Thr Asp Glu Val Lys Gln Leu Ser His Thr Ile
                420                 425                 430
Gln Ser Ala Trp Ile Thr Phe Ala Lys Thr Gly Asn Pro Ser Thr Glu
            435                 440                 445
Ala Val Asn Trp Pro Ala Tyr His Glu Glu Thr Arg Glu Thr Val Ile
450                 455                 460
Leu Asp Ser Glu Ile Thr Ile Glu Asn Asp Pro Glu Ser Glu Lys Arg
465                 470                 475                 480
Gln Lys Leu Phe Pro Ser Lys Gly Glu
            485

(2) INFORMATION FOR SEQ ID NO:25:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
```

(A) ORGANISM:
        (C) INDIVIDUAL ISOLATE: 1A5D1

(ix) FEATURE:
        (A) NAME/KEY: CDS
        (B) LOCATION: complement (1..1470)

(xi) SEQUENCE DESCRIPTION: SEQ ID NO:25:

```
ATGACTCATC AAATAGTAAC GACTCAATAC GGCAAAGTAA AAGGCACAAC GGAAAACGGC    60

GTACATAAGT GGAAAGGCAT ACCTTATGCC AAGCCGCCTG TCGGACAATG GCGTTTTAAA   120

GCACCTGAGC CGCCTGAAGT GTGGGAAGAT GTCCTTGATG CCACAGCGTA CGGTCCTGTT   180

TGCCCGCAGC CGTCTGATTT GCTCTCACTG TCGTATACAG AGCTGCCCCG CCAGTCCGAG   240

GATTGCTTGT ATGTCAATGT ATTTGCGCCT GACACTCCAA GTCAAAACCT TCCTGTCATG   300

GTGTGGATTC ACGGAGGCGC TTTTTATCTA GGAGCGGGCA GTGAGCCATT GTATGACGGA   360

TCAAAACTTG CGGCACAGGG AGAAGTCATT GTCGTTACAT GAACTATCG GCTGGGGCCG    420

TTTGGCTTTA TGCACTTGTC TTCGTTTGAT GAGGCGTATT CCGATAACCT TGGGCTTTTA   480

GACCAAGCCG CCGCGCTGAA ATGGGTGCGG GAGAATATCT CAGCGTTTGG CGGTGATCCC   540

GATAACGTAA CAGTATTTGG AGAATCCGCC GGCGGCATGA GCATTGCCGC GCTGCTCGCT   600

ATGCCTGCGG CAAAAGGCCT GTTCCAGAAA GCGATCATGG AAAGCGGCGC TTCCCGAACA   660

ATGACAAAAG AACAAGCGGC AAGCACTGCG GCTGCCTTTT TACAGGTCCT TGGGATTAAT   720

GAGAGCCAGC TGGACAGATT GCATACTGTA GCAGCGGAAG ATTTGCTTAA AGCGGCCGAT   780

CAGCTTCGGA TTGCAGAAAA AGAAAATATC TTTCAGCTGT TCTTCCAGCC CGCCCTTGAT   840

CCGAAAACGC TGCCTGAAGA ACCAGAAAAA TCGATCGCAG AAGGGGCTGC TTCCGGCATT   900

CCGCTATTGA TTGGAACAAC CCGTGATGAA GGATATTTAT TTTTCACCCC GGATTCAGAC   960

GTTCGTTCTC AGGAAACGCT TGATGCAGCA CTCGAGTATT TACTAGGGAA GCCGCTGGCA  1020

GAGAAAGCTG CCGATTTGTA TCCGCGTTCT CTGGAAAGCC AAATTCATAT GGTGACTGAT  1080

TTATTATTTT GGCGCCCTGC CGTCGCCTTT GCATCCGCAC AGTCTCATTA CGCCCCTGTC  1140

TGGATGTACC GGTTCGATTG GCACCCGGAG AAGCCGCCGT ACAATAAAGC GTTTCACGCA  1200

TTAGAGCTTC CTTTTGTCTT TGGAAATCTG GACGGGTTGG AACGAATGGC AAAAGCGGAG  1260

ATTACGGATG AGGTGAAACA GCTTTCTCAC ACGATACAAT CCGCGTGGAT CACGTTCGCT  1320

AAAACAGGAA ACCCAAGCAC CGAAGCTGTG AATTGGCCGG CGTATCATGA AGAAACGAGA  1380

GAGACGGTGA TTTTAGACTC AGAGATTACG ATCGAAAACG ATCCCGAATC TGAAAAAAGG  1440

CAGAAGCTAT TCCCTTCAAA AGGAGAATAA                                  1470
```

(2) INFORMATION FOR SEQ ID NO:26:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (1A5D1)

(xi) SEQUENCE DESCRIPTION: SEQ ID NO:26:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45
```

```
Glu Asp Val Leu Asp Ala Thr Ala Tyr Gly Pro Val Cys Pro Gln Pro
    50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
                180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
                260                 265                 270

Leu Phe Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Ala Ala Asp Leu Tyr Pro Arg Ser Leu Glu
                340                 345                 350

Ser Gln Ile His Met Val Thr Asp Leu Leu Phe Trp Arg Pro Ala Val
            355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
                420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
        450                 455                 460

Leu Asp Ser Glu Ile Thr Ile Glu Asn Asp Pro Glu Ser Glu Lys Arg
465                 470                 475                 480
```

Gln Lys Leu Phe Pro Ser Lys Gly Glu
              485

(2) INFORMATION FOR SEQ ID NO:27:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 2A12

(ix) FEATURE:
        (A) NAME/KEY: CDS
        (B) LOCATION: complement (1..1470)

(xi) SEQUENCE DESCRIPTION: SEQ ID NO:27:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCCG TCGGACAATG GCGTTTTAAA     120

GCACCTGAGC CGCCTGAAGT GTGGGAAGAT GTCCTTGATG CCACAGCGTA CGGTCCTGTT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAACCT TCCTGTCATG     300

GTGTGGATTC ACGGAGGCGC TTTTTATCTA GGAGCGGGCA GTGAGCCATT GTATGACGGA     360

TCAAAACTTG CGGCACAGGG AGAAGTCATT GTCGTTACAT TGAACTATCG GCTGGGGCCG     420

TTTGGCTTTA TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTAT TTTTCACCCC GGATTCAGAC     960

GTTCGTTCTC AGGAAACGCT TGATGCAGCA CTCGAGTATT TACTAGGGAA GCCGCTGGCA    1020

GAGAAAGTTG CCGATTTGTA TCCGCGTTCT CTGGAAAGCC AAATTCATAT GGTGACTGAT    1080

TTATTATTTT GGCGCCCTGC CGTCGCCTTT GCATCCGCAC AGTCTCATTA CGCCCCTGTC    1140

TGGATGTACC GGTTCGATTG GCACCCGGAG AAGCCGCCGT ACAATAAAGC GTTTCACGCA    1200

TTAGAGCTTC CTTTTGTCTT TGGAAATCTG GACGGGTTGG AACGAATGGC AAAAGCGGAG    1260

ATTACGGATG AGGTGAAACA GCTTTCTCAC ACGATACAAT CCGCGTGGAT CACGTTCGCT    1320

AAAACAGGAA ACCCAAGCAC CGAAGCTGTG AATTGGCCGG CGTATCATGA AGAAACGAGA    1380

GAGACGGTGA TTTTAGACTC AGAGATTACG ATCGAAAACG ATCCCGAATC TGAAAAAAGG    1440

CAGAAGCTAT TCCCTTCAAA AGGAGAATAA                                    1470
```

(2) INFORMATION FOR SEQ ID NO:28:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (2A12)

(xi) SEQUENCE DESCRIPTION: SEQ ID NO:28:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Pro Glu Val Trp
         35                  40                  45

Glu Asp Val Leu Asp Ala Thr Ala Tyr Gly Pro Val Cys Pro Gln Pro
     50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Arg Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
                420                 425                 430

Gln Ser Ala Trp Ile Thr Phe Ala Lys Thr Gly Asn Pro Ser Thr Glu
            435                 440                 445

Ala Val Asn Trp Pro Ala Tyr His Glu Glu Thr Arg Glu Thr Val Ile
        450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

(2) INFORMATION FOR SEQ ID NO:29:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 3H5

(ix) FEATURE:
        (A) NAME/KEY: CDS
        (B) LOCATION: complement (1..1470)

(xi) SEQUENCE DESCRIPTION: SEQ ID NO:29:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCCG TCGGACAATG GCGTTTTAAA     120

GCACCTGAGC CGCCTGAAGT GTGGGAAGAT GTCCTTGATG CCACAGCGTA CGGTCCTGTT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAACCT TCCTGTCATG     300

GTGTGGATTC ACGGAGGCGC TTTTTATCTA GGAGCGGGCA GTGAGCCATT GTATGACGGA     360

TCAAAACTTG CGGCACAGGG AGAAGTCATT GTCGTTACAT TGAACTATCG GCTGGGGCCG     420

TTTGGCTTTA TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTAT TTTTCACCCC GGATTCAGAC     960
```

```
GTTTGTTCTC AGGAAACGCT TGATGCAGCA CTCGAGTATT TACTAGGGAA GCCGCTGGCA   1020

GAGAAAGTTG CCGATTTGTA TCCGCGTTCT CTGGAAAGCC AAATTCATAT GGTGACTGAT   1080

TTATTATTTT GGCGCCCTGC CGTCGCCTTT GCATCCGCAC AGTCTCATTA CGCCCCTGTC   1140

TGGATGTACC GGTTCGATTG GCACCCGGAG AAGCCGCCGT ACAATAAAGC GTTTCACGCA   1200

TTAGAGCTTC CTTTTGTCTT TGGAAATCTG GACGGGTTGG AACGAATGGC AAAAGCGGAG   1260

ATTACGGATG AGGTGAAACA GCTTTCTCAC ACGATACAAT CCGCGTGGGA CACGTTCGCT   1320

AAAACAGGAA ACCCAAGCAC CGAAGCTGTG AATTGGCCGG CGTATCATGA AGAAACGAGA   1380

GAGACGGTGA TTTTAGACTC AGAGATTACG ATCGAAAACG ATCCCGAATC TGAAAAAAGG   1440

CAGAAGCTAT TCCCTTCAAA AGGAGAATAA                                    1470
```

(2) INFORMATION FOR SEQ ID NO:30:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (3H5)

(xi) SEQUENCE DESCRIPTION: SEQ ID NO:30:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
                20                  25                  30

Pro Val Gly Gln Trp Arg Phe Lys Ala Pro Glu Pro Glu Val Trp
            35                  40                  45

Glu Asp Val Leu Asp Ala Thr Ala Tyr Gly Pro Val Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Lys Gly Leu Phe
    195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
```

|     |     |     |     |     | 260 |     |     |     | 265 |     |     |     |     | 270 |     |     |     |
| --- | --- | --- | --- | --- | --- | --- | --- | --- | --- | --- | --- | --- | --- | --- | --- | --- | --- |

Leu Phe Phe Gln Pro Ala Leu Asp Pro Lys Thr Leu Pro Glu Glu Pro
          275               280            285

Glu Lys Ser Ile Ala Glu Ala Ala Ser Gly Ile Pro Leu Leu Ile
290               295               300

Gly Thr Thr Arg Asp Glu Gly Tyr Leu Phe Thr Pro Asp Ser Asp
305              310              315          320

Val Cys Ser Gln Glu Thr Leu Asp Ala Ala Leu Glu Tyr Leu Leu Gly
          325               330           335

Lys Pro Leu Ala Glu Lys Val Ala Asp Leu Tyr Pro Arg Ser Leu Glu
          340             345            350

Ser Gln Ile His Val Met Thr Asp Leu Leu Phe Trp Arg Pro Ala Val
          355             360            365

Ala Phe Ala Ser Ala Gln Ser His Tyr Ala Pro Val Trp Met Tyr Arg
     370              375            380

Phe Asp Trp His Pro Glu Lys Pro Pro Tyr Asn Lys Ala Phe His Ala
385              390              395          400

Leu Glu Leu Pro Phe Val Phe Gly Asn Leu Asp Gly Leu Glu Arg Met
          405               410           415

Ala Lys Ala Glu Ile Thr Asp Glu Val Lys Gln Leu Ser His Thr Ile
          420             425            430

Gln Ser Ala Trp Thr Thr Phe Ala Lys Thr Gly Asn Pro Ser Thr Glu
     435              440            445

Ala Val Asn Trp Pro Ala Tyr His Glu Glu Thr Arg Glu Thr Val Ile
     450              455            460

Leu Asp Ser Glu Ile Thr Ile Glu Asn Asp Pro Glu Ser Glu Lys Arg
465              470              475          480

Gln Lys Leu Phe Pro Ser Lys Gly Glu
          485

(2) INFORMATION FOR SEQ ID NO:31:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 4G4

(ix) FEATURE:
        (A) NAME/KEY: CDS
        (B) LOCATION: complement (1..1470)

(xi) SEQUENCE DESCRIPTION: SEQ ID NO:31:

ATGACTCATC AAATAGTAAC GACTCAATAC GGCAAAGTAA AAGGCACAAC GGAAAACGGC    60

GTACATAAGT GGAAAGGCAT CCCTTATGCC AAGCCGCCCG TCGGACAATG GCGTTTTAAA   120

GCACCTGAGC CGCCTGAAGT GTGGGAAGAT GTCCTTGATG CCACAGCGTA CGGTCCTGTT   180

TGCCCGCAGC CGTCTGATTT GCTCTCACTG TCGTATACAG AGCTGCCCCG CCAGTCCGAG   240

GATTGCTTGT ATGTCAATGT ATTTGCGCCT GACACTCCAA GTCAAAACCT TCCTGTCATG   300

GTGTGGATTC ACGGAGGCGC TTTTTATCTA GGAGCGGGCA GTGAGCCATT GTATGACGGA   360

-continued

```
TCAAAACTTG CGGCACAGGG AGAAGTCATT GTCGTTACAT TGAACTATCG GCTGGGGCCG    420

TTTGGCTTTA TGCACTTGTC TTCGTTTGAT GAGGCGTATT CCGATAACCT TGGGCTTTTA    480

GACCAAGCCG CCGCGCTGAA ATGGGTGCGG GAGAATATCT CAGCGTTTGG CGGTGATCCC    540

GATAACGTAA CAGTATTTGG AGAATCCGCC GGCGGCATGA GCATTGCCGC GCTGCTCGCT    600

ATGCCTGCGG CAAAAGGCCT GTTCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT    720

GAGAGCCAGC TGGACAGATT GCATACTGTA GCAGCGGAAG ATTTGCTTAA AGCGGCCGAT    780

CAGCTTCGGA TTGCAGAAAA AGAAAATATC TTTCAGCTGC TCTTCCAGCC CGCCCTTGAT    840

CCGAAAACGC TGCCTGAAGA ACCAGAAAAA TCGATCGCAG AAGGGGCTGC TTCCGGCATT    900

CCGCTATTGA TTGGAACAAC CCGTGATGAA GGATATTTAT TTTTCACCCC GGATTCAGAC    960

GTTTATTCTC AGGAAACGCT TGATGCAGCA CTCGAGTATT TACTAGGGAA GCCGCTGGCA   1020

GAGAAAGTTG CCGATTTGTA TCCGCGTTCT CTGGAAAGCC AAATTCATAT GGTGACTGAT   1080

TTATTATTTT GGCGCCCTGC CGTCGCCTTT GCATCCGCAC AGTCTCATTA CGCCCCTGTC   1140

TGGATGTACC GGTTCGATTG GCACCCGGAG AAGCCGCCGT ACAATAAAGC GTTTCACGCA   1200

TTAGAGCTTC CTTTTGTCTT TGGAAATCTG GACGGGTTGG AACGAATGGC AAAAGCGGAG   1260

ATTACGGATG AGGTGAAACA GCTTTCTCAC ACGATACAAT CCGCGTGGGA CACGTTCGCT   1320

AAAACAGGAA ACCCAAGCAC CGAAGCTGTG AATTGGCCGG CGTATCATGA AGAAACGAGA   1380

GAGACGGTGA TTTTAGACTC AGAGATTACG ATCGAAAACG ATCCCGAATC TGAAAAAAGG   1440

CAGAAGCTAT TCCCTTCAAA AGGAGAATAA                                   1470
```

(2) INFORMATION FOR SEQ ID NO:32:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (4G4)

(xi) SEQUENCE DESCRIPTION: SEQ ID NO:32:

```
Met Thr His Gln Ile Val Thr Thr Gln Tyr Gly Lys Val Lys Gly Thr
  1               5                  10                  15

Thr Glu Asn Gly Val His Leu Trp Lys Gly Ile Pro Tyr Ala Lys Pro
                 20                  25                  30

Pro Val Gly Gln Trp Arg Phe Lys Ala Pro Glu Pro Glu Val Trp
             35                  40                  45

Glu Asp Val Leu Asp Ala Thr Ala Tyr Gly Pro Val Cys Pro Gln Pro
         50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160
```

```
Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
                260                 265                 270

Leu Leu Phe Gln Pro Ala Leu Asp Pro Lys Thr Leu Pro Glu Glu Pro
            275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val Tyr Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
                340                 345                 350

Ser Gln Ile His Met Val Thr Asp Leu Leu Phe Trp Arg Pro Ala Val
            355                 360                 365

Ala Phe Ala Ser Ala Gln Ser His Tyr Ala Pro Val Trp Met Tyr Arg
        370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Thr Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

(2) INFORMATION FOR SEQ ID NO:33:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
```

(A) ORGANISM:
(C) INDIVIDUAL ISOLATE: 5H3

(ix) FEATURE:
    (A) NAME/KEY: CDS
    (B) LOCATION: complement (1..1470)

(xi) SEQUENCE DESCRIPTION: SEQ ID NO:33:

| | | |
|---|---|---|
| ATGACTCATC AAATAGTAAC GACTCAATAC GGCAAAGTAA AAGGCACAAC GGAAAACGGC | 60 |
| GTACATAAGT GGAAAGGCAT CCCTTATGCC AAGCCGCCCG TCGGACAATG GCGTTTTAAA | 120 |
| GCACCTGAGC CGCCTGAAGT GTGGGAAGAT GTCCTTGATG CCACAGCGTA CGGTCCTGTT | 180 |
| TGCCCGCAGC CGTCTGATTT GCTCTCACTG TCGTATACAG AGCTGCCCCG CCAGTCCGAG | 240 |
| GATTGCTTGT ATGTCAATGT ATTTGCGCCT GACACTCCAA GTCAAAACCT TCCTGTCATG | 300 |
| GTGTGGATTC ACGGAGGCGC TTTTTATCTA GGAGCGGGCA GTGAGCCATT GTATGACGGA | 360 |
| TCAAAACTTG CGGCGCAGGG AGAAGTCATT GTCGTTACAT TGAACTATCG GCTGGGGCCG | 420 |
| TTTGGCTTTA TGCACTTGTC TTCGTTTGAT GAGGCGTATT CCGATAACCT TGGGCTTTTA | 480 |
| GACCAAGCCG CCGCGCTGAA ATGGGTGCGG GAGAATATCT CAGCGTTTGG CGGTGATCCC | 540 |
| GATAACGTAA CAGTATTTGG AGAATCCGCC GGCGGCATGA GCATTGCCGC GCTGCTCGCT | 600 |
| ATGCCTGCGG CAAAAGGCCT GTTCCAGAAA GCGATCATGG AAAGCGGCGC TTCCCGAACA | 660 |
| ATGACAAAAG AACAAGCGGC AAGCACTGCG GCTGCCTTTT TACAGGTCCT TGGGATTAAT | 720 |
| GAGAGCCAGC TGGACAGATT GCATACTGTA GCAGCGGAAG ATTTGCTTAA AGCGGCCGAT | 780 |
| CAGCTTCGGA TTGCAGAAAA AGAAAATATC TTTCAGCTGC TCTTCCAGCC CGCCCTTGAT | 840 |
| CCGAAAACGC TGCCTGAAGA ACCAGAAAAA TCGATCGCAG AAGGGGCTGC TTCCGGCATT | 900 |
| CCGCTATTGA TTGGAACAAC CCGTGATGAA GGATATTTCT TTTTCACCCC GGATTCAGAC | 960 |
| GTTTATTCTC AGGAAACGCT TGATGCAGCA CTCGAGTATT TACTAGGGAA GCCGCTGGCA | 1020 |
| GAGAAAGTTG CCGATTTGTA TCCGCGTTCT CTGGAAAGCC AAATTCATAT GGTGACTGAT | 1080 |
| TTATTATTTT GGCGCCCTGC CGTCGCCTTT GCATCCGCAC AGTCTCATTA CGCCCCTGTC | 1140 |
| TGGATGTACC GGTTCGATTG GCACCCGGAG AAGCCGCCGT ACAATAAAGC GTTTCACGCA | 1200 |
| TTAGAGCTTC CTTTTGTCTT TGGAAATCTG GACGGGTTGG AACGAATGGC AAAAGCGGAG | 1260 |
| ATTACGGATG AGGTGAAACA GCTTTCTCAC ACGATACAAT CCGCGTGGGA CACGTTCGCT | 1320 |
| AAAACAGGAA ACCCAAGCAC CGAAGCTGTG AATTGGCCGG CGTATCATGA AGAAACGAGA | 1380 |
| GAGACGGTGA TTTTAGACTC AGAGATTACG ATCGAAAACG ATCCCGAATC TGAAAAAAGG | 1440 |
| CAGAAGCTAT TCCCTTCAAA AGGAGAATAA | 1470 |

(2) INFORMATION FOR SEQ ID NO:34:

(i) SEQUENCE CHARACTERISTICS:
       (A) LENGTH: 489 amino acids
       (B) TYPE: amino acid
       (D) TOPOLOGY: linear (ii) MOLECULE TYPE: enzyme (5H3)

(xi) SEQUENCE DESCRIPTION: SEQ ID NO:34:

Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Pro Glu Val Trp
         35                  40                  45

-continued

```
Glu Asp Val Leu Asp Ala Thr Ala Tyr Gly Pro Val Cys Pro Gln Pro
     50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                     85                  90                  95

Leu Pro Val Met Val Trp Ile His Gly Gly Ala Phe Tyr Leu Gly Ala
                100                 105                 110

Gly Ser Glu Pro Leu Tyr Asp Gly Ser Lys Leu Ala Ala Gln Gly Glu
            115                 120                 125

Val Ile Val Val Thr Leu Asn Tyr Arg Leu Gly Pro Phe Gly Phe Met
        130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
                180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
                260                 265                 270

Leu Leu Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Phe Phe Phe Thr Pro Asp Ser Asp
305                 310                 315                 320

Val Tyr Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
                340                 345                 350

Ser Gln Ile His Met Val Thr Asp Leu Leu Phe Trp Arg Pro Ala Val
        355                 360                 365

Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
                420                 425                 430

Gln Ser Ala Trp Thr Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480
```

Gln Lys Leu Phe Pro Ser Lys Gly Glu
            485

(2) INFORMATION FOR SEQ ID NO:35:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 6H7

(ix) FEATURE:
        (A) NAME/KEY: CDS
        (B) LOCATION: complement (1..1470)

(xi) SEQUENCE DESCRIPTION: SEQ ID NO:35:

```
ATGACTCATC AAATAGTAAC GACTCAATAC GGCAAAGTAA AAGGCACAAC GGAAAACGGC      60

GTACATAAGT GGAAAGGCAT CCCTTATGCC AAGCCGCCCG TCGGACAATG GCGTTTTAAA     120

GCACCTGAGC CGCCTGAAGT GTGGGAAGAT GTCCTTGATG CCACAGCGTA CGGTCCTGTT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAACCT TCCTGTCATG     300

GTGTGGATTC ACGGAGGCGC TTTTTATCTA GGAGCGGGCA GTGAGCCATT GTATGACGGA     360

TCAAAACTTG CGGCGCAGGG AGAAGTCATT GTCGTTACAT TGAACTATCG GCTGGGGCCG     420

TTTGGCTTTA TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTCT TTTTCACCCC GGATTCAGAC     960

GTTTATTCTC AGGAAACGCT TGATGCAGCA CTCGAGTATT TACTAGGGAA GCCGCTGGCA    1020

GAGAAAGTTG CCGATTTGTA TCCGCGTTCT CTGGAAAGCC AAATTCATAT GGTGACTGAT    1080

TTATTATTTT GGCGCCCTGC CGTCGCCTTT GCATCCGCAC AGTCTCATTA CGCCCCTGTC    1140

TGGATGTACC GGTTCGATTG GCACCCGGAG AAGCCGCCGT ACAATAAAGC GTTACACGCA    1200

TTAGAGCTTC CTTTTGTCTT TGGAAATCTG GACGGGTTGG AACGAATGGC AAAAGCGGAG    1260

ATTACGGATG AGGTGAAACA GCTTTCTCAC ACGATACAAT CCGCGTGGGA CACGTTCGCT    1320

AAAACAGGAA ACCCAAGCAC CGAAGCTGTG AATTGGCCGG CGTATCATGA AGAAACGAGA    1380

GAGACGGTGA TTTTAGACTC AGAGATTACG ATCGAAAACG ATCCCGAATC TGAAAAAAGG    1440

CAGAAGCTAT TCCCTTCAAA AGGAGAATAA                                    1470
```

(2) INFORMATION FOR SEQ ID NO:36:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (6H7)

(xi) SEQUENCE DESCRIPTION: SEQ ID NO:36:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
             20                  25                  30

Pro Val Gly Gln Trp Arg Phe Lys Ala Pro Glu Pro Pro Glu Val Trp
         35                  40                  45

Glu Asp Val Leu Asp Ala Thr Ala Tyr Gly Pro Val Cys Pro Gln Pro
     50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ser Ile Ala Glu Gly Ala Ala Ser Gly Ile Pro Leu Leu Ile
    290                 295                 300

Gly Thr Thr Arg Asp Glu Gly Tyr Phe Phe Thr Pro Asp Ser Asp
305                 310                 315                 320

Val Tyr Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Val Thr Asp Leu Leu Phe Trp Arg Pro Ala Val
        355                 360                 365
```

```
Ala Phe Ala Ser Ala Gln Ser His Tyr Ala Pro Val Trp Met Tyr Arg
    370                 375                 380

Phe Asp Trp His Pro Glu Lys Pro Pro Tyr Asn Lys Ala Leu His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Thr Thr Phe Ala Lys Thr Gly Asn Pro Ser Thr Glu
        435                 440                 445

Ala Val Asn Trp Pro Ala Tyr His Glu Glu Thr Arg Glu Thr Val Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```

(2) INFORMATION FOR SEQ ID NO:37:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: 6sF9

(ix) FEATURE:
        (A) NAME/KEY: CDS
        (B) LOCATION: complement (1..1470)

(xi) SEQUENCE DESCRIPTION: SEQ ID NO:37:

```
ATGACTCATC AAATAGTAAC GACTCAATAC GGCAAAGTAA AAGGCACAAC GGAAAACGGC      60

GTACATAAGT GGAAAGGCAT CCCCTATGCC AAGCCGCCCG TCGGACAATG GCGTTTTAAA     120

GCACCTGAGC CGCCTGAAGT GTGGGAAGAT GTCCTTGATG CCACAGCGTA CGGTCCTGTT     180

TGCCCGCAGC CGTCTGATTT GCTCTCACTG TCGTATACAG AGCTGCCCCG CCAGTCCGAG     240

GATTGCTTGT ATGTCAATGT ATTTGCGCCT GACACTCCAA GTCAAAAGCT TCCTGTCATG     300

GTGTGGATTC ACGGAGGCGC TTTTTATCTA GGAGCGGGCA GTGAGCCATT GTATGACGGA     360

TCAAAACTTG CGGCACAGGG AGAAGTCATT GTCGTTACAT TGAACTATCG GCTGGGGCCG     420

TTTGGCTTTA TGCACTTGTC TTCGTTTGAT GAGGCGTATT CCGATAACCT TGGGCTTTTA     480

GACCAAGCCG CCGCGCTGAA ATGGGTGCGG GAGAATATCT CAGCGTTTGG CGGTGATCCC     540

GATAACGTAA CAGTATTTGG AGAATCCGCC GGCGGCATGA GCATTGCCGC GCTGCTCGCT     600

ATGCCTGCGG CAAAAGGCCT GTTCCAGAAA GCGATCATGG AAAGCGGCGC TTCCCGAACA     660

ATGACAAAAG AACAAGCGGC AAGCACTGCG GCTGCCTTTT TACAGGTCCT TGGGATTAAT     720

GAGAGCCAGC TGGACAGATT GCATACTGTA GCAGCGGAAG ATTTGCTTAA AGCGGCCGAT     780

CAGCTTCGGA TTGCAGAAAA AGAAAATATC TTTCAGCTGT TCTTCCAGCC CGCCCTTGAT     840

CCGAAAACGC TGCCTGAAGA ACCAGAAAAA TCGATCGCAG AAGGGGCTGC TTCCGGCATT     900

CCGCTATTGA TTGGAACAAC CCGTGATGAA GGATATTTCT TTTTCACCCC GGATTCAGAC     960
```

-continued

```
GTTTATTCTC AGGAAACGCT TGATGCAGCA CTCGAGTATT TACTAGGGAA GCCGCTGGCA    1020

GAGAAAGTTG CCGATTTGTA TCCGCGTTCT CTGGAAAGCC AAATTCATAT GGTGACTGAT    1080

TTATTATTTT GGCGCCCTGC CGTCGCCTTT GCATCCGCAC AGTCTCATTA CGCCCCTGTC    1140

TGGATGTACC GGTTCGATTG GCACCCGGAG AAGCCGCCGT ACAATAAAGC GTTTCACGCA    1200

TTAGAGCTTC CTTTTGTCTT TGGAAATCTG GACGAGTTGG AACGAATGGC AAAAGCGGAG    1260

ATTACGGATG AGGTGAAACA GCTTTCCCAC ACGATACAAT CCGCGTGGGA CACGTTCGCT    1320

AAAACAGGAA ACCCAAGCAC CGAAGCTGTG AATTGGCCGG CGTATCATGA AGAAACGAGA    1380

GAGACGGTGA TTTTAGACTC AGAGATTACG ATCGAAAACG ATCCCGAATC TGAAAAAAGG    1440

CAGAAGCTAT TCCCTTCAAA AGGAGAATAA                                    1470
```

(2) INFORMATION FOR SEQ ID NO:38:

(i) SEQUENCE CHARACTERISTICS:
        (A) LENGTH: 489 amino acids
        (B) TYPE: amino acid
        (D) TOPOLOGY: linear (ii) MOLECULE TYPE: enzyme (6sF9)

(xi) SEQUENCE DESCRIPTION: SEQ ID NO:38:

```
Met Thr His Gln Ile Val Thr Thr Gln Tyr Gly Lys Val Lys Gly Thr
 1               5                  10                  15

Thr Glu Asn Gly Val His Leu Trp Lys Gly Ile Pro Tyr Ala Lys Pro
            20                  25                  30

Pro Val Gly Gln Trp Arg Phe Lys Ala Pro Glu Pro Glu Val Trp
        35                  40                  45

Glu Asp Val Leu Asp Ala Thr Ala Tyr Gly Pro Val Cys Pro Gln Pro
 50                  55                  60

Ser Asp Leu Leu Ser Leu Ser Tyr Thr Glu Leu Pro Arg Gln Ser Glu
 65                  70                  75                  80

Asp Cys Leu Tyr Val Asn Val Phe Ala Pro Asp Thr Pro Ser Gln Asn
                 85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Met
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ala Ala Ala Phe Leu Gln Val Leu Gly Ile Asn
225                 230                 235                 240

Glu Ser Gln Leu Asp Arg Leu His Thr Val Ala Ala Glu Asp Leu Leu
                245                 250                 255

Lys Ala Ala Asp Gln Leu Arg Ile Ala Glu Lys Glu Asn Ile Phe Gln
```

```
                    260                265                270

Leu Phe Phe Gln Pro Ala Leu Asp Pro Lys Thr Leu Pro Glu Glu Pro
                275                280                285

Glu Lys Ser Ile Ala Glu Gly Ala Ala Ser Gly Ile Pro Leu Leu Ile
    290                295                300

Gly Thr Thr Arg Asp Glu Gly Tyr Phe Phe Thr Pro Asp Ser Asp
    305                310                315                320

Val His Ser Gln Glu Thr Leu Asp Ala Ala Leu Glu Tyr Leu Leu Gly
                325                330                335

Lys Pro Leu Ala Glu Lys Val Ala Asp Leu Tyr Pro Arg Ser Leu Glu
                340                345                350

Ser Gln Ile His Met Val Thr Asp Leu Leu Phe Trp Arg Pro Ala Val
                355                360                365

Ala Phe Ala Ser Ala Gln Ser His Tyr Ala Pro Val Trp Met Tyr Arg
                370                375                380

Phe Asp Trp His Pro Glu Lys Pro Pro Tyr Asn Lys Ala Phe His Ala
    385                390                395                400

Leu Glu Leu Pro Phe Val Phe Gly Asn Leu Asp Glu Leu Glu Arg Met
                405                410                415

Ala Lys Ala Glu Ile Thr Asp Glu Val Lys Gln Leu Ser His Thr Ile
                420                425                430

Gln Ser Ala Trp Tyr Thr Phe Ala Lys Thr Gly Asn Pro Ser Thr Glu
                435                440                445

Ala Val Asn Trp Pro Ala Tyr His Glu Glu Thr Arg Glu Thr Val Ile
                450                455                460

Leu Asp Ser Glu Ile Thr Ile Glu Asn Asp Pro Glu Ser Glu Lys Arg
    465                470                475                480

Gln Lys Leu Phe Pro Ser Lys Gly Glu
                485

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: RM1A (ix) FEATURE:
        (A) NAME/KEY: CDS
        (B) LOCATION: complement (1..21)

(xi) SEQUENCE DESCRIPTION: SEQ ID NO:39:

CAATTATCTA GACTACACGA G                                              21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

```
    (ii) MOLECULE TYPE: DNA (iii) HYPOTHETICAL: NO (iv) ANTI-SENSE: NO (vi) ORIGINAL SOURCE:
         (A) ORGANISM:
         (C) INDIVIDUAL ISOLATE: RM2A (ix) FEATURE:
         (A) NAME/KEY: CDS
         (B) LOCATION: complement (1..21)

(xi) SEQUENCE DESCRIPTION: SEQ ID NO:40:

GGTGGCTGAC ACTCGGTGAG G                                                   21
```

BIBLIOGRAPHY

1. H. Waldmann and D. Sebastian, Enzymatic Protecting Group Techniques, Chem. Rev. 1994, 94, 911–937.
2. Kametani, T., T. Honda, A. Nakayama, K. Fukumoto. Facile Synthesis of Carbapenem antibiotics. The first and simple stereoselective synthesis of antibiotic PS-5 benzyl ester. Heterocycles 14, 1967–1971 (1980).
3. Brannon, D. R., Mabe, J. A., and Fukuda, D. S. (1976). De-esterification of cephalosporin para-nitrobenzyl esters by microbial enzymes. J. Antibiotics 29:121–124.
4. Zock, J., Cantwell, C., Swartling, J., Hodges, R., Pohl, T., Sutton, K., Rosteck Jr., P., McGilvray, D., and Queener, S. (1994) The Bacillus subtilis pnbA gene encoding p-nitrobenzyl esterase—cloning, sequence and high-level expression in Escherichia coli. Gene 151:37–43.
5. Cooper, R. D. G. (1992). The carbacephems: a new beta-lactam antibiotic class. Am. J. Med. 92:6A/2S-6A/6S.
6. Chen, Y., Usui, S., Queener, S. W. and Yu, C. (1995). Purification and properties of p-nitrobenzyl esterase from Bacillus subtilis. J. Ind. Micro. 15:10–18.
7. Chen, K. and Arnold, F. (1991). Enzyme engineering for nonaqueous solvents—random mutagenesis to enhance activity of subtilisin E in polar organic media. Bio/Technology 9:1073–1077.
8. Chen, K. and Arnold, F. (1993). Tuning the activity of an enzyme for unusual environments: sequential random mutagenesis of subtilisin E for catalysis in dimethylformamide. Proc. Natl. Aced. Sci. U.S.A. 90:5618–5622.
9. You, L. and Arnold, F. H. (1995). Directed Evolution of Subtilisin E in Bacillus subtilis to Enhance Total Activity in Aqueous Dimethylformamide, Protein Engineeering, in press.
10. Leung, D. W., Chen, E., and Goeddel, D. V. (1989). A method for random mutagenesis of a defined DNA segment using a modified polymerase chain reaction. Technique 1:11–15.
11. Eckert, K. A. and Kunkel, T. A. (1991). DNA polymerase fidelity and the polymerase chain reaction. PCR Methods Applic. 1:17–24.
12. Cadwell, R. C., and Joyce, G. F. (1992). Randomization of genes by PCR mutagenesis. PCR Methods and Appl.:28–33.
13. Arnold, F. H. (1991). Metal-affinity separations—a new dimension in protein processing. Bio/Technology 9: 151–156.
14. Todd, R. J., Johnson, R. D. and Arnold, F. H. (1994). Multiple-site binding interactions in metal-affinity chromatography. 1. Equilibrium binding of engineered histidine-containing cytochrome-c. J. Chromat A 662:13–26.
15. Pohlenz, H. D., Boidol, W., Schuttke, I., and Streber, W. R. (1992). Purification and properties of an arthrobacter-oxydans p52 carbamate hydrolase specific for the herbicide phenmedipham and nucleotide-sequence of the corresponding gene. J. Bact. 174:6600–6607.
16. Tamura, N., Matsushita, Y., Iwama, T., Harada, S., Kishimoto, S. and Itoh, K. (1991), Synthesis and biological activity of (S)-2-amino-3-(2,5-dihydro-5-oxo-4-isoxazolyl)propanoic acid (TAN-950 A) derivatives, Chem. Pharm. Bull. 39:1199–212.
17. Garg, H. G. and Jeanloz, R. W. (1974), Synthesis of protected glycopeptides containing the amino acid sequences 34–37 and 34–38 of bovine ribonuclease B, Carbohyd. Res. 32:37–46.
18. Egan, L. P. (1972), Synthesis and acid-catalyzed hydrolysis of 3-O-glycosyl-L-serine and threonine, Carbohyd. Res. 23:261–73.
19. Hirayama, C., Ihara, H. and Shiraga, R. (1991), Induction of left-handed helical arrangement of 4-nitrobenzyl ester residues in cast film from poly(L-glutamate) by using a cationic bilayer forming compound, Chem. Lett. 8:1369–72.
20. Abiko, T. and Sekino, H. (1990), Synthesis of a thymosin $b_4$-like peptide, thymosin $b_q^{Met}$, and its effect on low E-rosette-forming lymphocytes of lupus nephritis patients, Chem. Pharm. Bull. 38:2301–4.
21. Suzuki, K. and Endo, N. (1978), The b-p-nitrobenzyl ester to minimize side reaction during treatment of aspartyl peptides with methanesulfonic acid, Chem. Pharm. Bull. 26:2269–74.
22. Barrett, G. C., Hardy, P. M., Harrow, T. A. and Rydon, H. N. (1972), Polypeptides. XXII. Synthesis of peptides of a-benzylphenylalanine by the dicyclohexycarbodiimide method. J. Chem. Soc., Perkin Trans. 1 20:2634–8.
23. Hruby, V. J., Ferger, M. F. and Du Vigneaud, V. (1971), Synthesis and pharmacological properties of deaminotocinamide nad a new synthesis of tocinamide, J. Amer. Chem. Soc. 93:5539–42.
24. Brunfeldt, K. and Halstrom, J. (1970), Tritylation of a partially protected pentapeptide synthesized by the Merrifield solid phase method. Acta Chem. Scand. 24:3013–18.
25. Hodges, R. S. and Merrifield, R. B. (1974), Synthesis of O-methyl-L-serine and $N^a$-tertbutyloxycarbonyl-O-methyl-L-serine, J. Org. Chem. 39:1870–2.
26. Stavropoulos, G. and Theodoropoulos, D. (1977), Synthesis of 4-substituted 1,4-benzodiazepine-3,5-diones, J. Heterocycl. Chem. 14 and 1139–43.
27. Schnyder, J. and Rottenberg, M. (1975), Improved synthesis of O-phosphohomoserine, Helv. Chem. Acta 58:518–21.
28. Jaenicke, R., Schurig, H., Beaucamp, N. and Ostendorp, R. (1996), Structure and stability of hyperstable proteins: Glycolytic enzymes from hyperthermophilic bacterium Thermotoga maritima. Advances in Prot. Chem. 48:181–269.

29. Querol, E., Perez-Pons, J. A. and Mozo-Villarias, A. (1996). Analysis of protein conformational characteristics related to thermostability. *Protein Engng* 9(3):265–271.
30. Russell, R. J. M. and Taylor, G. L. (1995), Engineering thermostability: lessons from thermophilic proteins. *Curr. Opin. Biotech* 6:370–374.
31. Vieille, C. and Zeikus, J. G. (1996), Thermozymes: identifying molecular determinants of protein structural and functional stability. *Trends Biotechnol* 14:183–191.
32. Matthews, B. W. (1993), Structural and genetic-analysis of protein stability. *Ann Rev Biochem* 62:139–160.
33. Matthews, B. W. (1995), Studies on protein stability with T4 lysozyme. *Advances in Prot Chem.* 46:249–278.
34. Jaenicke, R. (1996), Glyceraldehyde-3-phosphate dehydrogenase from *Thermotoga maritima: Strategies of protein stabilization. Ferns Microbiol Rev.* 18(2–3):215–224.
35. Daniel, R. M. (1996), The upper limits of enzyme thermal stability. *Enzyme and Microbial Tech* 19:74–79.
36. Stemmer, W. P. C. (1994), Rapid evolution of a protein in vitro by DNA shuffling. *Nature* 370:389–391.
37. Sanchez-Ruiz, J. M., López-Lacomba, J. L., Cortijo, M. and Mateo, P. L. (1988), Differential scanning calorimetry of the irreversible thermal denaturation of thermolysin. *Biochemistry* 27:1648–1652.
38. Freire, E., Osdol, W. W. V., Mayorga, O. L. and Sanchez-Ruiz, J. M. (1990), Calorimetrically determined dynamics of complex unfolding transitions in proteins. *Annu. Rev. Biophys. Chem.* 19:159–188.
39. Lorimer, I. A. and Pastan, I. (1995), Random recombination of antibody single chain Fv sequences after fragmentation with DNaseI in the presence of Mn2+. *Nucleic Acids Research* 23(15):3067–3068.
40. Sambrook, J., Fritsch, E. F. and Maniatis, T. (1989), *Molecular cloning: A laboratory manual.* 2 edit, Cold Spring Harbor Laboratory Press, Cold Spring Harbor, N.Y.
41. Ausubel, F. M., Brent, R., Kingston, R. E., Moore, D. D., Seidman, J. G., Smith, J. A. and Struhl, K., Eds. (1994–1997), Current Protocols in Molecular Biology, Vol. 1, Current Protocols in Molecular Biology. Edited by Chanda, V. B. 3 vols. New York: John Wiley & Sons.
42. Cadwell, R. C. and Joyce, G. F. (1994), Mutagenic PCR. *PCR Methods and Applications,* 3:S136–S140.
43. Moore, J. C. and Arnold, F. H. (1996), *Nat. Biotech* 14:458–467.
44. Arnold patent application Ser. No. 08/589,893, now U.S. Pat. No. 5,741,691.

What is claimed is:

1. A modified para-nitrobenzyl esterase having improved thermal stability relative to unmodified para-nitrobenzyl esterase of SEQ. ID. NO: 2 from *Bacillus subtilis,* wherein said modified para-nitrobenzyl esterase consists of unmodified para-nitrobenzyl esterase which has been modified by an amino acid substitution at one or more amino acid positions selected from the group consisting of amino acid position numbers 274, 313, 398, 412 and 437.

2. A thermostable para-nitrobenzyl esterase according to claim 1 wherein said modified para-nitribenzyl esterase consists of unmodified para-nitrobenzyl esterase which has further been modified by an amino acid substitution at one or more amino acid positions selected from the group consisting of amino acid position numbers 60, 94, 96, 144, 267, 271, 322, 334, 343, 358 and 370.

3. A thermostable para-nitrobenzyl esterase according to claim 1 wherein said one or more amino acid substitutions are selected from the group consisting of Phe 274 Leu, Leu 313 Phe, Phe 398 Leu, Gly 412 Glu and Ile 437 Thr.

4. A thermostable para-nitrobenzyl esterase according to claim 2 wherein said one or more amino acid substitutions are selected from the group consisting of Ile 60 Val, Ser 94 Gly, Asn 96 Ser, Leu 144 Met, Lys 267 Arg, Phe 271 Leu, His 322 Arg, His 322 Cys, His 322 Tyr, Leu 334 Val, Leu 334 Ser, Ala 343 Val, Met 358 Val, Tyr 370 Phe, Phe 398 Leu, Gly 412 Leu and Ile 437 Thr.

5. A thermostable para-nitrobenzyl esterase according to claim 2 wherein said para-nitrobenzyl esterase is modified by amino acid substitutions at positions 60, 144, 358 and 370.

6. A thermostable para-nitrobenzyl esterase according to claim 5 wherein said para-nitrobenzyl esterase is modified by amino acid substitutions Ile 60 Val, Leu 144 Met, Met 358 Val and Tyr 370 Phe.

7. A thermostable para-nitrobenzyl esterase according to claim 6 wherein said para-nitrobenzyl esterase is modified by amino acid substitutions selected from the group consisting of Phe 274 Leu, Leu 313 Phe, His 322 Arg, His 322 Cys, His 322 Tyr, Ala 343 Val, Phe 398 Leu, Gly 412 Glu and Ile 437 Thr.

8. A thermostable para-nitrobenzyl esterase according to claim 6 wherein said para-nitrobenzyl esterase is also modified by the amino acid substitution His 322 Arg.

9. A thermostable para-nitrobenzyl esterase according to claim 6 wherein said para-nitrobenzyl esterase is modified by the amino acid substitutions His 322 Arg and Ala 343 Val.

10. A thermostable para-nitrobenzyl esterase according to claim 6 wherein said para-nitrobenzyl esterase is modified by the amino acid substitutions His 322 Cys, Ala 343 Val and Ile 437 Thr.

11. A thermostable para-nitrobenzyl esterase according to claim 6 wherein said para-nitrobenzyl esterase is modified by the amino acid substitutions Phe 274 Leu, His 322 Tyr, Ala 343 Val and Ile 437 Thr.

12. A thermostable para-nitrobenzyl esterase according to claim 6 wherein said para-nitrobenzyl esterase is modified by the amino acid substitutions Phe 274 Leu, Leu 313 Phe, His 322 Tyr, Ala 343 Val and Ile 437 Thr.

13. A thermostable para-nitrobenzyl esterase according to claim 6 wherein said para-nitrobenzyl esterase is modified by the amino acid substitutions Leu 313 Phe, His 322 Tyr, Ala 343 Val, Phe 398 Leu and Ile 437 Thr.

14. A thermostable para-nitrobenzyl esterase according to claim 6 wherein said para-nitrobenzyl esterase is modified by the amino acid substitutions Leu 313 Phe, His 322 Tyr, Ala 343 Val, Gly 412 Glu and Ile 437 Thr.

15. A mixture at temperature above 50° C., said mixture comprising a modified para-nitrobenzyl esterase having improved thermal stability relative to unmodified para-nitrobenzyl esterase of SEQ. ID. NO: 2 from *Bacillus subtilis,* wherein said modified para-nitrobenzyl esterase consists of unmodified para-nitrobenzyl esterase which has been modified by an amino acid substitution at one or more amino acid positions selected from the group consisting of amino acid position numbers 274, 313, 398, 412 and 437.

* * * * *